US009689005B2

(12) United States Patent
Verwaal et al.

(10) Patent No.: US 9,689,005 B2
(45) Date of Patent: *Jun. 27, 2017

(54) SUCCINIC ACID PRODUCTION IN A EUKARYOTIC CELL

(71) Applicant: DSM IP ASSETS B.V., Heerlen (NL)

(72) Inventors: Rene Verwaal, Nootdorp (NL); Liang Wu, Delft (NL); Robbertus Antonius Damveld, Berkel en Rodenrijs (NL); Cornelis Maria Jacobus Sagt, Utrecht (NL)

(73) Assignee: DSM IP ASSETS B.V., Heerlen (NL)

( * ) Notice: Subject to any disclaimer, the term of this patent is extended or adjusted under 35 U.S.C. 154(b) by 0 days.

This patent is subject to a terminal disclaimer.

(21) Appl. No.: 14/044,722

(22) Filed: Oct. 2, 2013

(65) Prior Publication Data

US 2014/0031587 A1    Jan. 30, 2014

Related U.S. Application Data

(63) Continuation of application No. 12/743,106, filed as application No. PCT/EP2008/065583 on Nov. 14, 2008, now abandoned.

(30) Foreign Application Priority Data

| Nov. 20, 2007 | (EP) | 07121113 |
| Nov. 20, 2007 | (EP) | 07121117 |
| Nov. 20, 2007 | (EP) | 07121120 |
| May 27, 2008 | (EP) | 08156959 |
| May 27, 2008 | (EP) | 08156960 |
| May 27, 2008 | (EP) | 08156961 |

(51) Int. Cl.
*C12P 7/46* (2006.01)
*C12N 15/81* (2006.01)
*C12N 9/02* (2006.01)
*C12N 9/88* (2006.01)

(52) U.S. Cl.
CPC .......... *C12P 7/46* (2013.01); *C12N 9/001* (2013.01); *C12N 9/88* (2013.01); *C12N 15/81* (2013.01); *C12N 15/815* (2013.01); *Y02P 20/52* (2015.11)

(58) Field of Classification Search
CPC .......... C12P 7/46
USPC .......... 435/135
See application file for complete search history.

(56) References Cited

U.S. PATENT DOCUMENTS

| 4,828,993 | A | 5/1989 | Sridhar | |
| 5,643,758 | A * | 7/1997 | Guan et al. | 435/69.7 |
| 2006/0246560 | A1 | 11/2006 | Fatland-Bloom et al. | |
| 2007/0042477 | A1 | 2/2007 | Lee et al. | |

FOREIGN PATENT DOCUMENTS

| EP | 1672077 | 6/2006 |
| EP | 1867727 | 12/2007 |
| WO | 2006083410 | 8/2006 |
| WO | 2007019301 | 2/2007 |
| WO | 2007/030830 | 3/2007 |
| WO | 2007/061590 | 5/2007 |
| WO | 2008/144626 | 11/2008 |
| WO | 2008133161 A1 | 11/2008 |
| WO | 2009/011974 | 1/2009 |
| WO | 2013112939 A2 | 8/2013 |

OTHER PUBLICATIONS

Kubo et al, "Effect of Gene Disruption of Succinate Dehydrogenase on Succinate Production in a Sake Yeast Strain", Journal of Bioscience and Bioengineering, vol. 90, No. 6, 2000, pp. 619-624, XP003009625.
Song et al, "Production of Succinic Acid by Bacterial Fermentation", Enzyme and Microbial Technology, vol. 39, No. 3, Jul. 3, 2006, pp. 352-361, XP005459365.
Goldberg et al., "Organic Acids: old Metabolites, New Themes", Journal of Chemical Technology and Biotechnology, vol. 81, No. 10, Oct. 2006, pp. 1601-1611, XP002477014.
De Jongh "Organic Acid Production by Aspergillus Niger", PHD thesis, May 2006, pp. 1-109, XP002445685.
Ansell et al, "The two isoenzymes for yeast NAD+-dependent glycerol 3-phosphate dehydrogenase encoded by GPD1 and GPD2 have distinct roles in osmoadaptation and redox regulation", The EMBO Journal, vol. 16, No. 9, pp. 2179-2187, 1997.
International Search Report for PCT/EP2008/065582 mailed Feb. 12, 2009.
International Search Report for PCT/EP2008/065587 mailed Feb. 12, 2009.
International Search Report for PCT/EP2008/065588, mailed Feb. 12, 2009.
International Search Report for PCT/EP2008/065583, mailed Feb. 12, 2009.
U.S. Appl. No. 14/059,284, filed Oct. 2, 2013.
U.S. Appl. No. 14/070,770, filed Nov. 4, 2013.
U.S. Appl. No. 12/743,927, filed Sep. 15, 2010.
Fujimaki et al., "Processability and properties of aliphatic polyesters, 'Bionolle', synthesized by polycondensation reaction", Polymer Degradation and Stability, Barking, GB, vol. 59, No. 1-3, Jan. 3, 1998, pp. 209-214, XP027153158, ISSN: 0141-3910.
European Search Report corresponding to European Patent Application No. 13170415.7 dated Jan. 7, 2014.
May et al., "The Importance of Fungi to Man", Genome Research, (1997), vol. 7, pp. 1041-1044.
Wakai et al., "Formation of succinate during fermentation of sake mash and grape must", Brewing Technology (1980),2 vol. 58, No. 5, pp. 363-368 [Japanese Original and English Translation].

(Continued)

*Primary Examiner* — Tekchand Saidha
(74) *Attorney, Agent, or Firm* — McBee Moore Woodward & Vanik IP, LLC

(57) ABSTRACT

The present invention relates to a recombinant eukaryotic cell selected from a yeast of a filamentous fungus comprising a nucleotide sequence encoding a NAD(H)-dependent fumarate reductase that catalyzes the conversion of fumaric acid to succinic acid. The invention further relates to a process for the production of succinic acid wherein the eukaryotic cell according to the present invention is used.

17 Claims, 23 Drawing Sheets

(56) References Cited

OTHER PUBLICATIONS

Flores et al., "Carbohydrate and energy-yielding metabolism in non-conventional yeasts", FEMS Microbiology Reviews, (2000), vol. 24, pp. 507-529.
Karniely et al., "Single translation-dual destination: mechanisms of dual protein targeting in eukaryotes", EMBO Reports, (2005) vol. 6., No. 5, pp. 420-425.
Nobel/ et al., Protein promiscuity and its implications for biotechnology, Nature Biotechnology, (Feb. 9, 2009), vol. 27, No. 2, pp. 157-167.
Vallon et al., "New Sequence Motifs in Flavoproteins: Evidence for Common Ancestry and Tools to Predict Structure", (2000), Proteins: Structure, Fuction and Genetics, vol. 38, pp. 95-114.
Coustou et al., "A Mitochondria! NADH-dependent Fumarate Reductase Involved in the Production of Succinate Excreted by Procyclic Trypanosome Brucei", Journal of Biological Chemistry, vol. 280, No. 17, Apr. 2005, pa9es 16559-16570, XP002477924.
Database UniProt [online], Oct. 1, 1993, "Fumarate Recuctase (NADH) (EC 1.3.1.6) (NADH-dependent Fumarate Reductase) (FAD-Dependent Oxidoreductase FRDS)." XP002477929.
Database UniProt [online], Apr. 12, 2005, "Mitochondrial NADH-Dependent Fumarate Reductase (EC 1.3.1.6)." XP002477927.
Database UniProt [online], Mar. 1, 2003, "NADH-Dependent Fumarate Reductase." XP002477928.
Lin et al., "Metabolic Engineering of Aerobic Succinate Production Systems in *Escherichia coli* to Improve Process Productivity and Achieve the Maximum Theoretical Succinate Yield", Metabolic Engineering, vol. 7, No. 2, Mar. 2005, pp. 116-127, XP004801711.
Enomoto et al., "Physiolocial Role of Soluble Fumarate Recuctase in Redox Balancing during Anaerobiosis in *Saccharomyces cerevisiae*", FEMS Microbiology Letters, vol. 215, No. 1, Sep. 24, 2002, pp. 103-108, XP002477926.
Besteiro et al., "Succinate Secreted by Trypanosome Brucei is Produced by a Novel and Unique Glycosomal Enzyme, NADH-dependent Fumarate Reductase." Journal of Biological Chemistry, vol. 277, No. 41, Oct. 11, 2002, pp. 38001-38012, XP002477925.
De Jongh et al., "Enhanced Citrate Production through Gene insertion in Aspergillus Niger", Metabolic Engineering, vol. 10, No. 2, Nov. 17, 2007, pp. 87-96, XP022510142.
Kubo et al., "Effect of Gene Disruption of Succinate Dehydrogenase on Succinate Production in a Sake Yeast Strain", Journal of Bioscience and Bioengineering, vol. 90, No. 6, 2000, pp. 619-624, XP003009625.
Song et al., "Production of Succinic Acid by Bacterial Fermentation", Enzyme and Microbial Technology, vol. 39, No. 3, Jul. 3, 2006, pp. 352-361, XP005459365.
International Preliminary Report on Patentability for PCT/EP2008/065583, mailed Mar. 12, 2010.
Co-pending U.S. Appl. No. 12/743,416, filed May 18, 2010; WO 2009/065777.
Co-pending U.S. Appl. No. 127/743,652, filed May 19, 2010; WO 2009/065779.
Co-pending U.S. Appl. No. 12/743,927, filed May 20, 2010; WO 2009/065780.
International Search Report for PCT/EP2008/065582, mailed Feb. 12, 2009.
International Search Report for PCT/EP2008/065587, mailed Feb. 12, 2009.
Written Opinion of the International Searching Authority for PCT/EP2008/065587, mailed Feb. 12, 2009.
Written Opinion of the International Searching Authority, for PCT/EP2008/065588, mailed Feb. 12, 2009.
International Preliminary Report on Patentability for PCT/EP2008/065588, mailed Mar. 12, 2010.
Database UniProt [Online], Accession No. A2R097, (Mar. 6, 2007), 2 pages. XP-002477243.
Database UniProt [Online], Accession No. P55250, (Oct. 1, 1996), 1 page. XP-002477029.
Database UniProt [Online], "Fumarase.", Accession No. A6ZVZ4, (Sep. 11, 2007), 1 page. XP-002477030.
Database UniProt [Online], "Aspergillus niger contig Anl 2c0260; complete genome.", Accession No. AM270282, (Jan. 28, 2007), 28 pages. XP-002477242.
Friedberg, D., et al, "The fumR gene encoding fumarase in the filamentous fungus Rhizopus oryzae: cloning, structure and expression", Gene, vol. 163, No. 1, (Sep. 22, 1995), pp. 139-144.
Pines et al.; "The Cytosolic Pathway of L-malic Acid Synthesis in *Saccharomyces cerevisiae*: The Role of Fumarase", Applied Microbiology and Biotechnology, vol. 46, No. 4, 1996, pp. 393-399, XP008090537.
Peleg et al.; "Inducible Overexpression of the FUM1 Gene in *Saccharomyces cerevisiae*: Localization of Fumarase and Efficient Fumaric Acid Bioconversion to L-malic Acid", Applied and Environmental Microbiology, vol. 56, 1990, pp. 2777-2783, XP002408560.
Jacob et al.; "Fast High-Performance Liquid Chromatographic Purification of *Saccharomyces cerevisiae* Phosphoenolpyruvate Carboxykinase.", Journal of Chromatography, vol. 625, No. 1, Nov. 13, 1992, pp. 47-54, XP008091044.
Bauer et al.; "By-Product Formation during Exposure of Respiring *Saccharomyces cerevisiae* Cultures to Excess Glucose is not caused by a Limited Capacity of Pyruvate Carboxylase", FEMS Microbiology Letters, vol. 179, No. 1, Oct. 1, 1999, pp. 107-113, XP002478740.
Millard et al.; "Enhanced Production of Succinic Acid by Overexpression of Phosphoenolpyruvate Carboxylase in *Escherichia coli*", Applied and Environmental Microbiology, Washington, DC, US, vol. 62, No. 5, May 1, 1996, pp. 1808-1810, XP002132795.
Camarasa et al., Role in anaerobiosis of the isoenzymes for *Saccharomyces cerevisiae* fumarate reductase encoded by OSMI and FRDSI, Wiley Interscience, Mar. 7, 2007, pp. 391-401, Sciences pour l'Oenologie, INRA, Montpellier, France.
Chen et al., "Purification and enzymatic activity of an NADH-fumarate reductase and other mitochondrial activities of Leishmania parasites." APMIS (2001) 109: 801-808.
Chica et al., Curr Opin Biotechnol. Aug. 2005; 16(4):378-84.
Sen et al. Appl Biochem Biotechnol. Dec. 2007; 143(3):212-23.
Patil et al., "Evolutionary programming as a platform for in silico metabolic engineering" BMC Bioinformatics. Dec. 23, 2005; 6:308.
Warnecke et al., Organic acid toxicity, tolerance, and production in *Escherichia coli* biorefining applications. Microb. Cell Fact. 4:25. 2005.
Romanos et al., Foreign Gene Expression in Yeast: A Review. Yeast vol. 8:423-488 (1992).
Stewart et al. Biotechnology and Genetic Engineering Reviews, 14:67-143, 1997.
UnitProt Database—retrieved from the Internet via http://www.uniprot.org on Feb. 11, 2013.
Q6w6x5-UniProtKB/TrEMBL Database 2007.
De Jongh, W.A. et al., "Organic acid production by Aspergillus niger", BioCentrum-DTU, May 2006, pp. 51-58, 63-81.
Raab, Andreas M. et al., "Metabolic engineering of *Sacchaomyces cerevisiae* for the biotechnological production of succinic acid", Metabolic Engineering, 2010, pp. 518-525, vol. 12.
Schrickx, Jaap M. et al., "Organic Acid Production by Aspergillus niger in Recycling Culture Analyzed by Capillary Electrophoresis", Analytical Biochemistry, May 31, 1995, pp, 175-181, vol. 231.
Zeikus, J.G. et al., "Biotechnology of succinic acid production and markets for derived industrial products", Applied Microbiology and Biotechnology, 1999, pp. 545-552, vol. 51.

* cited by examiner

SEQUENCE LISTING

<160> NUMBER OF SEQ ID NOS: 44

<210> SEQ ID NO 1
<211> LENGTH: 1232
<212> TYPE: PRT
<213> ORGANISM: Trypanosoma brucei

<400> SEQUENCE: 1

Met Leu Ser Thr Lys Gln Leu Leu Arg Ala Thr Ser Ala Leu Val
1               5                   10                  15

Ala Gly Ser Ser Gly Val Ala Arg Asp Ser Pro Ser Leu Val Gly Asp
            20                  25                  30

-continued

Pro Cys Asp Ser Val Ser Pro Thr Arg Val Val Trp Gly Arg Phe Phe
        35                  40                  45

Lys Ser Leu Ala Pro Pro Ala Pro Ser Val Val Ser Cys Gln Lys Arg
 50                  55                  60

Phe Thr Ser His Gly Ala Asp Gly Ile Ser Ser Ala Ser Ile Val Val
 65                  70                  75                  80

Thr Asp Pro Glu Ala Ala Ala Lys Lys Arg Asp Arg Met Ala Arg Glu
                 85                  90                  95

Leu Leu Ser Ser Asn Ser Gly Leu Cys Gln Glu Asp Glu Pro Thr Ile
            100                 105                 110

Ile Asn Leu Lys Gly Leu Glu His Thr Ile Pro Tyr Arg Leu Ala Val
        115                 120                 125

Val Leu Cys Asn Ser Arg Ser Thr Gly Glu Phe Glu Ala Lys Ala Ala
130                 135                 140

Glu Ile Leu Arg Lys Ala Phe His Met Val Asp Tyr Ser Leu Asn Cys
145                 150                 155                 160

Phe Asn Pro Glu Ser Glu Leu Ser Arg Val Asn Ser Leu Pro Val Gly
                165                 170                 175

Glu Lys His Gln Met Ser Glu Asp Leu Arg His Val Met Glu Cys Thr
            180                 185                 190

Ile Ser Val His His Ser Ser Gly Met Gly Phe Asp Pro Ala Ala Gly
        195                 200                 205

Pro Ile Ile Ser Arg Leu Arg Gly Ala Met Arg Asp His Asn Asp Met
    210                 215                 220

Ser Asp Ile Ser Val Thr Glu Ala Glu Val Glu Leu Phe Ser Leu Ala
225                 230                 235                 240

Gln Ser Phe Asp Val Asp Leu Glu Glu Gly Thr Ile Ala Arg Lys His
                245                 250                 255

Ser Glu Ala Arg Leu Asp Leu Gly Gly Val Asn Lys Gly Tyr Thr Val
            260                 265                 270

Asp Tyr Val Val Asp His Leu Arg Ala Ala Gly Met Pro Asn Val Leu
        275                 280                 285

Phe Glu Trp Gly Gly Asp Ile Arg Ala Ser Gly Arg Asn Ile Lys Gly
    290                 295                 300

Asn Leu Trp Ala Val Ala Ile Lys Arg Pro Pro Ser Val Glu Glu Val
305                 310                 315                 320

Ile Arg Arg Ala Lys Gly Lys Met Leu Lys Met Gly Glu Glu Glu Gln
                325                 330                 335

Glu Glu Lys Asp Asp Asp Ser Pro Ser Leu Leu His Val Val Glu Leu
            340                 345                 350

Asp Asp Glu Ala Leu Cys Thr Ser Gly Asp Tyr Glu Asn Val Leu Tyr
        355                 360                 365

His Pro Lys His Gly Val Ala Gly Ser Ile Phe Asp Trp Gln Arg Arg
    370                 375                 380

Gly Leu Leu Ser Pro Glu Gly Ala Leu Ala Gln Val Ser Val Lys
385                 390                 395                 400

Cys Tyr Ser Ala Met Tyr Ala Asp Ala Leu Ala Thr Val Cys Leu Val
                405                 410                 415

Lys Arg Asp Ala Val Arg Ile Arg Tyr Leu Leu Glu Gly Trp Arg Tyr
            420                 425                 430

Val Arg Ser Arg Val Thr Asn Tyr Phe Ala Tyr Thr Arg Gln Gly Glu
        435                 440                 445

```
Arg Leu Ala His Met His Glu Ile Ala Gln Glu Thr Arg Glu Leu Arg
    450                 455                 460

Glu Ile Arg Ile Ala Gly Ser Leu Pro Ser Arg Ile Val Ile Val Gly
465                 470                 475                 480

Gly Gly Leu Ala Gly Leu Ser Ala Ala Ile Glu Ala Ala Ser Cys Gly
                485                 490                 495

Ala Gln Val Ile Leu Met Glu Lys Glu Gly Arg Ile Gly Gly Asn Ser
            500                 505                 510

Ala Lys Ala Thr Ser Gly Ile Asn Gly Trp Gly Thr Arg Thr Gln Ala
            515                 520                 525

Lys Ser Asp Ile Leu Asp Gly Lys Tyr Phe Glu Arg Asp Thr Phe
530                 535                 540

Leu Ser Gly Val Gly Gly Thr Thr Asp Pro Ala Leu Val Lys Val Leu
545                 550                 555                 560

Ser Val Lys Ser Gly Asp Ala Ile Gly Trp Leu Thr Ser Leu Gly Val
                565                 570                 575

Pro Leu Ser Val Leu Ser Gln Leu Gly Gly His Ser Phe Lys Arg Thr
                580                 585                 590

His Arg Ala Pro Asp Lys Thr Asp Gly Thr Pro Leu Pro Ile Gly His
                595                 600                 605

Thr Ile Met Arg Thr Leu Glu Asp His Ile Arg Asn Asn Leu Ser Glu
610                 615                 620

Arg Val Thr Ile Met Thr His Val Ser Val Thr Glu Leu Leu His Glu
625                 630                 635                 640

Thr Asp Thr Thr Pro Asp Gly Ala Ser Glu Val Arg Val Thr Gly Val
                645                 650                 655

Arg Tyr Arg Asp Leu Ser Asp Val Asp Gly Gln Pro Ser Lys Leu Leu
                660                 665                 670

Ala Asp Ala Val Val Leu Ala Thr Gly Gly Phe Ser Asn Asp Arg Glu
            675                 680                 685

Glu Asn Ser Leu Leu Cys Lys Tyr Ala Pro His Leu Ala Ser Phe Pro
690                 695                 700

Thr Thr Asn Gly Pro Trp Ala Thr Gly Asp Gly Val Lys Leu Ala Thr
705                 710                 715                 720

Ser Val Gly Ala Lys Leu Val Asp Met Asp Lys Val Gln Leu His Pro
                725                 730                 735

Thr Gly Leu Ile Asp Pro Lys Asp Pro Ala Asn Thr Thr Lys Ile Leu
                740                 745                 750

Gly Pro Glu Ala Leu Arg Gly Ser Gly Gly Ile Leu Leu Asn Lys Gln
            755                 760                 765

Gly Lys Arg Phe Val Asn Glu Leu Asp Leu Arg Ser Val Val Ser Lys
770                 775                 780

Ala Ile Asn Thr Gln Gly Asn Glu Tyr Pro Gly Ser Gly Gly Cys Tyr
785                 790                 795                 800

Phe Ala Tyr Cys Val Leu Asn Glu Asp Ala Thr Asn Leu Phe Cys Gly
                805                 810                 815

Gly Ala Leu Gly Phe Tyr Gly Lys Lys Leu Gly Leu Phe Gln Arg Ala
                820                 825                 830

Glu Thr Val Glu Glu Leu Ala Lys Leu Ile Gly Cys Asp Glu Gly Glu
            835                 840                 845

Leu Arg Asp Thr Leu Glu Lys Tyr Glu Thr Cys Ser Lys Ala Lys Val
850                 855                 860

Ala Cys Pro Val Thr Gly Lys Val Val Phe Pro Cys Val Val Gly Thr
```

```
                865                 870                 875                 880
Arg Gly Pro Tyr Asn Val Ala Phe Val Thr Pro Ser Ile His Tyr Thr
                    885                 890                 895

Met Gly Gly Cys Leu Ile Ser Pro Ala Ala Glu Val Leu Gln Glu Tyr
                900                 905                 910

Lys Gly Leu Asn Ile Leu Glu Asn His Arg Pro Ile Arg Cys Leu Phe
            915                 920                 925

Gly Ala Gly Glu Val Thr Gly Val His Gly Gly Asn Arg Leu Gly
        930                 935                 940

Gly Asn Ser Leu Leu Glu Cys Val Val Phe Gly Lys Ile Ala Gly Asp
945                 950                 955                 960

Arg Ala Ala Thr Ile Leu Gln Lys Arg Glu Ile Ala Leu Ser Lys Thr
                965                 970                 975

Ser Trp Thr Ser Val Val Arg Glu Ser Arg Ser Gly Glu Gln Phe
                980                 985                 990

Gly Thr Gly Ser Arg Val Leu Arg  Phe Asn Leu Pro Gly  Ala Leu Gln
            995                 1000                 1005

Arg Thr  Gly Leu Asn Leu Gly  Glu Phe Val Ala Ile  Arg Gly Glu
    1010                 1015                 1020

Trp Asp  Gly Gln Gln Leu Val  Gly Tyr Phe Ser Pro  Ile Thr Leu
    1025                 1030                 1035

Pro Glu  Asp Leu Gly Thr Ile  Ser Leu Leu Val Arg  Ala Asp Lys
    1040                 1045                 1050

Gly Thr  Leu Lys Glu Trp Ile  Cys Ala Leu Arg Pro  Gly Asp Ser
    1055                 1060                 1065

Val Glu  Ile Lys Ala Cys Gly  Gly Leu Arg Ile Asp  Gln Asp Pro
    1070                 1075                 1080

Val Lys  Lys Cys Leu Leu Phe  Arg Asn Arg Pro Ile  Thr Arg Phe
    1085                 1090                 1095

Ala Leu  Val Ala Ala Gly Thr  Gly Val Ala Pro Met  Leu Gln Val
    1100                 1105                 1110

Ile Arg  Ala Ala Leu Lys Lys  Pro Tyr Val Asp Thr  Leu Glu Ser
    1115                 1120                 1125

Ile Arg  Leu Ile Tyr Ala Ala  Glu Glu Tyr Asp Thr  Leu Thr Tyr
    1130                 1135                 1140

Arg Ser  Ile Leu Gln Arg Phe  Ala Glu Glu Phe Pro  Asp Lys Phe
    1145                 1150                 1155

Val Cys  Asn Phe Val Leu Asn  Asn Pro Pro Glu Gly  Trp Thr Gly
    1160                 1165                 1170

Gly Val  Gly Phe Val Asn Lys  Lys Ser Leu Gln Lys  Val Leu Gln
    1175                 1180                 1185

Pro Pro  Ser Ser Glu Pro Leu  Ile Val Val Cys Gly  Pro Pro Val
    1190                 1195                 1200

Met Gln  Arg Asp Val Lys Asn  Glu Leu Leu Ser Met  Gly Tyr Asp
    1205                 1210                 1215

Lys Glu  Leu Val His Thr Val  Asp Gly Glu Ser Gly  Thr Leu
    1220                 1225                 1230

<210> SEQ ID NO 2
<211> LENGTH: 3698
<212> TYPE: DNA
<213> ORGANISM: Trypanosoma brucei

<400> SEQUENCE: 2
```

```
atgctctcaa cgaagcaact tctccttcga gccacatctg cattagtggc gggaagctct    60
ggagttgcgc gagacagccc ttcgcttgtc ggcgacccct tcgactcggt ttcaccaacg   120
cgggtcgtat gggggcgctt cttcaaatcc ctagcgccac ccgctccctc ggttgtttca   180
tgtcaaaagc gttttacgtc ccatggcgcc gatggtattt cctcggcttc gattgttgtc   240
actgacccgg aggcggcagc aaagaagcgt gaccgcatgg cgcgcgagtt gctctcaagt   300
aatagtggtc tttgtcaaga gatgaaccc actatcatta acttaaaggg gttggagcac    360
acgattccgt acaggctcgc cgtggttctt tgtaactcgc gctctacagg tgaattcgaa   420
gcaaaggcag ctgagatttt gcgaaaggca tttcacatgg tggactactc cctcaattgt   480
ttcaatcctg aaagcgagtt gtcgcgtgtc aactctctgc cggtgggtga aagcatcaa    540 atgtcggagg atctccggca cgtgatggag tgcaccatca gtgtacatca ctccagcgga   600
atgggcttcg acccggcggc aggtccaatt atcagccgac ttcgggggc aatgagggac    660 cacaacgaca tgtccgacat ttccgtaacg gaagccgagg tagagctctt ctccttagcg   720
caaagttttg acgtggacct cgaggaggga acaaatagctc gcaagcactc tgaagcgagg   780
cttgatcttg gtggtgtgaa caaaggctac acagttgatt atgtagtgga tcatcttcgt   840
gcggccggta tgccaaacgt gctctttgag tggggcgggg atattcgagc gtcgggtagg   900
aacatcaaag gaaacctatg ggcagttgct atcaaacgac cgccatctgt ggaggaggtg   960
attcggcgcg ccaaagggaa aatgttaaaa atggggggagg aggagcagga agagaaggac  1020
gatgattctc catccctgct tcatgtggtg gagcttgatg atgaagccct ttgcaccagt  1080
ggtgactacg aaaacgtttt gtatcatcca agcatggag tggcggggag cattttgac    1140 tggcagcgaa gggggctact atctcctgag gaagggcac tcgctcaagt gtctgtgaaa    1200
tgttatagcg caatgtacgc tgatgctctg gcaacagtgt gccttgtgaa gcgtgatgct   1260
gtgaggattc gctacttatt agagggctgg cgttacgttc gaagtcgtgt gacgaattac   1320
tttgcctata cccgtcaggg cgagcggtta gcacatatgc acgagatagc gcaagaaaca   1380
cgggagctac gtgaaatacg gattgccggg agtttgccct ccagaattgt tattgtgggt   1440
ggaggtctag cgggccttc agcggccatc gaagccgcaa gttgtggtgc acaagtcata    1500
ctcatggaaa aggaaggaag aatcgggggg aacagcgcaa aggctacatc aggtattaat   1560
gggtggggga cgcgtacgca ggcaaagtca gatattctcg acggtggaaa gtattttgag   1620
cgtgacactt ttctctctgg cgttggcggt actaccgatc ctgccctcgt caaagtgctc   1680
tcagttaaga gtgggacgc aattggttgg cttacttctc ttggtgtgcc actcagtgtc    1740
ctctcgcaac ttggtggcca cagtttcaag cgaacccacc gtgccccgga caaaacggac   1800
gggacacccc taccaattgg tcatacgatc atgagaaccc tcgaggatca catccgtaac   1860
aacctctctg agcgagtaac gattatgaca catgtgtccg tgaccgagtt attgcacgaa   1920
accgatacaa cacctgatgg cgcctccgaa gtgcgtgtta cgggtgtaag atacagggac   1980
ctctccgatg tggatggcca gccatcaaaa ttgcttgcgg atgccgtcgt tcttgcaact   2040
ggtggtttct ccaatgaccg tgaagaaaat tcactgctct gcaagtatgc gcctcacctg   2100
gccagttttc caacgacaaa tggccctgg gcgaccggtg acggggttaa actcgcaaca    2160
tcggttggtg caaagcttgt ggatatggat aaggttcagc tacaccccac agggcttatc   2220
gatccaaagg atcccgcgaa cacaacgaag attctcggcc cggaggcact ccgaggttca   2280
ggtgggatat tactcaacaa gcaaggaaag cgcttcgtga tgaacttga cctccgctct    2340 gttgtatcca aggcaattaa tacgcagggt aatgaatacc ctggatccgg tggatgttac   2400
```

```
tttgcgtact gcgtgctcaa cgaagatgca acaaacctct tctgtggcgg tgcactgggg    2460
ttctacggaa agaagcttgg tttgttccag cgtgctgaga ctgtggaaga gttggccaaa    2520
ctgattggct gtgacgaagg tgaattacgg atacgcttg aaaagtatga acttgcagc     2580 aaggccaaag ttgcgtgccc tgtgacgggg aaggtagtat tcccttgtgt ggtgggtaca    2640 aggggggccgt acaatgttgc ttttgtcacg ccttccattc attacacaat gggtggctgc   2700
ctcatttcac cggctgctga agttcttcag gagtacaaag gtttaaatat tctggaaaac    2760
catagaccga ttcgatgctt gtttggtgcc ggtgaagtga cgggtggtgt gcacggtggt    2820
aaccgccttg gtggtaattc gctcttggaa tgtgtggtat tcgggaaaat tgcgggtgac    2880
cgtgccgcaa caatacttca aaaacgtgag atagccctct ccaagacgag ttggacttcc    2940
gttgttgtac gtgagtcccg ctccggcgaa cagttcggga ccggctctcg tgttcttcgt    3000
tttaacctac ctggggcgct gcagcgcaca ggtctcaatc tgggcgaatt tgtggccatc    3060
cgtggcgagt gggacggcca acaacttgtt ggttacttca gtccaattac actaccagag    3120
gaccttggca ctatctccct tctggttcgt gccgacaagg gcacattgaa ggaatggatc    3180
tgcgccttgc gaccgggcga ctccgtcgaa atcaaagcgt gtggaggtct tcgtattgat    3240
caagacccgg taaagaagtg tctgctgttt cgtaaccggc ctattacgcg gtttgctctt    3300
gtcgcggcag ggactggtgt cgcgcccatg ttgcaggtta ttcgtgcggc actcaagaag    3360
ccttacgtgg acacgttgga aagcatccgt cttatatacg ccgcagaaga gtacgacaca    3420
ttgacgtatc gctcaatttt gcagcggttt gcggaagagt tccccgacaa gttcgtctgc    3480
aacttcgttc ttaacaaccc acccgaaggg tggacaggtg gagtggggtt tgtcaacaaa    3540
aaatccctgc agaaggtgct gcaaccgcca tcgagtgagc cgctgattgt tgtgtgtgga    3600
ccgcccgtga tgcagcgcga cgtgaagaat gagttactga gcatgggtta tgacaaagag    3660
ctcgttcata cggttgacgg cgagtcggga acgctgta                            3698
```

<210> SEQ ID NO 3
<211> LENGTH: 1164
<212> TYPE: PRT
<213> ORGANISM: Artificial sequence
<220> FEATURE:
<223> OTHER INFORMATION: FRDm Trypanosoma lacking 68 aa targeting signal

<400> SEQUENCE: 3

```
Met Ala Asp Gly Ile Ser Ser Ala Ser Ile Val Val Thr Asp Pro Glu
1               5                   10                  15

Ala Ala Ala Lys Lys Arg Asp Arg Met Ala Arg Glu Leu Leu Ser Ser
                20                  25                  30

Asn Ser Gly Leu Cys Gln Glu Asp Glu Pro Thr Ile Ile Asn Leu Lys
        35                  40                  45

Gly Leu Glu His Thr Ile Pro Tyr Arg Leu Ala Val Val Leu Cys Asn
    50                  55                  60

Ser Arg Ser Thr Gly Glu Phe Glu Ala Lys Ala Ala Glu Ile Leu Arg
65                  70                  75                  80

Lys Ala Phe His Met Val Asp Tyr Ser Leu Asn Cys Phe Asn Pro Glu
                85                  90                  95

Ser Glu Leu Ser Arg Val Asn Ser Leu Pro Val Gly Glu Lys His Gln
                100                 105                 110

Met Ser Glu Asp Leu Arg His Val Met Glu Cys Thr Ile Ser Val His
        115                 120                 125
```

```
His Ser Ser Gly Met Gly Phe Asp Pro Ala Ala Gly Pro Ile Ile Ser
    130                 135                 140

Arg Leu Arg Gly Ala Met Arg Asp His Asn Asp Met Ser Asp Ile Ser
145                 150                 155                 160

Val Thr Glu Ala Glu Val Glu Leu Phe Ser Leu Ala Gln Ser Phe Asp
                165                 170                 175

Val Asp Leu Glu Glu Gly Thr Ile Ala Arg Lys His Ser Glu Ala Arg
            180                 185                 190

Leu Asp Leu Gly Gly Val Asn Lys Gly Tyr Thr Val Asp Tyr Val Val
        195                 200                 205

Asp His Leu Arg Ala Ala Gly Met Pro Asn Val Leu Phe Glu Trp Gly
    210                 215                 220

Gly Asp Ile Arg Ala Ser Gly Arg Asn Ile Lys Gly Asn Leu Trp Ala
225                 230                 235                 240

Val Ala Ile Lys Arg Pro Ser Val Glu Glu Val Ile Arg Arg Ala
                245                 250                 255

Lys Gly Lys Met Leu Lys Met Gly Glu Glu Gln Glu Lys Asp
                260                 265                 270

Asp Asp Ser Pro Ser Leu Leu His Val Val Glu Leu Asp Asp Glu Ala
            275                 280                 285

Leu Cys Thr Ser Gly Asp Tyr Glu Asn Val Leu Tyr His Pro Lys His
        290                 295                 300

Gly Val Ala Gly Ser Ile Phe Asp Trp Gln Arg Gly Leu Leu Ser
305                 310                 315                 320

Pro Glu Glu Gly Ala Leu Ala Gln Val Ser Val Lys Cys Tyr Ser Ala
                325                 330                 335

Met Tyr Ala Asp Ala Leu Ala Thr Val Cys Leu Val Lys Arg Asp Ala
            340                 345                 350

Val Arg Ile Arg Tyr Leu Leu Glu Gly Trp Arg Tyr Val Arg Ser Arg
        355                 360                 365

Val Thr Asn Tyr Phe Ala Tyr Thr Arg Gln Gly Glu Arg Leu Ala His
    370                 375                 380

Met His Glu Ile Ala Gln Glu Thr Arg Glu Leu Arg Glu Ile Arg Ile
385                 390                 395                 400

Ala Gly Ser Leu Pro Ser Arg Ile Val Ile Gly Gly Leu Ala
                405                 410                 415

Gly Leu Ser Ala Ala Ile Glu Ala Ala Ser Cys Gly Ala Gln Val Ile
            420                 425                 430

Leu Met Glu Lys Glu Gly Arg Ile Gly Gly Asn Ser Ala Lys Ala Thr
        435                 440                 445

Ser Gly Ile Asn Gly Trp Gly Thr Arg Thr Gln Ala Lys Ser Asp Ile
    450                 455                 460

Leu Asp Gly Gly Lys Tyr Phe Glu Arg Asp Thr Phe Leu Ser Gly Val
465                 470                 475                 480

Gly Gly Thr Thr Asp Pro Ala Leu Val Lys Val Leu Ser Val Lys Ser
                485                 490                 495

Gly Asp Ala Ile Gly Trp Leu Thr Ser Leu Gly Val Pro Leu Ser Val
            500                 505                 510

Leu Ser Gln Leu Gly Gly His Ser Phe Lys Arg Thr His Arg Ala Pro
        515                 520                 525

Asp Lys Thr Asp Gly Thr Pro Leu Pro Ile Gly His Thr Ile Met Arg
    530                 535                 540

Thr Leu Glu Asp His Ile Arg Asn Asn Leu Ser Glu Arg Val Thr Ile
```

```
                                545                 550                 555                 560
        Met Thr His Val Ser Val Thr Glu Leu Leu His Glu Thr Asp Thr Thr
                            565                 570                 575

Pro Asp Gly Ala Ser Glu Val Arg Val Thr Gly Val Arg Tyr Arg Asp
                        580                 585                 590

Leu Ser Asp Val Asp Gly Gln Pro Ser Lys Leu Leu Ala Asp Ala Val
                        595                 600                 605

Val Leu Ala Thr Gly Gly Phe Ser Asn Asp Arg Glu Glu Asn Ser Leu
                    610                 615                 620

Leu Cys Lys Tyr Ala Pro His Leu Ala Ser Phe Pro Thr Thr Asn Gly
        625                 630                 635                 640

Pro Trp Ala Thr Gly Asp Gly Val Lys Leu Ala Thr Ser Val Gly Ala
                            645                 650                 655

Lys Leu Val Asp Met Asp Lys Val Gln Leu His Pro Thr Gly Leu Ile
                            660                 665                 670

Asp Pro Lys Asp Pro Ala Asn Thr Thr Lys Ile Leu Gly Pro Glu Ala
                        675                 680                 685

Leu Arg Gly Ser Gly Gly Ile Leu Leu Asn Lys Gln Gly Lys Arg Phe
                        690                 695                 700

Val Asn Glu Leu Asp Leu Arg Ser Val Val Ser Lys Ala Ile Asn Thr
        705                 710                 715                 720

Gln Gly Asn Glu Tyr Pro Gly Ser Gly Gly Cys Tyr Phe Ala Tyr Cys
                            725                 730                 735

Val Leu Asn Glu Asp Ala Thr Asn Leu Phe Cys Gly Gly Ala Leu Gly
                        740                 745                 750

Phe Tyr Gly Lys Lys Leu Gly Leu Phe Gln Arg Ala Glu Thr Val Glu
                    755                 760                 765

Glu Leu Ala Lys Leu Ile Gly Cys Asp Glu Gly Glu Leu Arg Asp Thr
                    770                 775                 780

Leu Glu Lys Tyr Glu Thr Cys Ser Lys Ala Lys Val Ala Cys Pro Val
        785                 790                 795                 800

Thr Gly Lys Val Val Phe Pro Cys Val Val Gly Thr Arg Gly Pro Tyr
                            805                 810                 815

Asn Val Ala Phe Val Thr Pro Ser Ile His Tyr Thr Met Gly Gly Cys
                        820                 825                 830

Leu Ile Ser Pro Ala Ala Glu Val Leu Gln Glu Tyr Lys Gly Leu Asn
                        835                 840                 845

Ile Leu Glu Asn His Arg Pro Ile Arg Cys Leu Phe Gly Ala Gly Glu
        850                 855                 860

Val Thr Gly Gly Val His Gly Gly Asn Arg Leu Gly Gly Asn Ser Leu
        865                 870                 875                 880

Leu Glu Cys Val Val Phe Gly Lys Ile Ala Gly Asp Arg Ala Ala Thr
                            885                 890                 895

Ile Leu Gln Lys Arg Glu Ile Ala Leu Ser Lys Thr Ser Trp Thr Ser
                        900                 905                 910

Val Val Val Arg Glu Ser Arg Ser Gly Glu Gln Phe Gly Thr Gly Ser
                    915                 920                 925

Arg Val Leu Arg Phe Asn Leu Pro Gly Ala Leu Gln Arg Thr Gly Leu
                    930                 935                 940

Asn Leu Gly Glu Phe Val Ala Ile Arg Gly Glu Trp Asp Gly Gln Gln
        945                 950                 955                 960

Leu Val Gly Tyr Phe Ser Pro Ile Thr Leu Pro Glu Asp Leu Gly Thr
                            965                 970                 975
```

```
Ile Ser Leu Leu Val Arg Ala Asp Lys Gly Thr Leu Lys Glu Trp Ile
            980                 985                 990

Cys Ala Leu Arg Pro Gly Asp Ser Val Glu Ile Lys Ala Cys Gly Gly
        995                 1000                1005

Leu Arg Ile Asp Gln Asp Pro Val Lys Lys Cys Leu Leu Phe Arg
    1010                1015                1020

Asn Arg Pro Ile Thr Arg Phe Ala Leu Val Ala Ala Gly Thr Gly
    1025                1030                1035

Val Ala Pro Met Leu Gln Val Ile Arg Ala Ala Leu Lys Lys Pro
    1040                1045                1050

Tyr Val Asp Thr Leu Glu Ser Ile Arg Leu Ile Tyr Ala Ala Glu
    1055                1060                1065

Glu Tyr Asp Thr Leu Thr Tyr Arg Ser Ile Leu Gln Arg Phe Ala
    1070                1075                1080

Glu Glu Phe Pro Asp Lys Phe Val Cys Asn Phe Val Leu Asn Asn
    1085                1090                1095

Pro Pro Glu Gly Trp Thr Gly Gly Val Gly Phe Val Asn Lys Lys
    1100                1105                1110

Ser Leu Gln Lys Val Leu Gln Pro Pro Ser Ser Glu Pro Leu Ile
    1115                1120                1125

Val Val Cys Gly Pro Pro Val Met Gln Arg Asp Val Lys Asn Glu
    1130                1135                1140

Leu Leu Ser Met Gly Tyr Asp Lys Glu Leu Val His Thr Val Asp
    1145                1150                1155

Gly Glu Ser Gly Thr Leu
    1160

<210> SEQ ID NO 4
<211> LENGTH: 1142
<212> TYPE: PRT
<213> ORGANISM: Trypanosoma brucei

<400> SEQUENCE: 4

Met Val Asp Gly Arg Ser Ser Ala Ser Ile Val Ala Val Asp Pro Glu
1               5                   10                  15

Arg Ala Ala Arg Glu Arg Asp Ala Ala Ala Arg Ala Leu Leu Gln Asp
            20                  25                  30

Ser Pro Leu His Thr Thr Met Gln Tyr Ala Thr Ser Gly Leu Glu Leu
        35                  40                  45

Thr Val Pro Tyr Ala Leu Lys Val Val Ala Ser Ala Asp Thr Phe Asp
    50                  55                  60

Arg Ala Lys Glu Val Ala Asp Glu Val Leu Arg Cys Ala Trp Gln Leu
65                  70                  75                  80

Ala Asp Thr Val Leu Asn Ser Phe Asn Pro Asn Ser Glu Val Ser Leu
                85                  90                  95

Val Gly Arg Leu Pro Val Gly Gln Lys His Gln Met Ser Ala Pro Leu
            100                 105                 110

Lys Arg Val Met Ala Cys Cys Gln Arg Val Tyr Asn Ser Ser Ala Gly
        115                 120                 125

Cys Phe Asp Pro Ser Thr Ala Pro Val Ala Lys Ala Leu Arg Glu Ile
    130                 135                 140

Ala Leu Gly Lys Glu Arg Asn Asn Ala Cys Leu Glu Ala Leu Thr Gln
145                 150                 155                 160

Ala Cys Thr Leu Pro Asn Ser Phe Val Ile Asp Phe Glu Ala Gly Thr
```

```
                165                 170                 175
Ile Ser Arg Lys His Glu His Ala Ser Leu Asp Leu Gly Gly Val Ser
            180                 185                 190
Lys Gly Tyr Ile Val Asp Tyr Val Asp Asn Ile Asn Ala Ala Gly
        195                 200             205
Phe Gln Asn Val Phe Phe Asp Trp Gly Asp Cys Arg Ala Ser Gly
    210                 215                 220
Met Asn Ala Arg Asn Thr Pro Trp Val Gly Ile Thr Arg Pro Pro
225                 230                 235                 240
Ser Leu Asp Met Leu Pro Asn Pro Lys Glu Ala Ser Tyr Ile Ser
                245                 250                 255
Val Ile Ser Leu Asp Asn Glu Ala Leu Ala Thr Ser Gly Asp Tyr Glu
            260                 265                 270
Asn Leu Ile Tyr Thr Ala Asp Asp Lys Pro Leu Thr Cys Thr Tyr Asp
        275                 280                 285
Trp Lys Gly Lys Glu Leu Met Lys Pro Ser Gln Ser Asn Ile Ala Gln
    290                 295                 300
Val Ser Val Lys Cys Tyr Ser Ala Met Tyr Ala Asp Ala Leu Ala Thr
305                 310                 315                 320
Ala Cys Phe Ile Lys Arg Asp Pro Ala Lys Val Arg Gln Leu Leu Asp
                325                 330                 335
Gly Trp Arg Tyr Val Arg Asp Thr Val Arg Asp Tyr Arg Val Tyr Val
            340                 345                 350
Arg Glu Asn Glu Arg Val Ala Lys Met Phe Glu Ile Ala Thr Glu Asp
        355                 360                 365
Ala Glu Met Arg Lys Arg Ile Ser Asn Thr Leu Pro Ala Arg Val
    370                 375                 380
Ile Val Val Gly Gly Leu Ala Gly Leu Ser Ala Ile Glu Ala
385                 390                 395                 400
Ala Gly Cys Gly Ala Gln Val Val Leu Met Glu Lys Glu Ala Lys Leu
                405                 410                 415
Gly Gly Asn Ser Ala Lys Ala Thr Ser Gly Ile Asn Gly Trp Gly Thr
            420                 425                 430
Arg Ala Gln Ala Lys Ala Ser Ile Val Asp Gly Gly Lys Tyr Phe Glu
        435                 440                 445
Arg Asp Thr Tyr Lys Ser Gly Ile Gly Gly Asn Thr Asp Pro Ala Leu
    450                 455                 460
Val Lys Thr Leu Ser Met Lys Ser Ala Asp Ala Ile Gly Trp Leu Thr
465                 470                 475                 480
Ser Leu Gly Val Pro Leu Thr Val Leu Ser Gln Leu Gly Gly His Ser
                485                 490                 495
Arg Lys Arg Thr His Arg Ala Pro Asp Lys Lys Asp Gly Thr Pro Leu
            500                 505                 510
Pro Ile Gly Phe Thr Ile Met Lys Thr Leu Glu Asp His Val Arg Gly
        515                 520                 525
Asn Leu Ser Gly Arg Ile Thr Ile Met Glu Asn Cys Ser Val Thr Ser
    530                 535                 540
Leu Leu Ser Glu Thr Lys Glu Arg Pro Asp Gly Thr Lys Gln Ile Arg
545                 550                 555                 560
Val Thr Gly Val Glu Phe Thr Gln Ala Gly Ser Gly Lys Thr Thr Ile
                565                 570                 575
Leu Ala Asp Ala Val Ile Leu Ala Thr Gly Gly Phe Ser Asn Asp Lys
            580                 585                 590
```

```
Thr Ala Asp Ser Leu Leu Arg Glu His Ala Pro His Leu Val Asn Phe
            595                 600                 605

Pro Thr Thr Asn Gly Pro Trp Ala Thr Gly Asp Gly Val Lys Leu Ala
        610                 615                 620

Gln Arg Leu Gly Ala Gln Leu Val Asp Met Asp Lys Val Gln Leu His
625                 630                 635                 640

Pro Thr Gly Leu Ile Asn Pro Lys Asp Pro Ala Asn Pro Thr Lys Phe
                645                 650                 655

Leu Gly Pro Glu Ala Leu Arg Gly Ser Gly Val Leu Leu Asn Lys
            660                 665                 670

Gln Gly Lys Arg Phe Val Asn Glu Leu Asp Leu Arg Ser Val Val Ser
        675                 680                 685

Lys Ala Ile Met Glu Gln Gly Ala Glu Tyr Pro Gly Ser Gly Gly Ser
690                 695                 700

Met Phe Ala Tyr Cys Val Leu Asn Ala Ala Gln Lys Leu Phe Gly
705                 710                 715                 720

Val Ser Ser His Glu Phe Tyr Trp Lys Lys Met Gly Leu Phe Val Lys
                725                 730                 735

Ala Asp Thr Met Arg Asp Leu Ala Ala Leu Ile Gly Cys Pro Val Glu
            740                 745                 750

Ser Val Gln Gln Thr Leu Glu Glu Tyr Glu Arg Leu Ser Ile Ser Gln
        755                 760                 765

Arg Ser Cys Pro Ile Thr Arg Lys Ser Val Tyr Pro Cys Val Leu Gly
770                 775                 780

Thr Lys Gly Pro Tyr Tyr Val Ala Phe Val Thr Pro Ser Ile His Tyr
785                 790                 795                 800

Thr Met Gly Gly Cys Leu Ile Ser Pro Ser Ala Glu Ile Gln Met Lys
                805                 810                 815

Asn Thr Ser Ser Arg Ala Pro Leu Ser His Ser Asn Pro Ile Leu Gly
            820                 825                 830

Leu Phe Gly Ala Gly Glu Val Thr Gly Gly Val His Gly Gly Asn Arg
        835                 840                 845

Leu Gly Gly Asn Ser Leu Leu Glu Cys Val Val Phe Gly Arg Ile Ala
850                 855                 860

Gly Asp Arg Ala Ser Thr Ile Leu Gln Arg Lys Ser Ser Ala Leu Ser
865                 870                 875                 880

Phe Lys Val Trp Thr Thr Val Leu Arg Glu Val Arg Glu Gly Gly
            885                 890                 895

Val Tyr Gly Ala Gly Ser Arg Val Leu Arg Phe Asn Leu Pro Gly Ala
        900                 905                 910

Leu Gln Arg Ser Gly Leu Ser Leu Gly Gln Phe Ile Ala Ile Arg Gly
        915                 920                 925

Asp Trp Asp Gly Gln Gln Leu Ile Gly Tyr Tyr Ser Pro Ile Thr Leu
930                 935                 940

Pro Asp Asp Leu Gly Met Ile Asp Ile Leu Ala Arg Ser Asp Lys Gly
945                 950                 955                 960

Thr Leu Arg Glu Trp Ile Ser Ala Leu Glu Pro Gly Asp Ala Val Glu
                965                 970                 975

Met Lys Ala Cys Gly Gly Leu Val Ile Glu Arg Arg Leu Ser Asp Lys
            980                 985                 990

His Phe Val Phe Met Gly His Ile Ile Asn Lys Leu Cys Leu Ile Ala
        995                 1000                1005
```

| | | | | | | | | | | |
|---|---|---|---|---|---|---|---|---|---|---|
| Gly | Gly | Thr | Gly | Val | Ala | Pro | Met | Leu | Gln | Ile | Ile | Lys | Ala | Ala |
| 1010 | | | | | 1015 | | | | | 1020 |

| Phe | Met | Lys | Pro | Phe | Ile | Asp | Thr | Leu | Glu | Ser | Val | His | Leu | Ile |
| 1025 | | | | | 1030 | | | | | 1035 |

| Tyr | Ala | Ala | Glu | Asp | Val | Thr | Glu | Leu | Thr | Tyr | Arg | Glu | Val | Leu |
| 1040 | | | | | 1045 | | | | | 1050 |

| Glu | Glu | Arg | Arg | Arg | Glu | Ser | Arg | Gly | Lys | Phe | Lys | Lys | Thr | Phe |
| 1055 | | | | | 1060 | | | | | 1065 |

| Val | Leu | Asn | Arg | Pro | Pro | Leu | Trp | Thr | Asp | Gly | Val | Gly | Phe |
| 1070 | | | | | 1075 | | | | | 1080 |

| Ile | Asp | Arg | Gly | Ile | Leu | Thr | Asn | His | Val | Gln | Pro | Pro | Ser | Asp |
| 1085 | | | | | 1090 | | | | | 1095 |

| Asn | Leu | Leu | Val | Ala | Ile | Cys | Gly | Pro | Pro | Val | Met | Gln | Arg | Ile |
| 1100 | | | | | 1105 | | | | | 1110 |

| Val | Lys | Ala | Thr | Leu | Lys | Thr | Leu | Gly | Tyr | Asn | Met | Asn | Leu | Val |
| 1115 | | | | | 1120 | | | | | 1125 |

| Arg | Thr | Val | Asp | Glu | Thr | Glu | Pro | Ser | Gly | Ser | Ser | Lys | Ile |
| 1130 | | | | | 1135 | | | | | 1140 |

<210> SEQ ID NO 5
<211> LENGTH: 3429
<212> TYPE: DNA
<213> ORGANISM: Trypanosoma brucei

<400> SEQUENCE: 5

```
atggtagacg ggcgatcttc tgcatcaatt gttgccgttg atcccgaaag ggctgcgcgt      60
gagcgcgacg cagcagcgcg tgcccttctt caagacagtc cgctacacac gaccatgcaa     120
tatgcaacgt ctggtcttga gcttaccgtt ccctatgcac ttaaggtggt tgccagtgct     180
gacaccttcg atcgcgctaa ggaggttgcc gatgaggtgc tacgctgcgc atggcaactc     240
gccgacaccg tgttgaacag tttcaacccg aacagtgagg tttcactcgt gggtcgcctg     300
cctgtggggc agaagcacca aatgtctgct ccactcaagc gtgtgatggc atgctgccag     360
cgtgtgtata actcatcggc tggatgtttt gatccctcca cagcacccgt cgcaaaggcg     420
ctgcgtgaga ttgcactggg gaaggagcgg aacaatgctt gtctggaggc acttactcaa     480
gcgtgtacgc ttcccaacag ttttgtgatc gatttcgaag ctggaactat cagccgtaag     540
cacgagcatg cgtctctgga cctaggtggg gttagcaaag gttatatcgt tgattatgtc     600
attgataata tcaatgctgc tggatttcaa aacgtttttt ttgactgggg tggagactgc     660
cgtgcgagtg gtatgaatgc gcgcaatacc ccgtgggttg ttggtataac tcgccctccg     720
tcccttgata tgctccctaa cccgccaaag gaggcgtcgt atatcagcgt tatctctctc     780
gacaacgagg cccttgccac gagtggcgat tatgaaaact aatatacac cgctgatgat      840 aaaccccta cctgcactta tgactggaag gggaaggaac tgatgaaacc ttctcagtcc     900
aatatcgcgc aggtatcggt taaatgttat agcgccatgt acgctgacgc gcttgcgact     960
gcgtgtttca taaagcggga tcccgcgaag gttcgacagc tgctggacgg ttggcgttac    1020
gtgcgtgata cagtgagaga ttacagggtc tacgttcgtg aaaatgagcg agtagcgaag    1080
atgtttgaga tcgccacaga ggatgcggaa atgaggaaga ggcggatcag caacacactt    1140
cccgctcgtg tcattgtggt gggcggtggt cttgcgggtt tgtccgcggc catcgaagct    1200
gcaggatgcg gtgctcaggt tgtgcttatg gagaaggagg cgaagctcgg aggcaacagc    1260
gccaaggcga catctggtat caacggatgg ggcacacgtg ctcaggcgaa ggcaagcatt    1320
```

```
gtggatggtg ggaaatactt cgagcgtgac acatacaagt ctggtatcgg gggtaacacc      1380
gatcctgccc ttgtgaagac actttctatg aaaagtgctg acgctattgg gtggctgacc      1440
tcgttgggtg taccgctgac ggtattgtca cagcttgggg gtcacagccg caagcgcaca      1500
catcgggcac cggataagaa agatggtaca cctctaccta tcggatttac aatcatgaaa      1560
accctcgagg atcacgtgcg tggtaacctt tctggccgca tcaccataat ggaaaactgc      1620
agtgtaacgt cgttgctcag tgagacgaag gaacggccag atggcactaa acagatacga      1680
gttactggtg tggagttcac gcaggctggc agtgggaaga cgaccatact tgcagatgct      1740
gtcatccttg ccactggtgg attttctaac gacaaaactg cagactccct gcttcgtgag      1800
cacgccccgc acttggtcaa cttccctacg acgaatggcc cgtgggcgac aggtgatggc      1860
gtgaaacttg cacagcgact tggcgctcaa ctggtggata tggacaaggt ccagttgcat      1920
ccgacaggcc tcatcaaccc gaaggatcca gcgaacccta caaagttcct tggacctgag      1980
gcgctacgtg gatccggtgg cgttttgttg aacaagcaag gcaagcgctt cgttaatgaa      2040
cttgacctcc gttctgtggt atcgaaagcc atcatggaac agggtgcgga atatcctgga      2100
tcgggtggta gcatgttcgc ctactgtgtg ttgaatgctg cggcgcagaa gctctttggt      2160
gtcagctcac acgagttcta ctggaagaag atgggtctct tcgtgaaggc tgacaccatg      2220
agggacctcg ctgcactcat tgggtgccca gtggaatctg tgcagcagac gctggaggag      2280
tacgagcggc tctccatatc acagcgttcc tgccccatca cgcgcaaaag cgtctatccg      2340
tgcgtgctcg gcactaaggg cccctactac gtcgccttcg tgacaccttc gattcactac      2400
acaatgggtg gatgtctcat ctcgccttct gctgaaatac aaatgaagaa cacatcatca      2460
cgcgctccac tgagtcacag caacccaatc ctcgggttat ttggtgccgg tgaggtaacg      2520
ggtggtgtgc acggtgggaa ccggttgggc ggcaattcgc tgcttgagtg cgtcgtgttt      2580
gggagaattg cgggtgatcg ggcctcgacc atccttcaga ggaagtcctc agcactttcc      2640
ttcaaggtgt ggacgaccgt ggtgctgcgt gaagtacgcg aaggtggtgt gtacggtgct      2700
gggtcccgcg tgcttcgctt taatttaccc ggggcgctgc aacggtctgg tctgagcctc      2760
ggccaattta tcgcaattcg tggtgattgg gacggtcagc agttgatcgg ttattacagt      2820
cccatcacgc tgccagatga tcttggcatg atcgatatac tcgcccgcag tgataagggg      2880
acgctgaggg agtggatttc cgctctggag ccgggtgacg ctgtggagat gaaggcatgc      2940
ggtggtctgg tgattgagcg ccgcttaagc gataagcact ttgtgttcat gggacacatt      3000
atcaacaagc tttgtctaat tgctggtgga acgggtgtgg caccgatgct gcaaataatc      3060
aaagcagcct ttatgaaacc cttccattga cattggaga gcgttcatct catctatgcc       3120
gcggaggacg tgacggagtt gacgtatcgc gaggtgctgg aggagcgccg tcgtgagtca      3180
cgtggaaagt tcaagaaaac gtttgtcctc aaccggcccc cgcccctatg gactgatggt      3240
gttggcttca tcgaccgggg catcctcaca aatcatgtgc agccgccatc tgacaacctg      3300
ctggtggcca tatgcggacc accggtaatg cagcgcattg taaaggcgac cctgaagact      3360
ttgggctaca acatgaacct tgtgaggact gtggatgaaa cggagccgag cggctcatcc      3420
aaaatttga                                                              3429

<210> SEQ ID NO 6
<211> LENGTH: 1139
<212> TYPE: PRT
<213> ORGANISM: Artificial sequence
<220> FEATURE:
<223> OTHER INFORMATION: FRDg lacking 3 aa C-terminal targeting signal
```

<400> SEQUENCE: 6

Met Val Asp Gly Arg Ser Ala Ser Ile Val Ala Val Asp Pro Glu
1               5                   10                  15

Arg Ala Ala Arg Glu Arg Asp Ala Ala Ala Arg Ala Leu Leu Gln Asp
            20                  25                  30

Ser Pro Leu His Thr Thr Met Gln Tyr Ala Thr Ser Gly Leu Glu Leu
            35                  40                  45

Thr Val Pro Tyr Ala Leu Lys Val Val Ala Ser Ala Asp Thr Phe Asp
    50                  55                  60

Arg Ala Lys Glu Val Ala Asp Glu Val Leu Arg Cys Ala Trp Gln Leu
65                  70                  75                  80

Ala Asp Thr Val Leu Asn Ser Phe Asn Pro Asn Ser Glu Val Ser Leu
                85                  90                  95

Val Gly Arg Leu Pro Val Gly Gln Lys His Gln Met Ser Ala Pro Leu
            100                 105                 110

Lys Arg Val Met Ala Cys Cys Gln Arg Val Tyr Asn Ser Ser Ala Gly
            115                 120                 125

Cys Phe Asp Pro Ser Thr Ala Pro Val Ala Lys Ala Leu Arg Glu Ile
130                 135                 140

Ala Leu Gly Lys Glu Arg Asn Asn Ala Cys Leu Glu Ala Leu Thr Gln
145                 150                 155                 160

Ala Cys Thr Leu Pro Asn Ser Phe Val Ile Asp Phe Glu Ala Gly Thr
                165                 170                 175

Ile Ser Arg Lys His Glu His Ala Ser Leu Asp Leu Gly Gly Val Ser
            180                 185                 190

Lys Gly Tyr Ile Val Asp Tyr Val Ile Asp Asn Ile Asn Ala Ala Gly
            195                 200                 205

Phe Gln Asn Val Phe Phe Asp Trp Gly Gly Asp Cys Arg Ala Ser Gly
210                 215                 220

Met Asn Ala Arg Asn Thr Pro Trp Val Val Gly Ile Thr Arg Pro Pro
225                 230                 235                 240

Ser Leu Asp Met Leu Pro Asn Pro Pro Lys Glu Ala Ser Tyr Ile Ser
                245                 250                 255

Val Ile Ser Leu Asp Asn Glu Ala Leu Ala Thr Ser Gly Asp Tyr Glu
            260                 265                 270

Asn Leu Ile Tyr Thr Ala Asp Asp Lys Pro Leu Thr Cys Thr Tyr Asp
            275                 280                 285

Trp Lys Gly Lys Glu Leu Met Lys Pro Ser Gln Ser Asn Ile Ala Gln
290                 295                 300

Val Ser Val Lys Cys Tyr Ser Ala Met Tyr Ala Asp Ala Leu Ala Thr
305                 310                 315                 320

Ala Cys Phe Ile Lys Arg Asp Pro Ala Lys Val Arg Gln Leu Leu Asp
                325                 330                 335

Gly Trp Arg Tyr Val Arg Asp Thr Val Arg Asp Tyr Val Tyr Val
            340                 345                 350

Arg Glu Asn Glu Arg Val Ala Lys Met Phe Glu Ile Ala Thr Glu Asp
            355                 360                 365

Ala Glu Met Arg Lys Arg Ile Ser Asn Thr Leu Pro Ala Arg Val
            370                 375                 380

Ile Val Val Gly Gly Gly Leu Ala Gly Leu Ser Ala Ala Ile Glu Ala
385                 390                 395                 400

Ala Gly Cys Gly Ala Gln Val Val Leu Met Glu Lys Glu Ala Lys Leu

```
            405                 410                 415
Gly Gly Asn Ser Ala Lys Ala Thr Ser Gly Ile Asn Gly Trp Gly Thr
            420                 425                 430

Arg Ala Gln Ala Lys Ala Ser Ile Val Asp Gly Gly Lys Tyr Phe Glu
            435                 440                 445

Arg Asp Thr Tyr Lys Ser Gly Ile Gly Gly Asn Thr Asp Pro Ala Leu
            450                 455                 460

Val Lys Thr Leu Ser Met Lys Ser Ala Asp Ala Ile Gly Trp Leu Thr
465                 470                 475                 480

Ser Leu Gly Val Pro Leu Thr Val Leu Ser Gln Leu Gly Gly His Ser
            485                 490                 495

Arg Lys Arg Thr His Arg Ala Pro Asp Lys Lys Asp Gly Thr Pro Leu
            500                 505                 510

Pro Ile Gly Phe Thr Ile Met Lys Thr Leu Glu Asp His Val Arg Gly
            515                 520                 525

Asn Leu Ser Gly Arg Ile Thr Ile Met Glu Asn Cys Ser Val Thr Ser
            530                 535                 540

Leu Leu Ser Glu Thr Lys Glu Arg Pro Asp Gly Thr Lys Gln Ile Arg
545                 550                 555                 560

Val Thr Gly Val Glu Phe Thr Gln Ala Gly Ser Lys Thr Thr Ile
                    565                 570                 575

Leu Ala Asp Ala Val Ile Leu Ala Thr Gly Gly Phe Ser Asn Asp Lys
                    580                 585                 590

Thr Ala Asp Ser Leu Leu Arg Glu His Ala Pro His Leu Val Asn Phe
            595                 600                 605

Pro Thr Thr Asn Gly Pro Trp Ala Thr Gly Asp Gly Val Lys Leu Ala
            610                 615                 620

Gln Arg Leu Gly Ala Gln Leu Val Asp Met Asp Lys Val Gln Leu His
625                 630                 635                 640

Pro Thr Gly Leu Ile Asn Pro Lys Asp Pro Ala Asn Pro Thr Lys Phe
                    645                 650                 655

Leu Gly Pro Glu Ala Leu Arg Gly Ser Gly Gly Val Leu Leu Asn Lys
            660                 665                 670

Gln Gly Lys Arg Phe Val Asn Glu Leu Asp Leu Arg Ser Val Val Ser
            675                 680                 685

Lys Ala Ile Met Glu Gln Gly Ala Glu Tyr Pro Gly Ser Gly Gly Ser
            690                 695                 700

Met Phe Ala Tyr Cys Val Leu Asn Ala Ala Gln Lys Leu Phe Gly
705                 710                 715                 720

Val Ser Ser His Glu Phe Tyr Trp Lys Lys Met Gly Leu Phe Val Lys
                    725                 730                 735

Ala Asp Thr Met Arg Asp Leu Ala Ala Leu Ile Gly Cys Pro Val Glu
            740                 745                 750

Ser Val Gln Gln Thr Leu Glu Glu Tyr Glu Arg Leu Ser Ile Ser Gln
            755                 760                 765

Arg Ser Cys Pro Ile Thr Arg Lys Ser Val Tyr Pro Cys Val Leu Gly
            770                 775                 780

Thr Lys Gly Pro Tyr Tyr Val Ala Phe Val Thr Pro Ser Ile His Tyr
785                 790                 795                 800

Thr Met Gly Gly Cys Leu Ile Ser Pro Ser Ala Glu Ile Gln Met Lys
                    805                 810                 815

Asn Thr Ser Ser Arg Ala Pro Leu Ser His Ser Asn Pro Ile Leu Gly
            820                 825                 830
```

Leu Phe Gly Ala Gly Glu Val Thr Gly Gly Val His Gly Gly Asn Arg
            835                 840                 845

Leu Gly Gly Asn Ser Leu Leu Glu Cys Val Val Phe Gly Arg Ile Ala
        850                 855                 860

Gly Asp Arg Ala Ser Thr Ile Leu Gln Arg Lys Ser Ser Ala Leu Ser
865                 870                 875                 880

Phe Lys Val Trp Thr Thr Val Leu Arg Glu Val Arg Glu Gly Gly
                885                 890                 895

Val Tyr Gly Ala Gly Ser Arg Val Leu Arg Phe Asn Leu Pro Gly Ala
            900                 905                 910

Leu Gln Arg Ser Gly Leu Ser Leu Gly Gln Phe Ile Ala Ile Arg Gly
            915                 920                 925

Asp Trp Asp Gly Gln Gln Leu Ile Gly Tyr Tyr Ser Pro Ile Thr Leu
            930                 935                 940

Pro Asp Asp Leu Gly Met Ile Asp Ile Leu Ala Arg Ser Asp Lys Gly
945                 950                 955                 960

Thr Leu Arg Glu Trp Ile Ser Ala Leu Glu Pro Gly Asp Ala Val Glu
                965                 970                 975

Met Lys Ala Cys Gly Leu Val Ile Glu Arg Arg Leu Ser Asp Lys
            980                 985                 990

His Phe Val Phe Met Gly His Ile Ile Asn Lys Leu Cys Leu Ile Ala
            995                 1000                1005

Gly Gly Thr Gly Val Ala Pro Met Leu Gln Ile Ile Lys Ala Ala
        1010                1015                1020

Phe Met Lys Pro Phe Ile Asp Thr Leu Glu Ser Val His Leu Ile
        1025                1030                1035

Tyr Ala Ala Glu Asp Val Thr Glu Leu Thr Tyr Arg Glu Val Leu
        1040                1045                1050

Glu Glu Arg Arg Arg Glu Ser Arg Gly Lys Phe Lys Lys Thr Phe
        1055                1060                1065

Val Leu Asn Arg Pro Pro Leu Trp Thr Asp Gly Val Gly Phe
        1070                1075                1080

Ile Asp Arg Gly Ile Leu Thr Asn His Val Gln Pro Pro Ser Asp
        1085                1090                1095

Asn Leu Leu Val Ala Ile Cys Gly Pro Pro Val Met Gln Arg Ile
        1100                1105                1110

Val Lys Ala Thr Leu Lys Thr Leu Gly Tyr Asn Met Asn Leu Val
        1115                1120                1125

Arg Thr Val Asp Glu Thr Glu Pro Ser Gly Ser
        1130                1135

```
<210> SEQ ID NO 7
<211> LENGTH: 3498
<212> TYPE: DNA
<213> ORGANISM: Artificial sequence
<220> FEATURE:
<223> OTHER INFORMATION: FRDm1 codon optimised for A. niger

<400> SEQUENCE: 7
atgggtgccg atggtatctc ctctgcctcc attgtcgtca ccgaccccga ggctgctgcc      60
aagaagcgtg accgcatggc ccgtgagctc ctctcctcca actccggtct tgccaggag      120 gatgagccca ccatcatcaa cctgaagggt ctggaacaca ccatccccta ccgtcttgct     180
gttgtccttt gcaactctcg cagcactggt gaattcgagg ccaaggctgc tgagatcctc     240
```

-continued

| | | |
|---|---|---|
| cgcaaggctt tccacatggt tgactactct ctgaactgct tcaaccccga gtccgagctc | 300 | |
| tcccgtgtca acagcttgcc tgtcggtgag aagcaccaga tgagcgaaga tctgcgccac | 360 | |
| gtcatggagt gcaccatctc cgtccaccac tcctctggca tgggtttcga ccctgctgct | 420 | |
| ggtcccatca tctcccgtct gcgtggtgcc atgcgcgacc acaacgacat gtccgacatc | 480 | |
| tccgtcaccg aggctgaggt tgagctgttc tcgctagcgc agtcgttcga tgttgacctc | 540 | |
| gaggagggca ccattgctcg caagcactcc gaggctcgcc tcgaccttgg tggtgtcaac | 600 | |
| aagggctaca ctgttgacta cgtggtggac cacctccgcg ctgctggcat gcccaacgtc | 660 | |
| ctgttcgaat ggggtggtga catccgtgcc tccggccgca acatcaaggg caacctctgg | 720 | |
| gctgttgcca tcaagcgccc tccctccgtt gaggaggtca tccgccgtgc caagggcaag | 780 | |
| atgctcaaga tgggtgaaga agaacaggag gagaaggatg atgactctcc cagccttctg | 840 | |
| cacgttgttg agctcgatga tgaggccctc tgcacctccg tgactacgga aacgtcctc | 900 | |
| taccacccca agcacggtgt tgctggcagc atcttcgact ggcagcgccg tggtctgctg | 960 | |
| tctcctgagg agggtgctct tgctcaggtt tccgtcaagt gctactctgc catgtacgcc | 1020 | |
| gatgcccttg ccaccgtctg cctggtcaag cgtgatgccg tccgtatccg ctacctcctg | 1080 | |
| gaaggctggc gctacgtgcg ctctcgtgtc accaactact tcgcctacac ccgccagggt | 1140 | |
| gagcgtcttg ctcacatgca cgaaattgcc caggagactc gtgagctccg tgagatccgc | 1200 | |
| attgctggct ccctcccctc ccgtatcgtc atcgtcggtg gtggtctggc cggtctgtct | 1260 | |
| gctgccattg aggctgcctc ctgcggtgct caggtcatcc tgatggagaa ggagggtcgt | 1320 | |
| attggtggca actctgccaa ggccacctcc ggtatcaacg gctggggtac tcgcactcag | 1380 | |
| gccaagtccg acatcctgga tggcggcaag tacttcgagc gtgacacctt cctgagcggt | 1440 | |
| gttggtggta ccactgaccc tgctctggtc aaggtcctct ccgtcaagtc cggtgatgcc | 1500 | |
| attggctggt tgaccagcct tggtgttcct cttctgttc tctcccagct gggtggtcac | 1560 | |
| tctttcaagc gtaccaccg tgctcctgac aagactgatg gcactcctct ccccatcggt | 1620 | |
| cacaccatca tgcgcaccct cgaggaccac atccgcaaca acctgagcga acgtgtcacc | 1680 | |
| atcatgaccc acgtttccgt cactgagctc ctccacgaga ctgacaccac tcccgatggt | 1740 | |
| gcctccgagg tccgtgtcac cggtgtccgc taccgtgacc tctccgatgt tgacggccag | 1800 | |
| cccagcaagc tccttgccga tgccgttgtc cttgccactg gtggtttctc caacgaccgc | 1860 | |
| gaggagaaca gcttgctttg caagtacgcc ccccacctgg cctccttccc caccaccaac | 1920 | |
| ggcccttggg ccactggtga tggtgtcaag ctggccaccct ccgtcggtgc caagctcgtc | 1980 | |
| gacatggaca aggtccagct gcaccccact ggcttgattg accccaagga ccccgccaac | 2040 | |
| accaccaaga tcctgggccc cgaggctctc cgtggcagcg gtggtatcct gctcaacaag | 2100 | |
| cagggcaagc gcttcgtcaa cgagcttgac ctccgcagcg ttgtctccaa ggccatcaac | 2160 | |
| actcagggca acgaataccc cggcagcggt ggctgctact cgcctactg cgtgttgaac | 2220 | |
| gaagatgcca ccaacctgtt ctgcggtggt gctcttggat tctacggcaa gaagcttggt | 2280 | |
| ctgttccagc gtgctgagac tgttgaggag cttgccaagt tgattggctg cgatgagggc | 2340 | |
| gagctccgtg acaccctcga gaagtacgag acttgctcga aggccaaggt tgcctgcccc | 2400 | |
| gtgaccggca aggtcgtgtt cccctgcgtt gttggtaccc gtggtcccta caacgtcgct | 2460 | |
| ttcgtcaccc cctccatcca ctacaccatg ggtggctgct tgatttctcc tgctgctgag | 2520 | |
| gtcctccagg aatacaaggg tctgaacatc ctggagaacc accgtcccat tcgctgcttg | 2580 | |
| ttcggtgctg gtgaagtcac cggtggtgtc cacggtggca accgcctggg tggcaactcc | 2640 | |

```
ctcctcgagt gcgttgtgtt cggcaagatc gctggtgacc gtgctgccac cattctccag    2700
aagcgcgaaa ttgccctctc caagaccagc tggacctccg tcgtcgtccg cgagtcccgc    2760
tctggcgagc agttcggtac cggctctcgt gtcctccgct tcaacctgcc cggtgctctc    2820
cagcgcactg tctgaacct gggtgagttc gtcgccatcc gtggtgaatg ggatggccag    2880
cagctggtcg gctacttctc ccccatcacc ctccccgaag atcttggtac catctccctc    2940
ctggtccgtg ccgacaaggg caccctcaag gaatggatat gtgccctccg ccccggtgac    3000
agcgttgaga tcaaggcctg cggtggtctg cgtatcgacc aggaccctgt caagaagtgc    3060
ttgctattcc gcaaccgccc catcacccgc ttcgctcttg ttgctgctgg tactggtgtt    3120
gctcccatgc tccaggtcat ccgtgctgct ctcaagaagc cctacgtgga tacattggag    3180
tccatccgtc tgatctacgc tgctgaagaa tacgacaccc tgacctaccg ctccatcctc    3240
cagcgcttcg ctgaggagtt ccccgacaag ttcgtctgca acttcgtcct caacaaccct    3300
cctgaaggct ggactggtgg tgttggtttc gtcaacaaga gtccctcca gaaggtcctc    3360 cagcctccta gctctgagcc tctgattgtc gtctgcggtc ctcctgtcat gcagcgtgat    3420
gtcaagaacg agctcctcag catgggctac gacaaggagc ttgtccacac cgttgacggc    3480
gagtctggca ccctataa                                                 3498
```

<210> SEQ ID NO 8
<211> LENGTH: 3420
<212> TYPE: DNA
<213> ORGANISM: Artificial sequence
<220> FEATURE:
<223> OTHER INFORMATION: FRDg gene optimised for A. niger

<400> SEQUENCE: 8

```
atggtcgatg gccgctcctc cgcctccatt gttgctgttg accccgagcg tgctgctcgt      60
gagcgtgatg ctgctgctcg tgccctcctc caggactctc ccttgcacac caccatgcag     120
tacgccacct ccggtctgga attgactgtt ccctacgccc tcaaggttgt tgcctccgcc     180
gacaccttcg accgtgccaa ggaggttgcc gatgaggtcc tccgctgcgc ctggcagctg     240
gccgacaccg tcctcaactc tttcaacccc aacagcgaag tctctctggt cggccgcctc     300
cccgtcggtc agaagcacca gatgagcgcc cctctcaagc gtgtcatggc ctgctgccag     360
cgtgtctaca cagctctgc tggctgcttc gaccccagca ctgctcctgt tgccaaggcc     420
ctccgtgaga tcgctcttgg caaggagcgc aacaacgcct gcttggaggc tcttactcag     480
gcctgcaccc tccccaactc gttcgtcatt gacttcgagg ctggcaccat ctcccgcaag     540
cacgaacacg cctccctcga tcttggtggt gtcagcaagg gctacatcgt cgactacgtc     600
attgacaaca tcaacgctgc tggtttccag aacgttttct tcgactgggg tggtgactgc     660
cgtgcctccg gcatgaacgc ccgcaacacc ccctgggttg ttggtatcac ccgcccccg     720 tcattggaca tgcttcccaa ccctcccaag gaggccagct acatctccgt catctccctc    780
gacaacgagg ctcttgccac cagcggtgac tacgagaacc tgatctacac tgccgatgac    840
aagcctctga cctgcaccta cgactggaag ggcaaggagc tcatgaagcc cagccagtcc    900
aacattgccc aggtcagcgt caagtgctac tctgccatgt acgccgatgc ccttgccact    960
gcttgcttca tcaagcgtga ccccgccaag gtccgccagc tgttggatgg ctggcgctac   1020
gtgcgcgaca ccgtccgtga ctaccgtgtc tacgtgcgcg agaacgagcg tgttgccaag   1080
atgttcgaaa ttgccactga ggatgccgag atgcgcaagc gccgtatctc caacaccctc   1140
```

```
cctgctcgtg tcattgttgt tggtggtggt ctggctggtc tttctgctgc cattgaggct    1200
gctggctgcg gtgctcaggt tgtcctgatg gagaaggagg ccaagctcgg tggcaactcc    1260
gccaaggcca cctccggtat caacggctgg ggtactcgtg ctcaggccaa ggcctccatc    1320
gtcgatggcg gcaagtactt cgagcgtgac acctacaagt ccggtatcgg tggcaacacc    1380
gaccctgctc tggtcaagac cctgagcatg aagtccgccg atgccattgg ctggttgacc    1440
agccttggtt tcctcttac tgtcctttct cagctgggtg gccactctcg caagcgcacc    1500
caccgtgctc ctgacaagaa ggacggcacc cccctcccca tcggtttcac catcatgaaa    1560
actctcgagg accacgtccg tggcaacctg tctggccgta tcaccatcat ggagaactgc    1620
tcggtgacct cgctactctc cgagactaag gagcgccccg atggcaccaa gcagatccgt    1680
gtcaccggtg ttgagttcac ccaggctggc tctggcaaga ccaccatcct ggccgatgcc    1740
gtcatcctgg ccactggtgg tttctccaac gacaagactg ccgactcgct actccgcgaa    1800
cacgctcccc acctggtcaa cttccccacc accaacggcc cctgggcgac tggtgatggt    1860
gtcaagctgg cccagcgtct gggtgctcag ctcgtcgaca tggacaaggt ccagctccac    1920
cccactggtc tgatcaaccc caaggaccct gccaaccccc a ccaagttcct tggacctgag    1980
gctctccgtg gctccggtgg tgtccttctg aacaagcagg gcaagcgctt cgtcaacgag    2040
ctcgatctcc gcagcgttgt ctccaaggcc atcatggagc agggtgctga ataccccggc    2100
agcggtggca gcatgttcgc ctactgcgtt ctcaacgctg ctgctcagaa gctgttcggt    2160
gtctcctccc acgaattcta ctggaagaag atgggtctgt tcgtcaaggc cgacaccatg    2220
cgtgatcttg ctgctctgat cggttgcccc gttgagagcg tgcagcagac cctggaagaa    2280
tacgagcgcc tctccatctc ccagcgctct tgccccatca cccgcaagtc ggtgtaccct    2340
tgcgtgcttg gcaccaaggg tccctactac gtggctttcg tcacccctc catccactac    2400 accatgggtg gctgcttgat ctctccttct gctgagatcc agatgaagaa cacctcctcc    2460
cgtgctcctc tctcccactc caaccccatc ctcggtctgt tcggtgctgg tgaagtcact    2520
ggtggtgtcc acggtggcaa ccgtcttggt ggcaactccc tcctcgagtg cgttgtgttc    2580
ggccgtatcg ctggtgaccg tgccagcacc atcctccagc gcaagagctc tgctctctcc    2640
ttcaaggtct ggaccactgt tgtcctccgc gaagtccgcg agggtggtgt ctacggtgct    2700
ggctctcgtg tcctccgctt caacctcccc ggtgctctcc agcgctccgg tctgtctctt    2760
ggccagttca ttgccatccg tggtgactgg gatggccagc agctcattgg ctactactct    2820
cccatcaccc tccccgatga tcttggaatg atcgacatcc tggctcgctc cgacaagggt    2880
accctccgcg aatggatctc cgctctggag cccggtgatg ccgttgagat gaaggcctgc    2940
ggtggtctgg tcattgagcg tcgtctgtcc gacaagcact tcgtgttcat gggtcacatc    3000
atcaacaagc tctgcttgat tgccggtggt actggtgttg ctcccatgct tcagatcatc    3060
aaggctgctt tcatgaagcc cttcattgac accctcgagt ccgtccacct gatctacgct    3120
gctgaggatg tcactgagct gacctaccgt gaggtccttg aggagcgccg ccgcgagtcc    3180
cgtggcaagt tcaagaaaac cttcgtcctg aaccgccctc ctcctctctg gactgatggt    3240
gttggtttca ttgaccgtgg tatcctgacc aaccacgtcc agcctccctc cgacaaccta    3300
ttagtggcca tctgcggtcc tcctgtcatg cagcgcattg tcaaggccac tctcaagacc    3360
ctaggataca acatgaacct ggtccgcact gttgatgaga ctgagccctc cggatcataa    3420
```

<210> SEQ ID NO 9
<211> LENGTH: 3498

<210> TYPE: DNA
<213> ORGANISM: Artificial sequence
<220> FEATURE:
<223> OTHER INFORMATION: FRDm1 gene optimsied for S. cerevisiae

<400> SEQUENCE: 9

```
atgggtgctg atggtatttc ttctgcttcc attgttgtta ctgacccaga agctgctgcc      60
aagaagcgtg acagaatggc cagagaattg ttgtcctcca actctggtct atgtcaagaa     120
gatgaaccaa ccatcatcaa cttaaagggt ttggaacaca ccattccata cagattggcc     180
gttgttttgt gtaactccag atccactggt gaattcgaag ccaaggctgc tgaaatcttg     240
agaaggcttt ccacatggtt tgactactct ttgaattgtt caacccagat ctgaattg      300
tcccgtgtca actctttacc agtcggtgaa aagcaccaaa tgtccgaaga tctaagacat     360
gtcatggaat gtaccatttc tgtccaccac tcctctggta tgggtttcga cccagctgct     420
ggtccaatca tctccagatt gagaggtgcc atgagagatc acaacgacat gtccgatatc     480
tccgtcactg aagctgaagt tgaattattc tctttggctc aatctttcga gtcgacttg      540
gaagaaggta ctattgccag aaagcactct gaagccagat tggatttggg tggtgtcaac     600
aagggttaca ctgttgacta cgttgttgac catttgagag ctgctggtat gccaaacgtc     660
ttgttcgaat ggggtggtga tatcagagct tctggtagaa acatcaaggg taacttgtgg     720
gctgttgcca tcaagcgtcc accatctgtt gaagaagtta ccgtcgtgc caagggtaag     780
atgttaaaga tgggtgaaga agaacaagaa gaaaaggacg atgactctcc atctttgttg     840
cacgttgttg aattggatga cgaagctttg tgtacctctg gtgactacga aaacgtctta     900
taccatccaa agcacggtgt tgctggttcc attttcgact ggcaacgtcg tggtttattg     960
tctccagaag aaggtgcttt agctcaagtt tccgtcaaat gttactctgc catgtacgct    1020
gatgctttgg ccactgtttg tttggtcaag agagatgctg tcagaatcag atacttgttg    1080
gaaggttgga tacgtcag atctcgtgtc ccaactact tcgcttacac cagacaaggt     1140
gaaagattgg ctcacatgca cgaaattgct caagaaacca gagaattaag agaaatcaga    1200
attgctggtt ctttgccatc cagaattgtt atcgtcggtg gtggtttggc tggtctatcc    1260
gctgccattg aagctgcttc ttgtggtgct caagtcattt tgatggaaaa ggaaggtaga    1320
attggtggta ctctgccaa ggctacctct ggtatcaacg ttggggtac cagaacccaa     1380
gccaagtctg atatcttgga tggtggtaag tactttgaaa agagacactt cttgtccggt    1440
gtcggtggta ccactgaccc agctttggtc aaggtcttgt ccgtcaaatc tggtgacgct    1500
atcggttggt taacttcttt gggtgtccca ttgtccgttt tgtctcaatt gggtggtcac    1560
tcttcaaga gaactcacag agctccagac aagactgatg gtactccatt accaattggt    1620
cacaccatca tgagaacttt ggaagatcat atcagaaaca cttgtctga agagttacc     1680
atcatgaccc acgttctgt tactgaattg ttgcacgaaa ctgacaccac tccagatggt    1740
gcttctgaag ttcgtgtcac cggtgtccgt tacagagact gtctgatgt cgatggtcaa    1800
ccttccaaac tattggctga cgctgttgtt ttggccactg gtggtttctc aacgacaga    1860
gaagaaaact ctttgttgtg taaatacgct cctcatttgg cttctttccc aactaccaac    1920
ggtccatggg ctactggtga cggtgtcaaa ttggccacct ccgttggtgc aagttggtt    1980
gacatggaca aggttcaatt gcacccaact ggtttgattg acccaaagga cccagctaac    2040
accactaaga tcttgggtcc agaagctttg agaggtctg gtggtatttt gttgaacaag    2100
caaggtaaga gattcgtcaa cgaattggac ttgagatccg ttgtttccaa ggccattaac    2160
```

```
actcaaggta acgaataccc aggttctggt ggttgttact ttgcttactg tgtcttaaac    2220
gaagatgcta ccaacttatt ctgtggtggt gctttgggtt tctacggtaa gaaattaggt    2280
ttgttccaaa gagctgaaac tgttgaagaa ttggccaaat tgattggttg tgacgaaggt    2340
gaattgagag acactttgga aaaatacgaa acctgttcca aggccaaggt tgcttgtcca    2400
gtcactggta aggttgtttt cccatgtgtt gtcggtacca gaggtccata caatgttgct    2460
ttcgtcactc catccatcca ctacaccatg ggtggttgtt tgatctctcc agctgctgaa    2520
gtcttgcaag aatacaaggg tttgaatatc ttggaaaacc acagaccaat cagatgtttg    2580
ttcggtgctg gtgaagtcac tggtggtgtc cacggtggta acagattagg tggtaactct    2640
ctattggaat gtgttgtctt tggtaagatt gctggtgaca gagctgccac tatcttgcaa    2700
aagagagaaa ttgctttgtc caagacctcc tggacctctg ttgttgtcag agaatccaga    2760
tctggtgaac aattcggtac cggttccaga gttttgagat tcaacttgcc aggtgcttta    2820
caaagaaccg gtttgaactt gggtgaattc gttgccatca gaggtgaatg ggatggtcaa    2880
caattagtcg gttacttctc tccaatcact ttgccagaag atttgggtac catctctttg    2940
ttggtcagag ctgacaaggg tactttgaag gaatggatct gtgctttgcg tccaggtgac    3000
tccgttgaaa tcaaggcttg tggtggtcta agaattgacc aagatccagt caagaaatgt    3060
ttgttgttca gaaacagacc aattaccaga tttgctttgg ttgctgctgg taccggtgtt    3120
gctccaatgt tgcaagttat cagagctgct ttgaagaagc atacgtcga cactttggaa    3180
tccatcagat tgatctacgc tgctgaagaa tatgacactt taacctacag atctatcttg    3240
caaagatttg ctgaagaatt cccagacaaa ttcgtttgta acttcgtctt aaacaaccct    3300
ccagaaggtt ggaccggtgg tgttggtttc gtcaacaaga aatctttgca aaaggttttg    3360
caaccacctt cttctgaacc attgattgtt gtttgtggtc cacctgttat gcaaagagat    3420
gtcaaaaatg aattgttgtc catgggttac gacaaggaat tggttcacac tgtcgatggt    3480
gaatctggta ccttgtaa                                                  3498

<210> SEQ ID NO 10
<211> LENGTH: 3420
<212> TYPE: DNA
<213> ORGANISM: Artificial sequence
<220> FEATURE:
<223> OTHER INFORMATION: FRDg gene optimised for S. cerevisiae

<400> SEQUENCE: 10
atggttgatg gtagatcttc tgcttccatt gttgccgttg acccagaaag agctgccaga      60
gaaagagatg ctgctgccag agctttgttg caagactctc cattgcacac caccatgcaa     120
tacgctacct ctggtttgga attgactgtt ccatacgctt tgaaggttgt tgcttctgct     180
gacactttcg acagagccaa ggaagttgct gatgaagtct tgagatgtgc ctggcaattg     240
gctgacaccg ttttgaactc tttcaaccca aactctgaag tctctttagt cggtagatta     300
ccagtcggtc aaaagcatca aatgtctgct ccattgaaac gtgtcatggc ttgttgtcaa     360
agagtctaca actcctctgc tggttgtttc gacccatcca ctgctccagt gccaaggct     420
ttgagagaaa ttgctttggg taaggaaaga acaatgcttg tttggaagc tttgactcaa     480
gcttgtacct tgccaaactc tttcgtcatt gatttcgaag ctggtactat ctccagaaag     540
cacgaacacg cttctttgga tttgggtggt gtttccaagg ttacatcgt cgattacgtc     600
attgacaaca tcaatgctgc tggtttccaa acgttttct ttgactgggg tggtgactgt     660
cgtgcctccg gtatgaacgc cagaaacact ccatgggttg tcggtatcac tagacctcct     720
```

-continued

```
tccttggaca tgttgccaaa ccctccaaag gaagcttctt acatctccgt catctctttg    780
gacaatgaag ctttggctac ctctggtgat tacgaaaact tgatctacac tgctgacgat    840
aaaccattga cctgtaccta cgattggaaa ggtaaggaat tgatgaagcc atctcaatcc    900
aatatcgctc aagtttccgt caagtgttac tctgccatgt acgctgacgc tttggctacc    960
gcttgtttca tcaagcgtga cccagccaag gtcagacaat tgttggatgg ttggagatac   1020
gttagagaca ccgtcagaga ttaccgtgtc tacgtcagag aaaacgaaag agttgccaag   1080
atgttcgaaa ttgccactga agatgctgaa atgagaaaga aagaatttc caacactta   1140
ccagctcgtg tcattgttgt tggtggtggt ttggctggtt tgtccgctgc cattgaagct   1200
gctggttgtg gtgctcaagt tgttttgatg gaaaaggaag ccaagttggg tggtaactct   1260
gccaaggcta cctctggtat caacggttgg ggtactagag ctcaagctaa ggcttccatt   1320
gtcgatggtg gtaagtactt cgaaagagat acctacaagt ctggtatcgg tggtaacacc   1380
gatccagctt tggttaagac tttgtccatg aaatctgctg acgctatcgg ttggttgact   1440
tctctaggtg ttccattgac tgttttgtcc caattaggtg gtcactccag aaagagaact   1500
cacagagctc cagacaagaa ggatggtact ccattgccaa ttggtttcac catcatgaaa   1560
actttagaag atcatgttag aggtaacttg tccggtagaa tcaccatcat ggaaaactgt   1620
tccgttacct ctttgttgtc tgaaaccaag gaaagaccag acggtaccaa gcaaatcaga   1680
gttaccggtg tcgaattcac tcaagctggt tctggtaaga ccaccatttt ggctgatgct   1740
gttatcttgg ccaccggtgg tttctccaac gacaagactg ctgattcttt gttgagagaa   1800
catgccccac acttggttaa cttcccaacc accaacggtc catgggctac tggtgatggt   1860
gtcaagttgg ctcaaagatt aggtgctcaa ttggtcgata tggacaaggt tcaattgcac   1920
ccaactggtt tgatcaaccc aaaggaccca gccaacccaa ccaaattctt gggtccagaa   1980
gctctaagag gttctggtgg tgttttgttg aacaaacaag gtaagagatt tgtcaacgaa   2040
ttggatttga gatctgttgt ttccaaggcc atcatggaac aaggtgctga atacccaggt   2100
tctggtggtt ccatgtttgc ttactgtgtc ttgaacgctg ctgctcaaaa attgtttggt   2160
gtttcctctc acgaattcta ctggaagaag atgggtttgt tcgtcaaggc tgacaccatg   2220
agagacttgg ctgctttgat tggttgtcca gttgaatccg ttcaacaaac tttagaagaa   2280
tacgaaagat tatccatctc tcaaagatct tgtccaatta ccagaaaatc tgtttaccca   2340
tgtgttttgg gtaccaaagg tccatactat gtcgcctttg tcactccatc tatccactac   2400
accatgggtg gttgttgat ttctccatct gctgaaatcc aaatgaagaa cacttcttcc   2460
agagctccat tgtcccactc caacccaatc ttgggtttat tcggtgctgg tgaagtcacc   2520
ggtggtgtcc acggtggtaa cagattaggt ggtaactctt tgttgaaatg tgttgttttc   2580
ggtagaattg ccggtgacag agcttctacc attttgcaaa gaaagtcctc tgctttgtct   2640
ttcaaggtct ggaccactgt tgttttgaga gaagtcagag aaggtggtgt ctacggtgct   2700
ggttcccgtg tcttgagatt caacttacca ggtgctctac aaagatctgg tctatccttg   2760
ggtcaattca ttgccatcag aggtgactgg gacggtcaac aattgattgg ttactactct   2820
ccaatcactt tgccagacga tttgggtatg attgacattt tggccagatc tgacaagggt   2880
actttacgtg aatggatctc tgctttggaa ccaggtgacg ctgtcgaaat gaaggcttgt   2940
ggtggtttgg tcatcgaaag aagattatct gacaagcact cgttttcat gggtcacatt   3000
atcaacaagc tatgtttgat tgctggtggt accggtgttg ctccaatgtt gcaaatcatc   3060
```

| | |
|---|---|
| aaggccgctt tcatgaagcc attcatcgac actttggaat ccgtccactt gatctacgct | 3120 |
| gctgaagatg tcactgaatt gacttacaga gaagttttgg aagaacgtcg tcgtgaatcc | 3180 |
| agaggtaaat tcaagaaaac tttcgttttg aacagacctc ctccattatg gactgacggt | 3240 |
| gtcggtttca tcgaccgtgg tatcttgacc aaccacgttc aaccaccatc tgacaactta | 3300 |
| ttggttgcca tctgtggtcc accagttatg caaagaattg tcaaggccac tttaaagact | 3360 |
| ttaggttaca acatgaactt ggtcagaacc gttgacgaaa ctgaaccatc tggaagttaa | 3420 |

<210> SEQ ID NO 11
<211> LENGTH: 898
<212> TYPE: DNA
<213> ORGANISM: Artificial sequence
<220> FEATURE:
<223> OTHER INFORMATION: GPDA promotor

<400> SEQUENCE: 11

| | |
|---|---|
| tcagcgtcca attcgagctc tgtacagtga ccggtgactc tttctggcat gcggagacac | 60 |
| ggacggtcgc agagaggagg gctgagtaat aagcgcactc atgtcagctc tggcgctctg | 120 |
| aggtgcagtg gatgattatt aatccgggac cggccgcccc tccgcccga agtggaaagg | 180 |
| ctggtgtgcc cctcgttgac caagaatcta ttgcatcatc ggagaatatg gagcttcatc | 240 |
| gaatcaccgg cagtaagcga aggagaatgt gaagccaggg gtgtatagcc gtcggcgaaa | 300 |
| tagcatgcca ttaacctagg tacagaagtc caattgcttc cgatctggta aaagattcac | 360 |
| gagatagtac cttctccgaa gtaggtagag cgagtacccg gcgcgtaagc tccctaattg | 420 |
| gcccatccgg catctgtagg gcgtccaaat atcgtgcctc tcctgctttg cccggtgtat | 480 |
| gaaaccggaa aggccgctca ggagctggcc agcggcgcag accgggaaca caagctggca | 540 |
| gtcgacccat ccggtgctct gcactcgacc tgctgaggtc cctcagtccc tggtaggcag | 600 |
| cttttgccccg tctgtccgcc cggtgtgtcg gcggggttga caaggtcgtt gcgtcagtcc | 660 |
| aacatttgtt gccatatttt cctgctctcc ccaccagctg ctctttcctt ttctctttct | 720 |
| tttcccatct tcagtatatt catcttccca tccaagaacc tttatttccc ctaagtaagt | 780 |
| actttgctac atccatactc catccttccc atcccttatt cctttgaacc tttcagttcg | 840 |
| agctttccca cttcatcgca gcttgactaa cagctacccc gcttgagcca ccgtcaaa | 898 |

<210> SEQ ID NO 12
<211> LENGTH: 1000
<212> TYPE: DNA
<213> ORGANISM: Artificial sequence
<220> FEATURE:
<223> OTHER INFORMATION: TDH3 promotor

<400> SEQUENCE: 12

| | |
|---|---|
| ctatttcga ggaccttgtc accttgagcc caagagagcc aagatttaaa ttttcctatg | 60 |
| acttgatgca aattcccaaa gctaataaca tgcaagacac gtacggtcaa gaagacatat | 120 |
| ttgacctctt aacaggttca gacgcgactg cctcatcagt aagacccgtt gaaaagaact | 180 |
| tacctgaaaa aaacgaatat atactagcgt tgaatgttag cgtcaacaac aagaagttta | 240 |
| atgacgcgga ggccaaggca aaaagattcc ttgattacgt aagggagtta gaatcatttt | 300 |
| gaataaaaaa cacgcttttt cagttcgagt ttatcattat caatactgcc atttcaaaga | 360 |
| atacgtaaat aattaatagt agtgattttc ctaactttat ttagtcaaaa aattagcctt | 420 |
| ttaattctgc tgtaacccgt acatgcccaa atagggggc gggttacaca gaatatataa | 480 |
| catcgtaggt gtctgggtga acagtttatt cctggcatcc actaaatata tggagcccg | 540 |

```
cttttaagc tggcatccag aaaaaaaaag aatcccagca ccaaaatatt gttttcttca    600
ccaaccatca gttcataggt ccattctctt agcgcaactc cagagaacag ggcacaaac    660 aggcaaaaaa cgggcacaac ctcaatggag tgatgcaacc tgcctggagt aaatgatgac   720
acaaggcaat tgacccacgc atgtatctat ctcattttct tacaccttct attaccttct   780
gctctctctg atttggaaaa agctgaaaaa aaaggttgaa accagttccc tgaaattatt   840
cccctacttg actaataagt atataaagac ggtaggtatt gattgtaatt ctgtaaatct   900
atttcttaaa cttcttaaat tctacttttta tagttagtct ttttttttagt tttaaaacac   960 caagaactta gtttcgaata aacacacata aacaaacaaa                        1000
```

<210> SEQ ID NO 13
<211> LENGTH: 500
<212> TYPE: DNA
<213> ORGANISM: Artificial sequence
<220> FEATURE:
<223> OTHER INFORMATION: TDH3 terminator

<400> SEQUENCE: 13

```
gtgaatttac tttaaatctt gcatttaaat aaattttctt tttatagctt tatgacttag    60
tttcaattta tatactattt taatgacatt ttcgattcat tgattgaaag ctttgtgttt   120 ttcttgatg cgctattgca ttgttcttgt ctttttcgcc acatgtaata tctgtagtag   180
atacctgata cattgtggat gctgagtgaa attttagtta ataatggagg cgctcttaat   240 aatttttgggg atattggctt ttttttttaa agtttacaaa tgaattttttt ccgccaggat   300 aacgattctg aagttactct tagcgttcct atcggtacag ccatcaaatc atgcctataa   360
atcatgccta tatttgcgtg cagtcagtat catctcacatg aaaaaaactc ccgcaatttc   420
ttatagaata cgttgaaaat taaatgtacg cgccaagata agataacata tatctagatg   480
cagtaatata cacagattcc                                              500
```

<210> SEQ ID NO 14
<211> LENGTH: 538
<212> TYPE: PRT
<213> ORGANISM: Artificial sequence
<220> FEATURE:
<223> OTHER INFORMATION: A. succinogenes PEP carboxykinase wherein EGY
      at position 120-122 is replaced by DAF

<400> SEQUENCE: 14

```
Met Thr Asp Leu Asn Lys Leu Val Lys Glu Leu Asn Asp Leu Gly Leu
1               5                   10                  15

Thr Asp Val Lys Glu Ile Val Tyr Asn Pro Ser Tyr Glu Gln Leu Phe
            20                  25                  30

Glu Glu Glu Thr Lys Pro Gly Leu Glu Gly Phe Asp Lys Gly Thr Leu
        35                  40                  45

Thr Thr Leu Gly Ala Val Ala Val Asp Thr Gly Ile Phe Thr Gly Arg
    50                  55                  60

Ser Pro Lys Asp Lys Tyr Ile Val Cys Asp Glu Thr Thr Lys Asp Thr
65                  70                  75                  80

Val Trp Trp Asn Ser Glu Ala Ala Lys Asn Asp Asn Lys Pro Met Thr
                85                  90                  95

Gln Glu Thr Trp Lys Ser Leu Arg Glu Leu Val Ala Lys Gln Leu Ser
            100                 105                 110

Gly Lys Arg Leu Phe Val Val Asp Ala Phe Cys Gly Ala Ser Glu Lys
        115                 120                 125
```

```
His Arg Ile Gly Val Arg Met Val Thr Glu Val Ala Trp Gln Ala His
130                 135                 140
Phe Val Lys Asn Met Phe Ile Arg Pro Thr Asp Glu Glu Leu Lys Asn
145                 150                 155                 160
Phe Lys Ala Asp Phe Thr Val Leu Asn Gly Ala Lys Cys Thr Asn Pro
                    165                 170                 175
Asn Trp Lys Glu Gln Gly Leu Asn Ser Glu Asn Phe Val Ala Phe Asn
                180                 185                 190
Ile Thr Glu Gly Ile Gln Leu Ile Gly Gly Thr Trp Tyr Gly Gly Glu
            195                 200                 205
Met Lys Lys Gly Met Phe Ser Met Met Asn Tyr Phe Leu Pro Leu Lys
210                 215                 220
Gly Val Ala Ser Met His Cys Ser Ala Asn Val Gly Lys Asp Gly Asp
225                 230                 235                 240
Val Ala Ile Phe Phe Gly Leu Ser Gly Thr Gly Lys Thr Thr Leu Ser
                    245                 250                 255
Thr Asp Pro Lys Arg Gln Leu Ile Gly Asp Asp Glu His Gly Trp Asp
                260                 265                 270
Glu Ser Gly Val Phe Asn Phe Glu Gly Gly Cys Tyr Ala Lys Thr Ile
            275                 280                 285
Asn Leu Ser Gln Glu Asn Glu Pro Asp Ile Tyr Gly Ala Ile Arg Arg
290                 295                 300
Asp Ala Leu Leu Glu Asn Val Val Arg Ala Asp Gly Ser Val Asp
305                 310                 315                 320
Phe Asp Asp Gly Ser Lys Thr Glu Asn Thr Arg Val Ser Tyr Pro Ile
                    325                 330                 335
Tyr His Ile Asp Asn Ile Val Arg Pro Val Ser Lys Ala Gly His Ala
                340                 345                 350
Thr Lys Val Ile Phe Leu Thr Ala Asp Ala Phe Gly Val Leu Pro Pro
            355                 360                 365
Val Ser Lys Leu Thr Pro Glu Gln Thr Glu Tyr Tyr Phe Leu Ser Gly
370                 375                 380
Phe Thr Ala Lys Leu Ala Gly Thr Glu Arg Gly Val Thr Glu Pro Thr
385                 390                 395                 400
Pro Thr Phe Ser Ala Cys Phe Gly Ala Ala Phe Leu Ser Leu His Pro
                    405                 410                 415
Ile Gln Tyr Ala Asp Val Leu Val Glu Arg Met Lys Ala Ser Gly Ala
                420                 425                 430
Glu Ala Tyr Leu Val Asn Thr Gly Trp Asn Gly Thr Gly Lys Arg Ile
            435                 440                 445
Ser Ile Lys Asp Thr Arg Gly Ile Ile Asp Ala Ile Leu Asp Gly Ser
450                 455                 460
Ile Glu Lys Ala Glu Met Gly Glu Leu Pro Ile Phe Asn Leu Ala Ile
465                 470                 475                 480
Pro Lys Ala Leu Pro Gly Val Asp Pro Ala Ile Leu Asp Pro Arg Asp
                    485                 490                 495
Thr Tyr Ala Asp Lys Ala Gln Trp Gln Val Lys Ala Glu Asp Leu Ala
                500                 505                 510
Asn Arg Phe Val Lys Asn Phe Val Lys Tyr Thr Ala Asn Pro Glu Ala
            515                 520                 525
Ala Lys Leu Val Gly Ala Gly Pro Lys Ala
530                 535
```

<210> SEQ ID NO 15
<211> LENGTH: 1617
<212> TYPE: DNA
<213> ORGANISM: Artificial sequence
<220> FEATURE:
<223> OTHER INFORMATION: nt. A. succinogenes PEP carboxykinase encoding DAF instead of EGY

<400> SEQUENCE: 15

| | | | | | |
|---|---|---|---|---|---|
| atgactgact | taaacaaact | cgttaaagaa | cttaatgact | tagggcttac | cgatgttaag | 60 |
| gaaattgtgt | ataacccgag | ttatgaacaa | cttttcgagg | aagaaaccaa | accgggtttg | 120 |
| gagggtttcg | ataaagggac | gttaaccacg | cttggcgcgg | ttgccgtcga | tacggggatt | 180 |
| tttaccggtc | gttcaccgaa | agataaatat | atcgtttgcg | atgaaactac | gaaagacacc | 240 |
| gtttggtgga | acagcgaagc | ggcgaaaaac | gataacaaac | cgatgacgca | agaaacttgg | 300 |
| aaaagtttga | gagaattagt | ggcgaaacaa | cttttccggta | aacgtttatt | cgtggtagac | 360 |
| gcattctgcg | cgccagtga | aaaacaccgt | atcggtgtgc | gtatggttac | tgaagtggca | 420 |
| tggcaggcgc | attttgtgaa | aaacatgttt | atccgaccga | ccgatgaaga | gttgaaaaat | 480 |
| ttcaaagcgg | attttaccgt | gttaaacggt | gctaaatgta | ctaatccgaa | ctggaaagaa | 540 |
| caaggtttga | acagtgaaaa | ctttgtcgct | ttcaatatta | ccgaaggtat | tcagcttatc | 600 |
| ggcggtactt | ggtacggcgg | tgaaatgaaa | aaaggtatgt | tctcaatgat | gaactacttc | 660 |
| ctgccgttaa | aaggtgtggc | ttccatgcac | tgttccgcca | acgtaggtaa | agacggtgac | 720 |
| gtggctattt | tcttcggttt | atccggtacg | ggtaaaacaa | cgctttcgac | cgatcctaaa | 780 |
| cgccaattaa | tcggtgatga | cgaacacggt | tgggatgaat | ccggcgtatt | taactttgaa | 840 |
| ggcggttgtt | acgcgaaaac | cattaactta | tctcaagaaa | acgaaccgga | tatttacggc | 900 |
| gcaatccgtc | gtgacgcatt | attagaaaac | gtcgtggttc | gtgcagacgg | ttccgttgac | 960 |
| tttgacgacg | gttcaaaaac | agaaaatacc | cgtgtttcat | atccgattta | ccacatcgac | 1020 |
| aacatcgttc | gtccggtatc | gaaagccggt | catgcaacca | aagtgatttt | cttaaccgcg | 1080 |
| gacgcattcg | gcgtattgcc | gccggtttca | aaactgactc | cggaacaaac | cgaatactac | 1140 |
| ttcttatccg | gctttactgc | aaaattagcg | ggtacggaac | gcggcgtaac | cgaaccgact | 1200 |
| ccgacattct | cggcctgttt | cggtgcggca | ttcttaagcc | tgcatccgat | tcaatatgcg | 1260 |
| gacgtgttgg | tcgaacgcat | gaaagcctcc | ggtgcgaag | cttatttggt | gaacaccggt | 1320 |
| tggaacggca | cgggtaaacg | tatttcaatc | aaagataccc | gcggtattat | cgatgcgatt | 1380 |
| ttggacggtt | caatcgaaaa | agcggaaatg | ggcgaattgc | caatctttaa | tttagcgatt | 1440 |
| cctaaagcat | taccgggtgt | tgatcctgct | attttggatc | cgcgcgatac | ttacgcagac | 1500 |
| aaagcgcaat | ggcaagttaa | agcggaagat | ttggcaaacc | gttcgtgaa | aaactttgtg | 1560 |
| aaatatacgg | cgaatccgga | agcggctaaa | ttagttggcg | ccggtccaaa | agcataa | 1617 |

<210> SEQ ID NO 16
<211> LENGTH: 1617
<212> TYPE: DNA
<213> ORGANISM: Artificial sequence
<220> FEATURE:
<223> OTHER INFORMATION: Codon pair optimised A. succinogenes PEPCK for S. cerevisiae

<400> SEQUENCE: 16

| | | | | | |
|---|---|---|---|---|---|
| atgactgatt | tgaacaaatt | ggtcaaggaa | ttgaatgatt | tgggtttgac | tgacgtcaag | 60 |
| gaaattgtct | acaacccatc | tttacgaacaa | ttattcgaag | aagaaaccaa | gccaggtttg | 120 |

```
gaaggtttcg acaagggtac tttgaccact ttaggtgctg ttgctgttga caccggtatt    180
ttcaccggtc gttctccaaa ggacaaatac attgttgtg atgaaaccac caaggacacc    240
gtctggtgga actctgaagc tgccaagaac gataacaagc caatgactca agaaacctgg    300
aaatctttga gagaattggt tgccaagcaa ttgtctggta gagattatt cgttgttgac     360 gctttctgtg gtgcttctga aaagcacaga attggtgtca aatggtcac tgaagttgct     420 tggcaagctc atttcgtcaa gaacatgttc atcagaccaa ctgacgaaga attgaagaac    480
ttcaaggctg acttcaccgt tttgaatggt gccaagtgta ccaacccaaa ctggaaggaa    540
caaggtttga actctgaaaa ctttgttgct ttcaacatca ctgaaggtat ccaattgatt    600
ggtggtacct ggtacggtgg tgaaatgaag aagggtatgt tctccatgat gaactatttc    660
ttgccattga aggtgttgc ttccatgcac tgttctgcca atgtcggtaa ggatggtgac     720
gttgccatct tcttcggtct atccggtact ggtaagacca ctctatccac tgacccaaag    780
agacaattga ttggtgatga cgaacacggt tgggacgaat ctggtgtctt taactttgaa    840
ggtggttgtt acgccaagac catcaactta tctcaagaaa cgaaccaga tatctacggt      900 gccatccgtc gtgatgcttt gttggaaaac gttgttgtca gagctgacgg ttctgttgac    960
ttcgacgacg gttccaagac tgaaaacacc agagtttctt acccaatcta ccacattgac    1020
aacattgtca gacctgtttc aaggctggt cacgctacca aggttatctt cttgactgct     1080
gatgctttcg gtgtcttgcc acctgtttcc aaattgactc cagaacaaac cgaatactac    1140
ttcttgtccg gttcactgc caaattggct ggtactgaaa gaggtgtcac tgaaccaact     1200
ccaactttct ctgcttgttt cggtgctgct ttcttatct tgcacccaat ccaatacgct      1260
gatgtcttgg ttgaaagaat gaaggcttct ggtgctgaag cttacttggt caacaccggt    1320
tggaacggta ccggtaagag aatctccatc aaggatacca gaggtatcat tgatgctatc    1380
ttggacggtt ccattgaaaa ggctgaaatg ggtgaattgc caatcttcaa cttggccatt    1440
ccaaaggctt tgccaggtgt tgacccagcc atcttagatc aagagacac ctacgctgac    1500 aaggctcaat ggcaagtcaa ggctgaagat ttggctaaca gattcgtcaa gaactttgtc    1560
aaatacactg ctaacccaga agctgccaaa ttggttggtg ctggtccaaa ggcttaa       1617
```

<210> SEQ ID NO 17
<211> LENGTH: 538
<212> TYPE: PRT
<213> ORGANISM: Mannheimia succinicipoducens

<400> SEQUENCE: 17

Met Thr Asp Leu Asn Gln Leu Thr Gln Glu Leu Gly Ala Leu Gly Ile
1               5                   10                  15

His Asp Val Gln Glu Val Val Tyr Asn Pro Ser Tyr Glu Leu Leu Phe
            20                  25                  30

Ala Glu Glu Thr Lys Pro Gly Leu Glu Gly Tyr Glu Lys Gly Thr Val
        35                  40                  45

Thr Asn Gln Gly Ala Val Ala Val Asn Thr Gly Ile Phe Thr Gly Arg
    50                  55                  60

Ser Pro Lys Asp Lys Tyr Ile Val Leu Asp Lys Thr Lys Asp Thr
65                  70                  75                  80

Val Trp Trp Thr Ser Glu Lys Val Lys Asn Asp Asn Lys Pro Met Ser
                85                  90                  95

Gln Asp Thr Trp Asn Ser Leu Lys Gly Leu Val Ala Asp Gln Leu Ser
            100                 105                 110

-continued

```
Gly Lys Arg Leu Phe Val Val Asp Ala Phe Cys Gly Ala Asn Lys Asp
            115                 120                 125
Thr Arg Leu Ala Val Arg Val Thr Glu Val Ala Trp Gln Ala His
        130                 135                 140
Phe Val Thr Asn Met Phe Ile Arg Pro Ser Ala Glu Glu Leu Lys Gly
145                 150                 155                 160
Phe Lys Pro Asp Phe Val Met Asn Gly Ala Lys Cys Thr Asn Pro
                165                 170                 175
Asn Trp Lys Glu Gln Gly Leu Asn Ser Glu Asn Phe Val Ala Phe Asn
                180                 185                 190
Ile Thr Glu Gly Val Gln Leu Ile Gly Gly Thr Trp Tyr Gly Gly Glu
        195                 200                 205
Met Lys Lys Gly Met Phe Ser Met Met Asn Tyr Phe Leu Pro Leu Arg
    210                 215                 220
Gly Ile Ala Ser Met His Cys Ser Ala Asn Val Gly Lys Asp Gly Asp
225                 230                 235                 240
Thr Ala Ile Phe Phe Gly Leu Ser Gly Thr Gly Lys Thr Thr Leu Ser
                245                 250                 255
Thr Asp Pro Lys Arg Gln Leu Ile Gly Asp Asp Glu His Gly Trp Asp
                260                 265                 270
Asp Glu Gly Val Phe Asn Phe Glu Gly Gly Cys Tyr Ala Lys Thr Ile
        275                 280                 285
Asn Leu Ser Ala Glu Asn Glu Pro Asp Ile Tyr Gly Ala Ile Lys Arg
    290                 295                 300
Asp Ala Leu Leu Glu Asn Val Val Val Leu Asp Asn Gly Asp Val Asp
305                 310                 315                 320
Tyr Ala Asp Gly Ser Lys Thr Glu Asn Thr Arg Val Ser Tyr Pro Ile
                325                 330                 335
Tyr His Ile Gln Asn Ile Val Lys Pro Val Ser Lys Ala Gly Pro Ala
        340                 345                 350
Thr Lys Val Ile Phe Leu Ser Ala Asp Ala Phe Gly Val Leu Pro Pro
    355                 360                 365
Val Ser Lys Leu Thr Pro Glu Gln Thr Lys Tyr Tyr Phe Leu Ser Gly
370                 375                 380
Phe Thr Ala Lys Leu Ala Gly Thr Glu Arg Gly Ile Thr Glu Pro Thr
385                 390                 395                 400
Pro Thr Phe Ser Ala Cys Phe Gly Ala Ala Phe Leu Ser Leu His Pro
                405                 410                 415
Thr Gln Tyr Ala Glu Val Leu Val Lys Arg Met Gln Glu Ser Gly Ala
                420                 425                 430
Glu Ala Tyr Leu Val Asn Thr Gly Trp Asn Gly Thr Gly Lys Arg Ile
        435                 440                 445
Ser Ile Lys Asp Thr Arg Gly Ile Ile Asp Ala Ile Leu Asp Gly Ser
    450                 455                 460
Ile Asp Lys Ala Glu Met Gly Ser Leu Pro Ile Phe Asp Phe Ser Ile
465                 470                 475                 480
Pro Lys Ala Leu Pro Gly Val Asn Pro Ala Ile Leu Asp Pro Arg Asp
                485                 490                 495
Thr Tyr Ala Asp Lys Ala Gln Trp Glu Glu Lys Ala Gln Asp Leu Ala
                500                 505                 510
Gly Arg Phe Val Lys Asn Phe Glu Lys Tyr Thr Gly Thr Ala Glu Gly
        515                 520                 525
```

Gln Ala Leu Val Ala Ala Gly Pro Lys Ala
    530             535

<210> SEQ ID NO 18
<211> LENGTH: 1617
<212> TYPE: DNA
<213> ORGANISM: Artificial sequence
<220> FEATURE:
<223> OTHER INFORMATION: PEPcarboxykinase M. succiniciproducens cpo for
      S. cerevisiae

<400> SEQUENCE: 18

| | |
|---|---|
| atgaccgatt tgaaccaatt gactcaagaa ttgggtgctt tgggtattca cgatgtccaa | 60 |
| gaagttgtct acaacccatc ttacgaattg ttgtttgctg aagaaaccaa gccaggtttg | 120 |
| gaaggttacg aaaagggtac tgttaccaac caaggtgctg ttgctgtcaa caccggtatc | 180 |
| ttcaccggtc gttctccaaa ggacaaatac attgtcttgg atgacaagac caaggacact | 240 |
| gtctggtgga cttctgaaaa ggtcaagaac gacaacaaac caatgtccca agacacttgg | 300 |
| aactctttaa agggtttagt cgctgaccaa ttgtctggta gagattatt cgttgtcgat | 360 |
| gctttctgtg gtgccaacaa ggacaccaga ttagctgtca gagttgtcac tgaagttgct | 420 |
| tggcaagctc acttcgttac caacatgttc atcagaccat ctgctgaaga attgaaaggt | 480 |
| ttcaagccag atttcgttgt catgaacggt gccaaatgta ccaacccaaa ctggaaggaa | 540 |
| caaggtttga actctgaaaa ctttgttgct ttcaacatca ctgaaggtgt tcaattgatt | 600 |
| ggtggtacct ggtacggtgg tgaaatgaag aagggtatgt tctccatgat gaactacttc | 660 |
| ttgccattga gaggtattgc ttccatgcac tgttctgcca atgtcggtaa ggacggtgac | 720 |
| actgccatct tcttcggtct atccggtacc ggtaagacca ctttgtccac tgacccaaag | 780 |
| agacaattga ttggtgatga cgaacacggt tgggatgacg aaggtgtttt caactttgaa | 840 |
| ggtggttgtt acgccaagac catcaactta tctgctgaaa atgaaccaga tatctacggt | 900 |
| gccatcaagc gtgacgctct attggaaaac gttgttgttt tggacaatgg tgacgtcgat | 960 |
| tatgctgacg gttccaagac tgaaaacacc agagtttctt acccaatcta ccatattcaa | 1020 |
| aacattgtca gccagttttc caaggctggt ccagctacca agttatctt cttgtctgct | 1080 |
| gatgctttcg gtgttttgcc tcctgtttcc aagttgactc agaacaaac caagtactac | 1140 |
| ttcttgtctg gttcaccgc caagttggct ggtactgaaa aggtatcac tgaaccaact | 1200 |
| ccaactttct ctgcttgttt cggtgctgcc ttttgtctt tgcacccaac tcaatacgct | 1260 |
| gaagttttgg tcaagagaat gcaagaatct ggtgctgaag cttacttggt caacactggt | 1320 |
| tggaacggta ccggtaagag aatctccatc aaagatacca gaggtatcat cgatgccatc | 1380 |
| ttggatggtt ccattgacaa ggctgaaatg ggttctttgc aattttcga tttctccatt | 1440 |
| ccaaaggctt tgccaggtgt caacccagcc atcttagacc aagagacac ctacgctgac | 1500 |
| aaagctcaat gggaagaaaa ggctcaagac ttgctggta gattcgtcaa gaacttcgaa | 1560 |
| aaatacactg gtactgctga aggtcaagct ttggttgctg ctggtccaaa ggcctaa | 1617 |

<210> SEQ ID NO 19
<211> LENGTH: 365
<212> TYPE: PRT
<213> ORGANISM: Artificial sequence
<220> FEATURE:
<223> OTHER INFORMATION: MDH2 S. cerevisiae lacking first 12 a.a.

<400> SEQUENCE: 19

Met Leu Lys Ile Ala Ile Leu Gly Ala Ala Gly Gly Ile Gly Gln Ser

```
          1               5                    10                   15
Leu Ser Leu Leu Leu Lys Ala Gln Leu Gln Tyr Gln Leu Lys Glu Ser
                    20                  25                  30

Asn Arg Ser Val Thr His Ile His Leu Ala Leu Tyr Asp Val Asn Gln
            35                  40                  45

Glu Ala Ile Asn Gly Val Thr Ala Asp Leu Ser His Ile Asp Thr Pro
 50                      55                  60

Ile Ser Val Ser His Ser Pro Ala Gly Gly Ile Glu Asn Cys Leu
 65                  70                  75                  80

His Asn Ala Ser Ile Val Val Ile Pro Ala Gly Val Pro Arg Lys Pro
                    85                  90                  95

Gly Met Thr Arg Asp Asp Leu Phe Asn Val Asn Ala Gly Ile Ile Ser
                100                 105                 110

Gln Leu Gly Asp Ser Ile Ala Glu Cys Cys Asp Leu Ser Lys Val Phe
                115                 120                 125

Val Leu Val Ile Ser Asn Pro Val Asn Ser Leu Val Pro Val Met Val
130                 135                 140

Ser Asn Ile Leu Lys Asn His Pro Gln Ser Arg Asn Ser Gly Ile Glu
145                 150                 155                 160

Arg Arg Ile Met Gly Val Thr Lys Leu Asp Ile Val Arg Ala Ser Thr
                165                 170                 175

Phe Leu Arg Glu Ile Asn Ile Glu Ser Gly Leu Thr Pro Arg Val Asn
                180                 185                 190

Ser Met Pro Asp Val Pro Val Ile Gly Gly His Ser Gly Glu Thr Ile
                195                 200                 205

Ile Pro Leu Phe Ser Gln Ser Asn Phe Leu Ser Arg Leu Asn Glu Asp
210                 215                 220

Gln Leu Lys Tyr Leu Ile His Arg Val Gln Tyr Gly Gly Asp Glu Val
225                 230                 235                 240

Val Lys Ala Lys Asn Gly Lys Gly Ser Ala Thr Leu Ser Met Ala His
                245                 250                 255

Ala Gly Tyr Lys Cys Val Val Gln Phe Val Ser Leu Leu Leu Gly Asn
                260                 265                 270

Ile Glu Gln Ile His Gly Thr Tyr Tyr Val Pro Leu Lys Asp Ala Asn
                275                 280                 285

Asn Phe Pro Ile Ala Pro Gly Ala Asp Gln Leu Leu Pro Leu Val Asp
                290                 295                 300

Gly Ala Asp Tyr Phe Ala Ile Pro Leu Thr Ile Thr Thr Lys Gly Val
305                 310                 315                 320

Ser Tyr Val Asp Tyr Asp Ile Val Asn Arg Met Asn Asp Met Glu Arg
                325                 330                 335

Asn Gln Met Leu Pro Ile Cys Val Ser Gln Leu Lys Lys Asn Ile Asp
                340                 345                 350

Lys Gly Leu Glu Phe Val Ala Ser Arg Ser Ala Ser Ser
                355                 360                 365

<210> SEQ ID NO 20
<211> LENGTH: 1099
<212> TYPE: DNA
<213> ORGANISM: Artificial sequence
<220> FEATURE:
<223> OTHER INFORMATION: cpo MDH2 S. cerevisiae lacking first 12 a.a.

<400> SEQUENCE: 20
atgttgaaga ttgccatctt gggtgctgct ggtggtatcg gtcaatcttt gtctttgttg      60
```

```
ttgaaggctc aattgcaata ccaattgaag gaatccaaca gatctgttac ccacattcat    120
ttggctttgt acgatgtcaa ccaagaagct atcaacggtg tcactgctga cttgtctcac    180
atcgataccc caatctctgt ttcctctcac tctccagctg gtggtattga aaactgtttg    240
cacaacgctt ccattgttgt cattccagcc ggtgttccaa gaaagccagg tatgacccgt    300
gacgatttgt tcaacgtcaa tgccggtatc atctctcaat taggtgattc cattgctgaa    360
tgttgtgact tgtccaaggt tttcgtcttg gttatctcca acccagtcaa ctctttggtt    420
cctgttatgg tttccaacat cttgaagaac cacccacaat ccagaaactc tggtattgaa    480
agaagaatca tgggtgtcac caaattggac attgtcagag cttccacttt cttgagagaa    540
atcaacattg aatctggttt gactccaaga gtcaactcca tgccagatgt tccagttatc    600
ggtggtcact ctggtgaaac tatcatccca ttattctctc aatctaactt cttgtccaga    660
ttgaatgaag atcaattgaa atacttgatt caccgtgtcc aatacggtgg tgacgaagtt    720
gtcaaggcca gaacggtaa gggttctgct actctatcca tggctcatgc cggttacaag    780
tgtgttgtcc aattcgtttc tctattatta ggtaacattg aacaaatcca cggtacctac    840
tacgttccat tgaaagatgc taacaacttc ccaattgctc caggtgctga ccaattattg    900
ccattagtcg acggtgctga ctactttgcc atcccattga ccatcactac caagggtgtt    960
tcttacgttg actacgatat cgtcaacaga atgaacgaca tggaaagaaa ccaaatgttg   1020
cctatctgtg tttctcaatt gaagaagaac attgacaagg gtttggaatt cgttgcttcc   1080
agatctgctt ccagttaag                                                1099
```

<210> SEQ ID NO 21
<211> LENGTH: 340
<212> TYPE: PRT
<213> ORGANISM: Artificial sequence
<220> FEATURE:
<223> OTHER INFORMATION: MDH3 S. cerevisiae lacking C-terminal SKL

<400> SEQUENCE: 21

```
Met Val Lys Val Ala Ile Leu Gly Ala Ser Gly Gly Val Gly Gln Pro
1               5                   10                  15

Leu Ser Leu Leu Leu Lys Leu Ser Pro Tyr Val Ser Glu Leu Ala Leu
            20                  25                  30

Tyr Asp Ile Arg Ala Ala Glu Gly Ile Gly Lys Asp Leu Ser His Ile
        35                  40                  45

Asn Thr Asn Ser Ser Cys Val Gly Tyr Asp Lys Asp Ser Ile Glu Asn
    50                  55                  60

Thr Leu Ser Asn Ala Gln Val Val Leu Ile Pro Ala Gly Val Pro Arg
65                  70                  75                  80

Lys Pro Gly Leu Thr Arg Asp Asp Leu Phe Lys Met Asn Ala Gly Ile
                85                  90                  95

Val Lys Ser Leu Val Thr Ala Val Gly Lys Phe Ala Pro Asn Ala Arg
            100                 105                 110

Ile Leu Val Ile Ser Asn Pro Val Asn Ser Leu Val Pro Ile Ala Val
        115                 120                 125

Glu Thr Leu Lys Lys Met Gly Lys Phe Lys Pro Gly Asn Val Met Gly
    130                 135                 140

Val Thr Asn Leu Asp Leu Val Arg Ala Glu Thr Phe Leu Val Asp Tyr
145                 150                 155                 160

Leu Met Leu Lys Asn Pro Lys Ile Gly Gln Glu Gln Asp Lys Thr Thr
                165                 170                 175
```

```
Met His Arg Lys Val Thr Val Ile Gly Gly His Ser Gly Glu Thr Ile
            180                 185                 190

Ile Pro Ile Ile Thr Asp Lys Ser Leu Val Phe Gln Leu Asp Lys Gln
        195                 200                 205

Tyr Glu His Phe Ile His Arg Val Gln Phe Gly Gly Asp Glu Ile Val
    210                 215                 220

Lys Ala Lys Gln Gly Ala Gly Ser Ala Thr Leu Ser Met Ala Phe Ala
225                 230                 235                 240

Gly Ala Lys Phe Ala Glu Val Leu Arg Ser Phe His Asn Glu Lys
                245                 250                 255

Pro Glu Thr Glu Ser Leu Ser Ala Phe Val Tyr Leu Pro Gly Leu Lys
            260                 265                 270

Asn Gly Lys Lys Ala Gln Gln Leu Val Gly Asp Asn Ser Ile Glu Tyr
        275                 280                 285

Phe Ser Leu Pro Ile Val Leu Arg Asn Gly Ser Val Val Ser Ile Asp
    290                 295                 300

Thr Ser Val Leu Glu Lys Leu Ser Pro Arg Glu Glu Gln Leu Val Asn
305                 310                 315                 320

Thr Ala Val Lys Glu Leu Arg Lys Asn Ile Glu Lys Gly Lys Ser Phe
                325                 330                 335

Ile Leu Asp Ser
            340

<210> SEQ ID NO 22
<211> LENGTH: 1024
<212> TYPE: DNA
<213> ORGANISM: Artificial sequence
<220> FEATURE:
<223> OTHER INFORMATION: MDH3 S. cerevisiae lacking SKL encoding nt, cpo

<400> SEQUENCE: 22
atggttaagg ttgccatctt aggtgcttct ggtggtgtcg gtcaaccatt atctctatta      60
ttgaaattgt ctccatacgt ttctgaattg ctttgtacg atatcagagc tgctgaaggt     120
attggtaagg atttgtccca catcaacacc aactcctctt gtgttggtta cgacaaggat     180
tccatcgaaa acactttgtc caatgctcaa gttgtcttga ttccagctgg tgttccaaga     240
aagccaggtt tgaccagaga tgatttgttc aagatgaacg ctggtatcgt taagtctttg     300
gttactgctg tcggtaaatt tgccccaaac gctcgtatct tagtcatctc caaccctgtt     360
aactctttgg ttccaattgc cgttgaaact ttgaagaaga tgggtaagtt caagccaggt     420
aacgttatgg gtgtcaccaa cttggatttg gtcagagctg aaactttctt ggttgactac     480
ttgatgttga gaacccccaaa gatcggtcaa gaacaagaca agaccaccat gcacagaaag     540
gtcaccgtca tcggtggtca ctctggtgaa accatcattc aatcatcac tgacaaatcc     600
ttggttttcc aattggacaa gcaatacgaa catttcatcc acagagtcca attcggtggt     660
gacgaaattg tcaaggccaa gcaaggtgcc ggttctgcta ccttgtccat ggctttcgct     720
ggtgccaaat ttgctgaaga agtcttacgt tctttccaca acgaaaagcc agaaactgaa     780
tctttgtctg ctttcgtcta cttgccaggt ttgaagaacg gtaagaaggc tcaacaatta     840
gtcggtgaca actccattga atacttctct tgccaattg ttttgagaaa cggttccgtt     900
gtttccattg acacttctgt tttggaaaaa ttgtctccaa gagaagaaca attggtcaac     960
actgctgtca aggaattgag aaagaacatt gaaaagggta gtctttcat cttggacagt    1020
taag                                                                 1024
```

<210> SEQ ID NO 23
<211> LENGTH: 472
<212> TYPE: PRT
<213> ORGANISM: Artificial sequence
<220> FEATURE:
<223> OTHER INFORMATION: Fumarase R. oryzae lacking first 23 aa+ new M

<400> SEQUENCE: 23

```
Met Ser Ser Ala Ser Ala Ala Leu Gln Lys Phe Arg Ala Glu Arg Asp
1               5                   10                  15

Thr Phe Gly Asp Leu Gln Val Pro Ala Asp Arg Tyr Trp Gly Ala Gln
            20                  25                  30

Thr Gln Arg Ser Leu Gln Asn Phe Asp Ile Gly Gly Pro Thr Glu Arg
        35                  40                  45

Met Pro Glu Pro Leu Ile Arg Ala Phe Gly Val Leu Lys Lys Ala Ala
    50                  55                  60

Ala Thr Val Asn Met Thr Tyr Gly Leu Asp Pro Lys Val Gly Glu Ala
65                  70                  75                  80

Ile Gln Lys Ala Ala Asp Glu Val Ile Asp Gly Ser Leu Ile Asp His
                85                  90                  95

Phe Pro Leu Val Val Trp Gln Thr Gly Ser Gly Thr Gln Thr Lys Met
            100                 105                 110

Asn Val Asn Glu Val Ile Ser Asn Arg Ala Ile Glu Leu Leu Gly Gly
        115                 120                 125

Glu Leu Gly Ser Lys Ala Pro Val His Pro Asn Asp His Val Asn Met
    130                 135                 140

Ser Gln Ser Ser Asn Asp Thr Phe Pro Thr Ala Met His Val Ala Ala
145                 150                 155                 160

Val Val Glu Ile His Gly Arg Leu Ile Pro Ala Leu Thr Thr Leu Arg
                165                 170                 175

Asp Ala Leu Gln Ala Lys Ser Ala Glu Phe Glu His Ile Ile Lys Ile
            180                 185                 190

Gly Arg Thr His Leu Gln Asp Ala Thr Pro Leu Thr Leu Gly Gln Glu
        195                 200                 205

Phe Ser Gly Tyr Thr Gln Gln Leu Thr Tyr Gly Ile Ala Arg Val Gln
    210                 215                 220

Gly Thr Leu Glu Arg Leu Tyr Asn Leu Ala Gln Gly Gly Thr Ala Val
225                 230                 235                 240

Gly Thr Gly Leu Asn Thr Arg Lys Gly Phe Asp Ala Lys Val Ala Glu
                245                 250                 255

Ala Ile Ala Ser Ile Thr Gly Leu Pro Phe Lys Thr Ala Pro Asn Lys
            260                 265                 270

Phe Glu Ala Leu Ala Ala His Asp Ala Leu Val Glu His Gly Ala
        275                 280                 285

Leu Asn Thr Val Ala Cys Ser Leu Met Lys Ile Ala Asn Asp Ile Arg
    290                 295                 300

Tyr Leu Gly Ser Gly Pro Arg Cys Gly Leu Gly Glu Leu Ser Leu Pro
305                 310                 315                 320

Glu Asn Glu Pro Gly Ser Ser Ile Met Pro Gly Lys Val Asn Pro Thr
                325                 330                 335

Gln Cys Glu Ala Met Thr Met Val Cys Ala Gln Val Met Gly Asn Asn
            340                 345                 350

Thr Ala Ile Ser Val Ala Gly Ser Asn Gly Gln Phe Glu Leu Asn Val
        355                 360                 365
```

```
Phe Lys Pro Val Met Ile Lys Asn Leu Ile Gln Ser Ile Arg Leu Ile
    370                 375                 380

Ser Asp Ala Ser Ile Ser Phe Thr Lys Asn Cys Val Val Gly Ile Glu
385                 390                 395                 400

Ala Asn Glu Lys Lys Ile Ser Ser Ile Met Asn Glu Ser Leu Met Leu
                405                 410                 415

Val Thr Ala Leu Asn Pro His Ile Gly Tyr Asp Lys Ala Ala Lys Cys
            420                 425                 430

Ala Lys Lys Ala His Lys Glu Gly Thr Thr Leu Lys Glu Ala Ala Leu
        435                 440                 445

Ser Leu Gly Tyr Leu Thr Ser Glu Glu Phe Asp Gln Trp Val Arg Pro
    450                 455                 460

Glu Asp Met Ile Ser Ala Lys Asp
465                 470
```

<210> SEQ ID NO 24
<211> LENGTH: 1419
<212> TYPE: DNA
<213> ORGANISM: Artificial sequence
<220> FEATURE:
<223> OTHER INFORMATION: Fumarase R. oryzae lacking nt encoding first
      aa + M

<400> SEQUENCE: 24

```
atgtcctctg cttctgctgc tttgcaaaaa ttcagagctg aaagagatac cttcggtgac     60
ttgcaagttc cagctgaccg ttactggggt gctcaaactc aaagatcttt gcaaaacttt    120
gacattggtg gtccaactga agaatgcca gaaccattaa tcagagcttt cggtgttttg    180
aagaaggctg ctgccaccgt caacatgacc tacggtttgg acccaaaggt tggtgaagcc    240
atccaaaagg ctgctgacga agttatcgat ggttctttga ttgaccattt cccattggtt    300
gtctggcaaa ccggttctgg tactcaaacc aagatgaacg tcaatgaagt catctccaac    360
agagccattg aattgttggg tggtgaatta ggttccaagg ctccagtcca cccaaacgat    420
catgtcaaca tgtctcaatc ttccaacgac actttcccaa ctgccatgca cgttgctgcc    480
gttgttgaaa ttcacggtag attgattcca gctttgacca ctttgagaga tgctttgcaa    540
gccaaatctg ctgaattcga acacatcatc aagattggta aacccacttg caagatgct     600 accccattga ctttaggtca agaattctcc ggttacactc aacaattgac ctacggtatt    660
gctcgtgttc aaggtacttt ggaaagatta taacttgg ctcaaggtgg tactgctgtc     720
ggtactggtt tgaacaccag aaagggtttc gatgccaagg ttgctgaagc cattgcttcc    780
atcactggtt taccattcaa gaccgctcca aacaaattcg aagctttggc tgctcacgac    840
gctttggttg aagctcacgg tgctttgaac accgttgctt gttcttttgat gaagattgcc    900 aacgatatcc gttacttggg ttctggtcca agatgtggtt taggtgaatt gtctctacca    960
gaaaacgaac aggttcttc catcatgcca ggtaaggtca acccaactca atgtgaagct    1020
atgaccatgg tttgtgctca agtcatgggt aacaacactg ccatctctgt tgctggttcc    1080
aacggtcaat tcgaattgaa tgtctttaaa ccagtcatga tcaagaactt gatccaatcc    1140
atcagattaa tctctgacgc ttccatctct ttcaccaaga actgtgttgt cggtattgaa    1200
gctaacgaaa agaagatctc ctccatcatg aacgaatctt tgatgttggt cactgctttg    1260
aaccctcaca ttggttacga caaggctgcc aagtgtgcca agaaggctca caaggaaggt    1320
accactttga agaagctgc tctatctttg ggttacttga cctctgaaga attcgaccaa    1380
```
tgggttagac ctgaggacat gatttctgcc aaggattaa            1419

<210> SEQ ID NO 25
<211> LENGTH: 1000
<212> TYPE: DNA
<213> ORGANISM: Artificial sequence
<220> FEATURE:
<223> OTHER INFORMATION: TDH1 promotor

<400> SEQUENCE: 25

```
cttccctttt acagtgcttc ggaaaagcac agcgttgtcc aagggaacaa ttttcttca     60
agttaatgca taagaaatat cttttttat gtttagctaa gtaaaagcag cttggagtaa   120
aaaaaaaat gagtaaattt ctcgatggat tagtttctca caggtaacat aacaaaaacc   180
aagaaaagcc cgcttctgaa aactacagtt gacttgtatg ctaaagggcc agactaatgg   240
gaggagaaaa agaaacgaat gtatatgctc atttacactc tatatcacca tatggaggat   300
aagttgggct gagcttctga tccaatttat tctatccatt agttgctgat atgtcccacc   360
agccaacact tgatagtatc tactcgccat tcacttccag cagcgccagt agggttgttg   420
agcttagtaa aaatgtgcgc accacaagcc tacatgactc cacgtcacat gaaaccacac   480
cgtgggcct tgttgcgcta ggaataggat atgcgacgaa gacgcttctg cttagtaacc   540
acaccacatt ttcaggggt cgatctgctt gcttccttta ctgtcacgag cggcccataa   600
tcgcgctttt tttttaaaag gcgcgagaca gcaaacagga agctcgggtt tcaaccttcg   660
gagtggtcgc agatctggag actggatctt tacaatacag taaggcaagc caccatctgc   720
ttcttaggtg catgcgacgg tatccacgtg cagaacaaca tagtctgaag aagggggga   780
ggagcatgtt cattctctgt agcagtaaga gcttggtgat aatgaccaaa actggagtct   840
cgaaatcata taaatagaca atatattttc acacaatgag atttgtagta cagttctatt   900
ctctctcttg cataaataag aaattcatca agaacttggt ttgatatttc accaacacac   960
acaaaaaaca gtacttcact aaatttacac acaaaacaaa                       1000
```

<210> SEQ ID NO 26
<211> LENGTH: 500
<212> TYPE: DNA
<213> ORGANISM: Artificial sequence
<220> FEATURE:
<223> OTHER INFORMATION: TDH1 terminator

<400> SEQUENCE: 26

```
ataaagcaat cttgatgagg ataatgattt ttttttgaat atacataaat actaccgttt     60
ttctgctaga ttttgtgaag acgtaaataa gtacatatta cttttaagc caagacaaga   120
ttaagcatta actttaccct tttctcttct aagtttcaat actagttatc actgtttaaa   180
agttatggcg agaacgtcgg cggttaaaat atattaccct gaacgtggtg aattgaagtt   240
ctaggatggt ttaaagattt tcccttttg ggaaataagt aaacaatata ttgctgcctt   300
tgcaaaacgc acataccac aatatgtgac tattggcaaa gaacgcatta tccttttgaag   360
aggtggatac tgatactaag agagtctcta ttccggctcc actttagtc cagagattac   420
ttgtcttctt acgtatcaga acaagaaagc atttccaaag taattgcatt tgcccttgag   480
cagtatatat atactaagaa                                              500
```

<210> SEQ ID NO 27
<211> LENGTH: 600
<212> TYPE: DNA
<213> ORGANISM: Artificial sequence
<220> FEATURE:
<223> OTHER INFORMATION: second TDH3 promotor

<400> SEQUENCE: 27

| ttagtcaaaa aattagcctt ttaattctgc tgtaacccgt acatgcccaa aataggggc | 60 |
| gggttacaca gaatatataa catcgtaggt gtctgggtga acagtttatt cctggcatcc | 120 |
| actaaatata atggagcccg cttttaagc tggcatccag aaaaaaaag aatcccagca | 180 |
| ccaaaatatt gttttcttca ccaaccatca gttcataggt ccattctctt agcgcaacta | 240 |
| cagagaacag gggcacaaac aggcaaaaaa cgggcacaac ctcaatggag tgatgcaacc | 300 |
| tgcctggagt aaatgatgac acaaggcaat tgacccacgc atgtatctat ctcattttct | 360 |
| tacaccttct attaccttct gctctctctg atttggaaaa agctgaaaaa aaaggttgaa | 420 |
| accagttccc tgaaattatt cccctacttg actaataagt atataaagac ggtaggtatt | 480 |
| gattgtaatt ctgtaaatct atttcttaaa cttcttaaat tctactttta tagttagtct | 540 |
| tttttttagt tttaaaacac caagaactta gtttcgaata acacacata aacaaacaaa | 600 |

<210> SEQ ID NO 28
<211> LENGTH: 300
<212> TYPE: DNA
<213> ORGANISM: Artificial sequence
<220> FEATURE:
<223> OTHER INFORMATION: second TDH3 terminator

<400> SEQUENCE: 28

| gtgaatttac tttaaatctt gcatttaaat aaattttctt tttatagctt tatgacttag | 60 |
| tttcaattta tatactattt taatgacatt ttcgattcat tgattgaaag ctttgtgttt | 120 |
| tttcttgatg cgctattgca ttgttcttgt ctttttcgcc acatgtaata tctgtagtag | 180 |
| atacctgata cattgtggat gctgagtgaa attttagtta ataatggagg cgctcttaat | 240 |
| aattttgggg atattggctt ttttttttaa agtttacaaa tgaattttt ccgccaggat | 300 |

<210> SEQ ID NO 29
<211> LENGTH: 3148
<212> TYPE: DNA
<213> ORGANISM: Artificial sequence
<220> FEATURE:
<223> OTHER INFORMATION: TDH1p-PCKm-TDH1t synthetic construct

<400> SEQUENCE: 29

| ggatcccttc cctttacag tgcttcggaa aagcacagcg ttgtccaagg gaacaatttt | 60 |
| tcttcaagtt aatgcataag aaatatcttt tttatgttt agctaagtaa agcagcttg | 120 |
| gagtaaaaaa aaaaatgagt aaatttctcg atggattagt ttctcacagg taacataaca | 180 |
| aaaccaaga aaagcccgct tctgaaaact acagttgact tgtatgctaa agggccagac | 240 |
| taatgggagg agaaaagaa acgaatgtat atgctcattt acactctata tcaccatatg | 300 |
| gaggataagt tgggctgagc ttctgatcca atttattcta tccattagtt gctgatatgt | 360 |
| cccaccagcc aacacttgat agtatctact cgccattcac ttccagcagc gccagtaggg | 420 |
| ttgttgagct tagtaaaaat gtgcgcacca caagcctaca tgactccacg tcacatgaaa | 480 |
| ccacaccgtg gggccttgtt gcgctaggaa taggatatgc gacgaagacg cttctgctta | 540 |
| gtaaccacac cacattttca gggggtcgat ctgcttgctt cctttactgt cacgagcggc | 600 |
| ccataatcgc gctttttttt taaaggcgc gagacagcaa acaggaagct cgggtttcaa | 660 |
| ccttcggagt ggtcgcagat ctggagactg gatctttaca atacagtaag gcaagccacc | 720 |

```
atctgcttct taggtgcatg cgacggtatc cacgtgcaga caacatagt ctgaagaagg      780
gggggaggag catgttcatt ctctgtagca gtaagagctt ggtgataatg accaaaactg      840
gagtctcgaa atcatataaa tagacaatat attttcacac aatgagattt gtagtacagt      900
tctattctct ctcttgcata aataagaaat tcatcaagaa cttggtttga tatttcacca      960
acacacacaa aaacagtac ttcactaaat ttacacacaa aacaaaatga ctgatttgaa     1020
caaattggtc aaggaattga atgatttggg tttgactgac gtcaaggaaa ttgtctacaa     1080
cccatcttac gaacaattat tcgaagaaga aaccaagcca ggtttggaag gtttcgacaa     1140
gggtactttg accactttag gtgctgttgc tgttgacacc ggtattttca ccggtcgttc     1200
tccaaaggac aaatacattg tttgtgatga accaccaag gacaccgtct ggtggaactc     1260
tgaagctgcc aagaacgata caagccaat gactcaagaa acctggaaat ctttgagaga     1320
attggttgcc aagcaattgt ctggtaagag attattcgtt gttgacgctt tctgtggtgc     1380
ttctgaaaag cacagaattg gtgtcagaat ggtcactgaa gttgcttggc aagctcattt     1440
cgtcaagaac atgttcatca gaccaactga cgaagaattg aagaacttca aggctgactt     1500
caccgttttg aatggtgcca agtgtaccaa cccaaactgg aaggaacaag gtttgaactc     1560
tgaaaacttt gttgctttca acatcactga aggtatccaa ttgattggtg gtacctggta     1620
cggtggtgaa atgaagaagg gtatgttctc catgatgaac tatttcttgc cattgaaagg     1680
tgttgcttcc atgcactgtt ctgccaatgt cggtaaggat ggtgacgttg ccatcttctt     1740
cggtctatcc ggtactggta agaccactct atccactgac ccaagagac aattgattgg     1800
tgatgacgaa cacggttggg acgaatctgg tgtctttaac tttgaaggtg gttgttacgc     1860
caagaccatc aacttatctc aagaaaacga accagatatc tacggtgcca tccgtcgtga     1920
tgctttgttg gaaaacgttg ttgtcagagc tgacggttct gttgacttcg acgacggttc     1980
caagactgaa aacaccagag tttcttaccc aatctaccac attgacaaca ttgtcagacc     2040
tgtttccaag gctggtcacg ctaccaaggt tatcttcttg actgctgatg ctttcggtgt     2100
cttgccacct gtttccaaat tgactccaga acaaaccgaa tactacttct gtccggtttt     2160
cactgccaaa ttggctggta ctgaaagagg tgtcactgaa ccaactccaa ctttctctgc     2220
ttgtttcggt gctgctttct tatctttgca cccaatccaa tacgctgatg tcttggttga     2280
aagaatgaag gcttctggtg ctgaagctta cttggtcaac accggttgga acggtaccgg     2340
taagagaatc tccatcaagg ataccagagg tatcattgat gctatcttgg acggttccat     2400
tgaaaaggct gaaatgggtg aattgccaat cttcaacttg gccattccaa aggctttgcc     2460
aggtgttgac ccagccatct tagatccaag agacacctac gctgacaagg ctcaatggca     2520
agtcaaggct gaagatttgg ctaacagatt cgtcaagaac tttgtcaaat acactgctaa     2580
cccagaagct gccaaattgg ttggtgctgg tccaaaggct taaggcccgg gcataaagca     2640
atcttgatga ggataatgat ttttttttga atatacataa atactaccgt ttttctgcta     2700
gattttgtga agacgtaaat aagtacatat tacttttttaa gccaagacaa gattaagcat     2760
taactttacc cttttctctt ctaagtttca atactagtta tcactgttta aaagttatgg     2820
cgagaacgtc ggcggttaaa atatattacc ctgaacgtgg tgaattgaag ttctaggatg     2880
gtttaaagat ttttcctttt tgggaaataa gtaaacaata tattgctgcc tttgcaaaac     2940
gcacataccc acaatatgtg actattggca aagaacgcat tatcctttga gaggtggat     3000
actgatacta agagagtctc tattccggct ccacttttag tccagagatt acttgtcttc     3060
ttacgtatca gaacaagaaa gcatttccaa agtaattgca tttgcccttg agcagtatat     3120
```
atatactaag aaggcgcgcc gcggccgc        3148

<210> SEQ ID NO 30
<211> LENGTH: 3148
<212> TYPE: DNA
<213> ORGANISM: Artificial sequence
<220> FEATURE:
<223> OTHER INFORMATION: TDH1p-PCK1-TDH1t synthetic construct

<400> SEQUENCE: 30

```
ggatccctte cctttacag tgcttcggaa agcacagcg ttgtccaagg gaacaatttt    60
tcttcaagtt aatgcataag aaatatcttt ttttatgttt agctaagtaa aagcagcttg   120
gagtaaaaaa aaaatgagt aaatttctcg atggattagt ttctcacagg taacataaca   180
aaaaccaaga aagcccgct tctgaaaact acagttgact tgtatgctaa agggccagac   240
taatgggagg agaaaaagaa acgaatgtat atgctcattt acactctata tcaccatatg   300
gaggataagt tgggctgagc ttctgatcca atttattcta tccattagtt gctgatatgt   360
cccaccagcc aacacttgat agtatctact cgccattcac ttccagcagc gccagtaggg   420
ttgttgagct tagtaaaaat gtgcgcacca caagcctaca tgactccacg tcacatgaaa   480
ccacaccgtg gggccttgtt gcgctaggaa taggatatgc gacgaagacg cttctgctta   540
gtaaccacac acattttca gggggtcgat ctgcttgctt cctttactgt cacgagcggc   600
ccataatcgc gcttttttt taaaaggcgc gagacagcaa acaggaagct cgggtttcaa   660
ccttcggagt ggtcgcagat ctggagactg gatctttaca atacagtaag gcaagccacc   720
atctgcttct taggtgcatg cgacggtatc cacgtgcaga caacatagt ctgaagaagg    780
ggggaggag catgttcatt ctctgtagca gtaagagctt ggtgataatg accaaaactg   840
gagtctcgaa atcatataaa tagacaatat attttcacac aatgagattt gtagtacagt   900
tctattctct ctcttgcata aataagaaat tcatcaagaa cttggtttga tatttcacca   960
acacacacaa aaacagtac ttcactaaat ttacacacaa acaaaatga ccgatttgaa    1020
ccaattgact caagaattgg gtgctttggg tattccgat gtccaagaag ttgtctacaa   1080
cccatcttac gaattgttgt ttgctgaaga accaagcca ggtttggaag ttacgaaaa    1140
gggtactgtt accaaccaag gtgctgttgc tgtcaacacc ggtatcttca ccggtcgttc   1200
tccaaaggac aaatacattg tcttggatga caagaccaag gacactgtct ggtggacttc   1260
tgaaaaggtc aagaacgaca acaaaccaat gtcccaagac acttggaact ctttaaaggg   1320
tttagtcgct gaccaattgt ctggtaagag attattcgtt gtcgatgctt ctgtggtgc    1380
caacaaggac accagattag ctgtcagagt tgtcactgaa gttgcttggc aagctcactt   1440
cgttaccaac atgttcatca gaccatctgc tgaagaattg aaaggtttca gccagatttt   1500
cgttgtcatg aacggtgcca atgtaccaa cccaaactgg aaggaacaag gtttgaactc   1560
tgaaactttt gttgctttca acatcactga aggtgttcaa ttgattggtg tacctggta   1620
cggtggtgaa atgaagaagg gtatgttctc catgatgaac tacttcttgc cattgagagg   1680
tattgcttcc atgcactgtt ctgccaatgt cggtaaggac ggtgacactg ccatcttctt   1740
cggtctatcc ggtaccggta agaccacttt gtccactgac ccaaagagac aattgattgg   1800
tgatgacgaa cacggttggg atgacgaagg tgttttcaac tttgaaggtg gttgttacgc   1860
caagaccatc aacttatctg ctgaaaatga accagatatc tacggtgcca tcaagcgtga   1920
cgctctattg gaaaacgttg ttgttttgga caatggtgac gtcgattatg ctgacggttc   1980
```

```
caagactgaa acaccagag tttcttaccc aatctaccat attcaaaaca ttgtcaagcc    2040
agtttccaag gctggtccag ctaccaaagt tatcttcttg tctgctgatg ctttcggtgt    2100
tttgcctcct gtttccaagt tgactccaga acaaaccaag tactacttct tgtctggttt    2160
caccgccaag ttggctggta ctgaaagagg tatcactgaa ccaactccaa ctttctctgc    2220
ttgtttcggt gctgcctttt tgtctttgca cccaactcaa tacgctgaag ttttggtcaa    2280
gagaatgcaa gaatctggtg ctgaagctta cttggtcaac actggttgga acggtaccgg    2340
taagagaatc tccatcaaag ataccagagg tatcatcgat gccatcttgg atggttccat    2400
tgacaaggct gaaatgggtt ctttgccaat tttcgatttc tccattccaa aggctttgcc    2460
aggtgtcaac ccagccatct tagacccaag agacacctac gctgacaaag ctcaatggga    2520
agaaaaggct caagacttgg ctggtagatt cgtcaagaac ttcgaaaaat acactggtac    2580
tgctgaaggt caagctttgg ttgctgctgg tccaaaggcc taaggcccgg gcataaagca    2640
atcttgatga ggataatgat ttttttttga atatacataa atactaccgt ttttctgcta    2700
gattttgtga agacgtaaat aagtacatat tactttttaa gccaagacaa gattaagcat    2760
taactttacc cttttctctt ctaagtttca atactagtta tcactgttta aaagttatgg    2820
cgagaacgtc ggcggttaaa atatattacc ctgaacgtgg tgaattgaag ttctaggatg    2880
gtttaaagat ttttccttt tgggaaataa gtaaacaata tattgctgcc tttgcaaaac    2940
gcacataccc acaatatgtg actattggca agaacgcat tatcctttga agaggtggat    3000
actgatacta agagagtctc tattccggct ccacttttag tccagagatt acttgtcttc    3060
ttacgtatca gaacaagaaa gcatttccaa agtaattgca tttgcccttg agcagtatat    3120
atatactaag aaggcgcgcc gcggccgc                                      3148
```

<210> SEQ ID NO 31
<211> LENGTH: 2637
<212> TYPE: DNA
<213> ORGANISM: Artificial sequence
<220> FEATURE:
<223> OTHER INFORMATION: TDH3p-delta 12N MDH2-TDH3t synthetic construct

<400> SEQUENCE: 31

```
ggatccggcg cgccctattt tcgaggacct tgtcaccttg agcccaagag agccaagatt     60
taaattttcc tatgacttga tgcaaattcc caaagctaat aacatgcaag acacgtacgg    120
tcaagaagac atatttgacc tcttaacagg ttcagacgcg actgcctcat cagtaagacc    180
cgttgaaaag aacttacctg aaaaaaacga atatatacta gcgttgaatg ttagcgtcaa    240
caacaagaag tttaatgacg cggaggccaa ggcaaaaaga ttccttgatt acgtaaggga    300
gttagaatca ttttgaataa aaaacacgct ttttcagttc gagtttatca ttatcaatac    360
tgccatttca agaatacgt aaataattaa tagtagtgat tttcctaact ttatttagtc    420
aaaaaattag cctttttaatt ctgctgtaac ccgtacatgc ccaaaatagg gggcgggtta    480
cacagaatat ataacatcgt aggtgtctgg gtgaacagtt tattcctggc atccactaaa    540
tataatggag cccgcttttt aagctggcat ccagaaaaaa aagaatccc agcaccaaaa    600
tattgttttc ttcaccaacc atcagttcat aggtccattc tcttagcgca actacagaga    660
acagggcac aaacaggcaa aaacgggca aacctcaat ggagtgatgc aacctgcctg    720
gagtaaatga tgcacaagg caattgaccc acgcatgtat ctatctcatt ttcttacacc    780
ttctattacc ttctgctctc tctgatttgg aaaagctgaa aaaaaaggt tgaaccagt    840
tccctgaaat tattccccta cttgactaat aagtatataa agacggtagg tattgattgt    900
```

```
aattctgtaa atctatttct taaacttctt aaattctact tttatagtta gtctttttt    960 tagttttaaa acaccaagaa cttagtttcg aataaacaca cataaacaaa caaaatgttg   1020
aagattgcca tcttgggtgc tgctggtggt atcggtcaat ctttgtcttt gttgttgaag   1080
gctcaattgc aataccaatt gaaggaatcc aacagatctg ttacccacat tcatttggct   1140
ttgtacgatg tcaaccaaga agctatcaac ggtgtcactg ctgacttgtc tcacatcgat   1200
accccaatct ctgtttcctc tcactctcca gctggtggta ttgaaaactg tttgcacaac   1260
gcttccattg ttgtcattcc agccggtgtt ccaagaaagc caggtatgac ccgtgacgat   1320
ttgttcaacg tcaatgccgg tatcatctct caattaggtg attccattgc tgaatgttgt   1380
gacttgtcca aggttttcgt cttggttatc tccaacccag tcaactcttt ggttcctgtt   1440
atggtttcca acatcttgaa gaaccaccca caatccagaa actctggtat tgaaagaaga   1500
atcatgggtg tcaccaaatt ggacattgtc agagcttcca ctttcttgag agaaatcaac   1560
attgaatctg gtttgactcc aagagtcaac tccatgccag atgttccagt tatcggtggt   1620
cactctggtg aaactatcat cccattattc tctcaatcta acttcttgtc cagattgaat   1680
gaagatcaat tgaaatactt gattcaccgt gtccaatacg tggtgacga agttgtcaag    1740 gccaagaacg gtaagggttc tgctactcta tccatggctc atgccggtta caagtgtgtt   1800
gtccaattcg tttctctatt attaggtaac attgaacaaa tccacggtac ctactacgtt   1860
ccattgaaag atgctaacaa cttcccaatt gctccaggtg ctgaccaatt attgccatta   1920
gtcgacggtg ctgactactt tgccatccca ttgaccatca ctaccaaggg tgtttcttac   1980
gttgactacg atatcgtcaa cagaatgaac gacatggaaa gaaaccaaat gttgcctatc   2040
tgtgtttctc aattgaagaa gaacattgac aagggtttgg aattcgttgc ttccagatct   2100
gcttccagtt aaggcccggg cgtgaattta ctttaaatct tgcatttaaa taaattttct   2160
ttttatagct ttatgactta gtttcaattt atatactatt ttaatgacat tttcgattca   2220
ttgattgaaa gctttgtgtt ttttcttgat gcgctattgc attgttcttg tcttttcgc   2280 cacatgtaat atctgtagta gatacctgat acattgtgga tgctgagtga aatttttagt   2340
aataatggag gcgctcttaa taattttggg gatattggct ttttttttta aagtttacaa   2400
atgaattttt tccgccagga taacgattct gaagttactc ttagcgttcc tatcggtaca   2460
gccatcaaat catgcctata aatcatgcct atatttgcgt gcagtcagta tcatctacat   2520
gaaaaaaact cccgcaattt cttatagaat acgttgaaaa ttaaatgtac gcgccaagat   2580
aagataacat atatctagat gcagtaatat acacagattc cggccggccg cggccgc     2637
```

<210> SEQ ID NO 32
<211> LENGTH: 1966
<212> TYPE: DNA
<213> ORGANISM: Artificial sequence
<220> FEATURE:
<223> OTHER INFORMATION: TDH3p-MDH3-TDH3t synthetic construct

<400> SEQUENCE: 32

```
ggatccggcg cgccacgcgt ggccggcctt agtcaaaaaa ttagccttt aattctgctg     60 taacccgtac atgcccaaaa tagggggcgg gttacacaga atatataaca tcgtaggtgt    120
ctgggtgaac agtttattcc tggcatccac taaatataat ggagcccgct ttttaagctg    180
gcatccagaa aaaaaagaa tcccagcacc aaaatattgt tttcttcacc aaccatcagt    240
tcataggtcc attctcttag cgcaactaca gagaacaggg gcacaaacag gcaaaaaacg    300
```

```
ggcacaacct caatggagtg atgcaacctg cctggagtaa atgatgacac aaggcaattg    360
acccacgcat gtatctatct cattttctta caccttctat taccttctgc tctctctgat    420
ttggaaaaag ctgaaaaaaa aggttgaaac cagttccctg aaattattcc cctacttgac    480
taataagtat ataaagacgg taggtattga ttgtaattct gtaaatctat ttcttaaact    540
tcttaaattc tactttttata gttagtcttt ttttttagttt taaaacacca agaacttagt    600
ttcgaataaa cacacataaa caaacaaaat ggttaaggtt gccatcttag gtgcttctgg    660
tggtgtcggt caaccattat ctctattatt gaaattgtct ccatacgttt ctgaattggc    720
tttgtacgat atcagagctg ctgaaggtat tggtaaggat ttgtcccaca tcaacaccaa    780
ctcctcttgt gttggttacg acaaggattc catcgaaaac actttgtcca atgctcaagt    840
tgtcttgatt ccagctggtg ttccaagaaa gccaggtttg accagagatg atttgttcaa    900
gatgaacgct ggtatcgtta agtctttggt tactgctgtc ggtaaatttg ccccaaacgc    960
tcgtatctta gtcatctcca accctgttaa ctctttggtt ccaattgccg ttgaaacttt    1020
gaagaagatg ggtaagttca agccaggtaa cgttatgggt gtcaccaact tggatttggt    1080
cagagctgaa actttcttgg ttgactactt gatgttgaag aacccaaaga tcggtcaaga    1140
acaagacaag accaccatgc acagaaaggt caccgtcatc ggtggtcact ctggtgaaac    1200
catcattcca atcatcactg acaaatcctt ggttttccaa ttggacaagc aatacgaaca    1260
tttcatccac agagtccaat tcggtggtga cgaaattgtc aaggccaagc aaggtgccgg    1320
ttctgctacc ttgtccatgg ctttcgctgg tgccaaattt gctgaagaag tcttacgttc    1380
tttccacaac gaaaagccag aaactgaatc tttgtctgct ttcgtctact gccaggttt    1440 gaagaacggt aagaaggctc aacaattagt cggtgacaac tccattgaat acttctcttt    1500
gccaattgtt ttgagaaacg gttccgttgt ttccattgac acttctgttt tggaaaaatt    1560
gtctccaaga gaagaacaat tggtcaacac tgctgtcaag gaattgagaa agaacattga    1620
aaagggtaag tctttcatct tggacagtta aggtgaattt actttaaatc ttgcatttaa    1680
ataaattttc tttttatagc tttatgactt agtttcaatt tatatactat tttaatgaca    1740
ttttcgattc attgattgaa agctttgtgt tttttcttga tgcgctattg cattgttctt    1800 gtcttttttcg ccacatgtaa tatctgtagt agataccotga tacattgtgg atgctgagtg    1860 aaatttttagt taataatgga ggcgctctta ataattttgg ggatattggc tttttttttt    1920
aaagtttaca aatgaatttt ttccgccagg atgggcccgc ggccgc                   1966
```

<210> SEQ ID NO 33
<211> LENGTH: 2950
<212> TYPE: DNA
<213> ORGANISM: Artificial sequence
<220> FEATURE:
<223> OTHER INFORMATION: TDH1-FUMR-TDH1t synthetic construct

<400> SEQUENCE: 33

```
ggatcccttc cctttttacag tgcttcggaa aagcacagcg ttgtccaagg gaacaatttt    60
tcttcaagtt aatgcataag aaatatcttt ttttatgttt agctaagtaa aagcagcttg    120
gagtaaaaaa aaaaatgagt aaatttctcg atggattagt ttctcacagg taacataaca    180
aaaaccaaga aaagcccgct tctgaaaact acagttgact tgtatgctaa agggccagac    240
taatgggagg agaaaaagaa acgaatgtat atgctcattt acactctata tcaccatatg    300
gaggataagt tgggctgagc ttctgatcca atttattcta tccattagtt gctgatatgt    360
cccaccagcc aacacttgat agtatctact cgccattcac ttccagcagc gccagtaggg    420
```

```
ttgttgagct tagtaaaaat gtgcgcacca caagcctaca tgactccacg tcacatgaaa      480
ccacaccgtg gggccttgtt gcgctaggaa taggatatgc gacgaagacg cttctgctta      540
gtaaccacac cacattttca gggggtcgat ctgcttgctt cctttactgt cacgagcggc      600
ccataatcgc gctttttttt taaaaggcgc gagacagcaa acaggaagct cgggtttcaa      660
ccttcggagt ggtcgcagat ctggagactg atctttaca atacagtaag gcaagccacc       720
atctgcttct taggtgcatg cgacggtatc cacgtgcaga acaacatagt ctgaagaagg      780
gggggaggag catgttcatt ctctgtagca gtaagagctt ggtgataatg accaaaactg      840
gagtctcgaa atcatataaa tagacaatat attttcacac aatgagattt gtagtacagt      900
tctattctct ctcttgcata aataagaaat tcatcaagaa cttggtttga tatttcacca      960
acacacacaa aaaacagtac ttcactaaat ttacacacaa acaaaatgt cctctgcttc      1020 tgctgctttg caaaaattca gagctgaaag agataccttc ggtgacttgc aagttccagc      1080
tgaccgttac tggggtgctc aaactcaaag atctttgcaa aactttgaca ttggtggtcc      1140
aactgaaaga atgccagaac cattaatcag agctttcggt gttttgaaga aggctgctgc      1200
caccgtcaac atgacctacg gtttggaccc aaaggttggt gaagccatcc aaaaggctgc      1260
tgacgaagtt atcgatggtt ctttgattga ccatttccca ttggttgtct ggcaaaccgg      1320
ttctggtact caaaccaaga tgaacgtcaa tgaagtcatc tccaacagag ccattgaatt      1380
gttgggtggt gaattaggtt ccaaggctcc agtccaccca acgatcatg tcaacatgtc      1440 tcaatcttcc aacgacactt tcccaactgc catgcacgtt gctgccgttg ttgaaattca      1500
cggtagattg attccagctt tgaccacttt gagagatgct ttgcaagcca atctgctga      1560 attcgaacac atcatcaaga ttggtagaac ccacttgcaa gatgctaccc cattgacttt      1620
aggtcaagaa ttctccggtt acactcaaca attgacctac ggtattgctc gtgttcaagg      1680
tactttggaa agattataca acttggctca aggtggtact gctgtcggta ctggtttgaa      1740
caccagaaag ggtttcgatg ccaaggttgc tgaagccatt gcttccatca ctggtttacc      1800
attcaagacc gctccaaaca aattcgaagc tttggctgct cacgacgctt tggttgaagc      1860
tcacggtgct ttgaacaccg ttgcttgttc tttgatgaag attgccaacg atatccgtta      1920
cttgggttct ggtccaagat gtggtttagg tgaattgtct ctaccagaaa acgaaccagg      1980
ttcttccatc atgccaggta aggtcaaccc aactcaatgt gaagctatga ccatggtttg      2040
tgctcaagtc atgggtaaca acactgccat ctctgttgct ggttccaacg gtcaattcga      2100
attgaatgtc tttaaaccag tcatgatcaa gaacttgatc caatccatca gattaatctc      2160
tgacgcttcc atctctttca ccaagaactg tgttgtcggt attgaagcta acgaaaagaa      2220
gatctcctcc atcatgaacg aatctttgat gttggtcact gctttgaacc ctcacattgg      2280
ttacgacaag gctgccaagt gtgccaagaa ggctcacaag gaaggtacca ctttgaaaga      2340
agctgctcta tctttgggtt acttgacctc tgaagaattc gaccaatggg ttagacctga      2400
ggacatgatt tctgccaagg attaaggccc gggcataaag caatcttgat gaggataatg      2460
attttttttt gaatatacat aaatactacc gttttctgc tagattttgt gaagacgtaa      2520
ataagtacat attactttt aagccaagac aagattaagc attaacttta cccttttctc      2580
ttctaagttt caatactagt tatcactgtt taaagttat ggcgagaacg tcggcggtta       2640
aaatatatta ccctgaacgt ggtgaattga agttctagga tggtttaaag attttccctt      2700
tttgggaaat aagtaaacaa tatattgctg cctttgcaaa acgcacatac ccacaatatg      2760
```

-continued

| | |
|---|---|
| tgactattgg caaagaacgc attatccttt gaagaggtgg atactgatac taagagagtc | 2820 |
| tctattccgg ctccactttt agtccagaga ttacttgtct tcttacgtat cagaacaaga | 2880 |
| aagcatttcc aaagtaattg catttgccct tgagcagtat atatatacta agaaggcgcg | 2940 |
| ccgcggccgc | 2950 |

<210> SEQ ID NO 34
<211> LENGTH: 5037
<212> TYPE: DNA
<213> ORGANISM: Artificial sequence
<220> FEATURE:
<223> OTHER INFORMATION: TDH3p-FRDm1-TDH3t synthetic construct

<400> SEQUENCE: 34

| | |
|---|---|
| ggatccggcg cgccctattt tcgaggacct tgtcaccttg agcccaagag agccaagatt | 60 |
| taaattttcc tatgacttga tgcaaattcc caaagctaat aacatgcaag acacgtacgg | 120 |
| tcaagaagac atatttgacc tcttaacagg ttcagacgcg actgcctcat cagtaagacc | 180 |
| cgttgaaaag aacttacctg aaaaaaacga atatatacta gcgttgaatg ttagcgtcaa | 240 |
| caacaagaag tttaatgacg cggaggccaa ggcaaaaaga ttccttgatt acgtaaggga | 300 |
| gttagaatca ttttgaataa aaaacacgct ttttcagttc gagtttatca ttatcaatac | 360 |
| tgccatttca aagaatacgt aaataattaa tagtagtgat tttcctaact ttatttagtc | 420 |
| aaaaaattag cctttttaatt ctgctgtaac ccgtacatgc ccaaaatagg gggcgggtta | 480 |
| cacagaatat ataacatcgt aggtgtctgg gtgaacagtt tattcctggc atccactaaa | 540 |
| tataatggag cccgcttttt aagctggcat ccagaaaaaa aaagaatccc agcaccaaaa | 600 |
| tattgttttc ttcaccaacc atcagttcat aggtccattc tcttagcgca actacagaga | 660 |
| acaggggcac aaacaggcaa aaaacgggca caacctcaat ggagtgatgc aacctgcctg | 720 |
| gagtaaatga tgacacaagg caattgaccc acgcatgtat ctatctcatt tcttacacc | 780 |
| ttctattacc ttctgctctc tctgatttgg aaaaagctga aaaaaaaggt tgaaaccagt | 840 |
| tccctgaaat tattccccta cttgactaat aagtatataa agacggtagg tattgattgt | 900 |
| aattctgtaa atctatttct taaacttctt aaattctact tttatagtta gtcttttttt | 960 |
| tagttttaaa acaccaagaa cttagtttcg aataaacaca cataaacaaa caaaatgggt | 1020 |
| gctgatggta tttcttctgc ttccattgtt gttactgacc cagaagctgc tgccaagaag | 1080 |
| cgtgacagaa tggccagaga attgttgtcc tccaactctg gtctatgtca agaagatgaa | 1140 |
| ccaaccatca tcaacttaaa gggttttggaa cacaccattc catacagatt ggccgttgtt | 1200 |
| ttgtgtaact ccagatccac tggtgaattc gaagccaagg ctgctgaaat cttgagaaag | 1260 |
| gctttccaca tggttgacta ctcttttgaat tgtttcaacc cagaatctga attgtcccgt | 1320 |
| gtcaactctt taccagtcgg tgaaaagcac caaatgtccg aagatctaag acatgtcatg | 1380 |
| gaatgtacca tttctgtcca ccactcctct ggtatgggtt tcgacccagc tgctggtcca | 1440 |
| atcatctcca gattgagagg tgccatgaga atcacaacg acatgtccga tatctccgtc | 1500 |
| actgaagctg aagttgaatt attctctttg gctcaatctt tcgatgtcga cttggaagaa | 1560 |
| ggtactattg ccagaaagca ctctgaagcc agattggatt gggtggtgt caacaagggt | 1620 |
| tacactgttg actacgttgt tgaccatttg agagctgctg gtatgccaaa cgtcttgttc | 1680 |
| gaatggggtg tgatatcag agcttctggt agaaacatca agggtaactt gtgggctgtt | 1740 |
| gccatcaagc gtccaccatc tgttgaagaa gttatccgtc gtgccaaggg taagatgtta | 1800 |
| aagatgggtg aagaagaaca agaagaaaag gacgatgact ctccatcttt gttgcacgtt | 1860 |

-continued

```
gttgaattgg atgacgaagc tttgtgtacc tctggtgact acgaaaacgt cttataccat    1920
ccaaagcacg gtgttgctgg ttccattttc gactggcaac gtcgtggttt attgtctcca    1980
gaagaaggtg ctttagctca agtttccgtc aaatgttact ctgccatgta cgctgatgct    2040
ttggccactg tttgtttggt caagagagat gctgtcagaa tcagatactt gttggaaggt    2100
tggagatacg tcagatctcg tgtcaccaac tacttcgctt acaccagaca aggtgaaaga    2160
ttggctcaca tgcacgaaat tgctcaagaa accagagaat aagagaaat cagaattgct     2220 ggttctttgc catccagaat tgttatcgtc ggtggtggtt tggctggtct atccgctgcc    2280
attgaagctg cttcttgtgg tgctcaagtc attttgatgg aaaaggaagg tagaattggt    2340
ggtaactctg ccaaggctac ctctggtatc aacggttggg gtaccagaac ccaagccaag    2400
tctgatatct tggatggtgg taagtacttt gaaagagaca ctttcttgtc cggtgtcggt    2460
ggtaccactg acccagcttt ggtcaaggtc ttgtccgtca aatctggtga cgctatcggt    2520
tggttaactt ctttgggtgt cccattgtcc gttttgtctc aattgggtgg tcactctttc    2580
aagagaactc acagagctcc agacaagact gatggtactc cattaccaat tggtcacacc    2640
atcatgagaa ctttggaaga tcatatcaga aacaacttgt ctgaaagagt taccatcatg    2700
acccacgttt ctgttactga attgttgcac gaaactgaca ccactccaga tggtgcttct    2760
gaagttcgtg tcaccggtgt ccgttacaga gacttgtctg atgtcgatgg tcaaccttcc    2820
aaactattgg ctgacgctgt tgttttggcc actggtggtt ctccaacga cagagaagaa    2880 aactctttgt tgtgtaaata cgctcctcat ttggcttctt tcccaactac caacggtcca    2940
tgggctactg gtgacggtgt caaattggcc acctccgttg gtgccaagtt ggttgacatg    3000
gacaaggttc aattgcaccc aactggtttg attgacccaa aggacccagc taacaccact    3060
aagatcttgg gtccagaagc tttgagaggt tctggtggta ttttgttgaa caagcaaggt    3120
aagagattcg tcaacgaatt ggacttgaga tccgttgttt ccaaggccat taacactcaa    3180
ggtaacgaat acccaggttc tggtggttgt tactttgctt actgtgtctt aaacgaagat    3240
gctaccaact tattctgtgg tggtgctttg ggtttctacg gtaagaaatt aggtttgttc    3300
caaagagctg aaactgttga agaattggcc aaattgattg ttgtgacga aggtgaattg     3360 agagacactt ggaaaaaata cgaaacctgt tccaaggcca aggttgcttg tccagtcact    3420
ggtaaggttg ttttcccatg tgttgtcggt accgagggtc catacaatgt tgctttcgtc    3480
actccatcca tccactacac catgggtggt tgtttgatct ctccagctgc tgaagtcttg    3540
caagaataca agggtttgaa tatcttggaa accacagac caatcagatg tttgttcggt     3600
gctggtgaag tcactggtgg tgtccacggt ggtaacagat aggtggtaa ctctctattg     3660 gaatgtgttc tctttggtaa gattgctggt gacagagctg ccactatctt gcaaaagaga    3720
gaaattgctt tgtccaagac ctcctggacc tctgttgttg tcagagaatc cagatctggt    3780
gaacaattcg gtaccggttc cagagttttg agattcaact tgccaggtgc tttacaaaga    3840
accggtttga acttgggtga attcgttgcc atcagaggtg aatgggatgg tcaacaatta    3900
gtcggttact tctctccaat cacttttgcca gaagatttgg gtaccatctc tttgttggtc    3960
agagctgaca agggtacttt gaaggaatgg atctgtgctt tgcgtccagg tgactccgtt    4020
gaaatcaagg cttgtggtgg tctaagaatt gaccaagatc cagtcaagaa atgtttgttg    4080
ttcagaaaca gaccaattac cagatttgct ttggttgctg ctggtaccgg tgttgctcca    4140
atgttgcaag ttatcagagc tgctttgaag aagccatacg tcgacacttt ggaatccatc    4200
```

```
agattgatct acgctgctga agaatatgac actttaacct acagatctat cttgcaaaga    4260
tttgctgaag aattcccaga caaattcgtt tgtaacttcg tcttaaacaa ccctccagaa    4320
ggttggaccg gtggtgttgg tttcgtcaac aagaaatctt tgcaaaaggt tttgcaacca    4380
ccttcttctg aaccattgat tgttgtttgt ggtccacctg ttatgcaaag agatgtcaaa    4440
aatgaattgt tgtccatggg ttacgacaag gaattggttc acactgtcga tggtgaatct    4500
ggtaccttgt aaggcccggg cgtgaattta ctttaaatct tgcattaaaa taaattttct    4560
ttttatagct ttatgactta gtttcaattt atatactatt ttaatgacat tttcgattca    4620
ttgattgaaa gctttgtgtt tttcttgat gcgctattgc attgttcttg tcttttttcgc    4680 cacatgtaat atctgtagta gataccgat acattgtgga tgctgagtga aatttagtt    4740 aataatggag gcgctcttaa taattttggg gatattggct tttttttta aagtttacaa    4800 atgaattttt tccgccagga taacgattct gaagttactc ttagcgttcc tatcggtaca    4860
gccatcaaat catgcctata aatcatgcct atatttgcgt gcagtcagta tcatctacat    4920
gaaaaaaact cccgcaattt cttatagaat acgttgaaaa ttaaatgtac gcgccaagat    4980
aagataacat atatctagat gcagtaatat acacagattc cggccggccg cggccgc      5037

<210> SEQ ID NO 35
<211> LENGTH: 4959
<212> TYPE: DNA
<213> ORGANISM: Artificial Sequence
<220> FEATURE:
<223> OTHER INFORMATION: TDH3p-FRDg-TDH3t artificial sequence

<400> SEQUENCE: 35
ggatccggcg cgccctattt tcgaggacct tgtcaccttg agcccaagag agccaagatt      60
taaattttcc tatgacttga tgcaaattcc caaagctaat aacatgcaag acacgtacgg     120
tcaagaagac atatttgacc tcttaacagg ttcagacgcg actgcctcat cagtaagacc     180
cgttgaaaag aacttacctg aaaaaaacga atatatacta gcgttgaatg ttagcgtcaa     240
caacaagaag tttaatgacg cggaggccaa ggcaaaaaga ttccttgatt acgtaaggga     300
gttagaatca ttttgaataa aaaacacgct ttttcagttc gagtttatca ttatcaatac     360
tgccatttca agaatacgt aaataattaa tagtagtgat tttcctaact ttatttagtc      420
aaaaaattag ccttttaatt ctgctgtaac ccgtacatgc ccaaaatagg gggcgggtta     480
cacagaatat ataacatcgt aggtgtctgg gtgaacagtt tattcctggc atccactaaa     540
tataatggag cccgcttttt aagctggcat ccagaaaaaa aaagaatccc agcaccaaaa     600
tattgttttc ttcaccaacc atcagttcat aggtccattc tcttagcgca actacagaga     660 acagggggcac aaacaggcaa aaaacgggca caacctcaat ggagtgatgc aacctgcctg     720
gagtaaatga tgacacaagg caattgaccc acgcatgtat ctatctcatt tcttacacc      780 ttctattacc ttctgctctc tctgatttgg aaaaagctga aaaaaaggt tgaaaccagt     840 tccctgaaat tattccccta cttgactaat aagtatataa agacggtagg tattgattgt     900
aattctgtaa atctatttct taaacttctt aaattctact tttatagtta gtcttttttt     960
tagttttaaa acaccaagaa cttagtttcg aataaacaca cataaacaaa caaaatggtt    1020
gatggtagat cttctgcttc cattgttgcc gttgacccag aaagagctgc cagagaaaga    1080
gatgctgctg ccagagcttt gttgcaagac tctccattgc acaccaccat gcaatacgct    1140
acctctggtt tggaattgac tgttccatac gctttgaagg ttgttgcttc tgctgacact    1200
ttcgacagag ccaaggaagt tgctgatgaa gtcttgagat gtgcctggca attggctgac    1260
```

```
accgttttga actctttcaa cccaaactct gaagtctctt tagtcggtag attaccagtc    1320
ggtcaaaagc atcaaatgtc tgctccattg aaacgtgtca tggcttgttg tcaaagagtc    1380
tacaactcct ctgctggttg tttcgaccca tccactgctc cagttgccaa ggctttgaga    1440
gaaattgctt tgggtaagga aagaaacaat gcttgtttgg aagctttgac tcaagcttgt    1500
accttgccaa actctttcgt cattgatttc gaagctggta ctatctccag aaagcacgaa    1560
cacgcttctt tggatttggg tggtgtttcc aagggttaca tcgtcgatta cgtcattgac    1620
aacatcaatg ctgctggttt ccaaaacgtt tctttgact ggggtggtga ctgtcgtgcc    1680
tccggtatga acgccagaaa cactccatgg gttgtcggta tcactagacc tccttccttg    1740
gacatgttgc caaaccctcc aaaggaagct tcttacatct ccgtcatctc tttggacaat    1800
gaagctttgg ctacctctgg tgattacgaa aacttgatct acactgctga cgataaacca    1860
ttgacctgta cctacgattg gaaaggtaag gaattgatga agccatctca atccaatatc    1920
gctcaagttt ccgtcaagtg ttactctgcc atgtacgctg acgctttggc taccgcttgt    1980
ttcatcaagc gtgacccagc caaggtcaga caattgttgg atggttggag atacgttaga    2040
gacaccgtca gagattaccg tgtctacgtc agagaaaacg aaagagttgc caagatgttc    2100
gaaattgcca ctgaagatgc tgaaatgaga agagaagaa tttccaacac tttaccagct    2160
cgtgtcattg ttgttggtgg tggtttggct ggtttgtccg ctgccattga agctgctggt    2220
tgtggtgctc aagttgtttt gatggaaaag gaagccaagt tgggtggtaa ctctgccaag    2280
gctacctctg gtatcaacgg ttggggtact agagctcaag ctaaggcttc cattgtcgat    2340
ggtggtaagt acttcgaaag agatacctac aagtctggta tcggtggtaa caccgatcca    2400
gctttggtta agactttgtc catgaaatct gctgacgcta tcggttggtt gacttctcta    2460
ggtgttccat tgactgtttt gtcccaatta ggtggtcact ccagaaagag aactcacaga    2520
gctccagaca agaaggatgg tactccattg ccaattggtt tcaccatcat gaaaacttta    2580
gaagatcatg ttagaggtaa cttgtccggt agaatcacca tcatggaaaa ctgttccgtt    2640
acctctttgt tgtctgaaac caaggaaaga ccagacggta ccaagcaaat cagagttacc    2700
ggtgtcgaat tcactcaagc tggttctggt aagaccacca ttttggctga tgctgttatc    2760
ttggccaccg gtggtttctc caacgacaag actgctgatt ctttgttgag agaacatgcc    2820
ccacacttgg ttaacttccc aaccaccaac ggtccatggg ctactggtga tggtgtcaag    2880
ttggctcaaa gattaggtgc tcaattggtc gatatggaca aggttcaatt gcacccaact    2940
ggtttgatca acccaaagga cccagccaac ccaaccaaat tcttgggtcc agaagctcta    3000
agaggttctg gtgtgttttt gttgaacaaa caaggtaaga gatttgtcaa cgaattggat    3060
ttgagatctg ttgtttccaa ggccatcatg aacaaggtg ctgaataccc aggttctggt    3120
ggttccatgt ttgcttactg tgtcttgaac gctgctgctc aaaaattgtt tggtgtttcc    3180
tctcacgaat ctactggaa gaagatgggt ttgttcgtca aggctgacac catgagagac    3240
ttggctgctt tgattggttg tccagttgaa tccgttcaac aaactttaga agaatacgaa    3300
agattatcca tctctcaaag atcttgtcca attaccagaa atctgtttta cccatgtgtt    3360
ttgggtacca aaggtccata ctatgtcgcc tttgtcactc catctatcca ctacaccatg    3420
ggtggttgtt tgatttctcc atctgctgaa atccaaatga gaacacttc ttccagagct    3480
ccattgtccc actccaaccc aatcttgggt ttattcggtg ctggtgaagt caccggtggt    3540
gtccacggtg gtaacagatt aggtggtaac tctttgttgg aatgtgttgt tttcggtaga    3600
```

```
attgccggtg acagagcttc taccattttg caaagaaagt cctctgcttt gtctttcaag    3660
gtctggacca ctgttgtttt gagagaagtc agagaaggtg gtgtctacgg tgctggttcc    3720
cgtgtcttga gattcaactt accaggtgct ctacaaagat ctggtctatc cttgggtcaa    3780
ttcattgcca tcagaggtga ctgggacggt caacaattga ttggttacta ctctccaatc    3840
actttgccag acgatttggg tatgattgac attttggcca gatctgacaa gggtacttta    3900
cgtgaatgga tctctgcttt ggaaccaggt gacgctgtcg aaatgaaggc ttgtggtggt    3960
ttggtcatcg aaagaagatt atctgacaag cacttcgttt tcatgggtca cattatcaac    4020
aagctatgtt tgattgctgg tggtaccggt gttgctccaa tgttgcaaat catcaaggcc    4080
gctttcatga agccattcat cgacactttg aatccgtcc acttgatcta cgctgctgaa    4140
gatgtcactg aattgactta cagagaagtt ttggaagaac gtcgtcgtga atccagaggt    4200
aaattcaaga aactttcgt tttgaacaga cctcctccat tatggactga cggtgtcggt    4260
ttcatcgacc gtggtatctt gaccaaccac gttcaaccac catctgacaa cttattggtt    4320
gccatctgtg gtccaccagt tatgcaaaga attgtcaagg ccactttaaa gactttaggt    4380
tacaacatga acttggtcag aaccgttgac gaaactgaac catctggaag ttaaggcccg    4440
ggcgtgaatt tactttaaat cttgcattta aataaatttt cttttatag ctttatgact    4500
tagtttcaat ttatatacta tttaatgac attttcgatt cattgattga aagctttgtg    4560
tttttttcttg atgcgctatt gcattgttct tgtcttttc gccacatgta atatctgtag    4620
tagatacctg atacattgtg gatgctgagt gaaatttag ttaataatgg aggcgctctt    4680
aataattttg gggatattgg cttttttttt taaagtttac aaatgaattt tttccgccag    4740
gataacgatt ctgaagttac tcttagcgtt cctatcggta cagccatcaa atcatgccta    4800
taaatcatgc ctatatttgc gtgcagtcag tatcatctac atgaaaaaaa ctcccgcaat    4860
ttcttataga atacgttgaa aattaaatgt acgcgccaag ataagataac atatatctag    4920
atgcagtaat atacacagat tccggccggc cgcggccgc                           4959
```

<210> SEQ ID NO 36
<211> LENGTH: 438
<212> TYPE: PRT
<213> ORGANISM: Schizosaccharomyces pombe

<400> SEQUENCE: 36

```
Met Gly Glu Leu Lys Glu Ile Leu Lys Gln Arg Tyr His Glu Leu Leu
1               5                   10                  15

Asp Trp Asn Val Lys Ala Pro His Val Pro Leu Ser Gln Arg Leu Lys
            20                  25                  30

His Phe Thr Trp Ser Trp Phe Ala Cys Thr Met Ala Thr Gly Gly Val
        35                  40                  45

Gly Leu Ile Ile Gly Ser Phe Pro Phe Arg Phe Tyr Gly Leu Asn Thr
    50                  55                  60

Ile Gly Lys Ile Val Tyr Ile Leu Gln Ile Phe Leu Phe Ser Leu Phe
65                  70                  75                  80

Gly Ser Cys Met Leu Phe Arg Phe Ile Lys Tyr Pro Ser Thr Ile Lys
                85                  90                  95

Asp Ser Trp Asn His His Leu Glu Lys Leu Phe Ile Ala Thr Cys Leu
            100                 105                 110

Leu Ser Ile Ser Thr Phe Ile Asp Met Leu Ala Ile Tyr Ala Tyr Pro
        115                 120                 125

Asp Thr Gly Glu Trp Met Val Trp Val Arg Ile Leu Tyr Tyr Ile
```

Tyr Val Ala Val Ser Phe Ile Tyr Cys Val Met Ala Phe Phe Thr Ile
145                 150                 155                 160

Phe Asn Asn His Val Tyr Thr Ile Glu Thr Ala Ser Pro Ala Trp Ile
                165                 170                 175

Leu Pro Ile Phe Pro Pro Met Ile Cys Gly Val Ile Ala Gly Ala Val
            180                 185                 190

Asn Ser Thr Gln Pro Ala His Gln Leu Lys Asn Met Val Ile Phe Gly
        195                 200                 205

Ile Leu Phe Gln Gly Leu Gly Phe Trp Val Tyr Leu Leu Leu Phe Ala
    210                 215                 220

Val Asn Val Leu Arg Phe Phe Thr Val Gly Leu Ala Lys Pro Gln Asp
225                 230                 235                 240

Arg Pro Gly Met Phe Met Phe Val Gly Pro Pro Ala Phe Ser Gly Leu
                245                 250                 255

Ala Leu Ile Asn Ile Ala Arg Gly Ala Met Gly Ser Arg Pro Tyr Ile
                260                 265                 270

Phe Val Gly Ala Asn Ser Ser Glu Tyr Leu Gly Phe Val Ser Thr Phe
            275                 280                 285

Met Ala Ile Phe Ile Trp Gly Leu Ala Ala Trp Cys Tyr Cys Leu Ala
    290                 295                 300

Met Val Ser Phe Leu Ala Gly Phe Phe Thr Arg Ala Pro Leu Lys Phe
305                 310                 315                 320

Ala Cys Gly Trp Phe Ala Phe Ile Phe Pro Asn Val Gly Phe Val Asn
                325                 330                 335

Cys Thr Ile Glu Ile Gly Lys Met Ile Asp Ser Lys Ala Phe Gln Met
                340                 345                 350

Phe Gly His Ile Ile Gly Val Ile Leu Cys Ile Gln Trp Ile Leu Leu
            355                 360                 365

Met Tyr Leu Met Val Arg Ala Phe Leu Val Asn Asp Leu Cys Tyr Pro
    370                 375                 380

Gly Lys Asp Glu Asp Ala His Pro Pro Lys Pro Asn Thr Gly Val
385                 390                 395                 400

Leu Asn Pro Thr Phe Pro Pro Glu Lys Ala Pro Ala Ser Leu Glu Lys
                405                 410                 415

Val Asp Thr His Val Thr Ser Thr Gly Gly Glu Ser Pro Pro Ser
                420                 425                 430

Ser Glu His Glu Ser Val
        435

<210> SEQ ID NO 37
<211> LENGTH: 1317
<212> TYPE: DNA
<213> ORGANISM: Artificial sequence
<220> FEATURE:
<223> OTHER INFORMATION: S. pombe malae permease cpo for S. cerevisiae

<400> SEQUENCE: 37
atgggtgaat tgaaggaaat cttgaagcaa cgttaccatg aattgttgga ctggaacgtc     60
aaggctccac acgttccatt gtctcaaaga ttgaagcatt tcacctggtc ctggtttgct    120
tgtaccatgg ccactggtgg tgtcggtttg atcattggtt ctttcccatt cagattctac    180
ggtttgaaca ccattggtaa gattgtctac atcttacaaa tcttcttatt ctctttgttt    240
ggttcttgta tgttgttcag attcatcaaa tacccatcta ccatcaagga ctcctggaac    300

```
caccacttgg aaaaattatt cattgctacc tgtttgctat ccatctccac tttcattgac    360
atgttggcca tctacgctta cccagacact ggtgaatgga tggtctgggt tatcagaatc    420
ttatactaca tctacgttgc tgtctctttc atctactgtg tcatggcttt cttcaccatt    480
ttcaacaacc acgtttacac cattgaaact gcttctccag cttggatctt accaattttc    540
ccaccaatga tctgtggtgt cattgctggt gctgtcaact ccactcaacc agctcaccaa    600
ttgaagaaca tggttatctt cggtatctta ttccaaggtt tgggtttctg ggttacttg     660 ttgttgtttg ctgtcaacgt tttgagattc ttcaccgttg gtttggccaa gcctcaagac    720
agaccaggta tgttcatgtt tgttggtcca ccagctttct ccggtttggc tttgatcaac    780
attgcccgtg gtgctatggg ttccagacca tacattttcg tcggtgccaa ttcttctgaa    840
tacttgggtt tcgttccac tttcatggcc attttcatct ggggtttggc tgcttggtgt     900
tactgtttgg ccatggtttc tttcttggct ggtttcttca ccagagctcc attgaaattt   960
gcttgtggtt ggtttgcttt catcttccca aacgtcggtt tcgttaactg taccattgaa   1020
attggtaaga tgattgactc caaggccttc caaatgttcg gtcacatcat cggtgtcatc   1080
ctatgtatcc aatggatctt gttgatgtac ttgatggtca gagctttctt ggtcaacgat   1140
ttgtgttacc caggtaagga tgaagatgct cacccacctc caaagccaaa cactggtgtt   1200
ttgaacccaa ctttcccacc agaaaaggct ccagcttctt tggaaaaggt tgacacccac   1260
gttacttcca ctggtggtga atctgatcct ccatcttctg aacacgaaag cgtttaa      1317

<210> SEQ ID NO 38
<211> LENGTH: 600
<212> TYPE: DNA
<213> ORGANISM: Artificial sequence
<220> FEATURE:
<223> OTHER INFORMATION: ENO1 promotor T at position -5 was changed to A
      in order to obtain a better Kozak sequence

<400> SEQUENCE: 38
ccgcggaacc gccagatatt cattacttga cgcaaaagcg tttgaaataa tgacgaaaaa     60
gaaggaagaa aaaaaagaa aaataccgct tctaggcggg ttatctactg atccgagctt    120
ccactaggat agcacccaaa cacctgcata tttggacgac ctttacttac accaccaaaa    180
accactttcg cctctcccgc ccctgataac gtccactaat tgagcgatta cctgagcggt    240 cctctttgt ttgcagcatg agacttgcat actgcaaatc gtaagtagca acgtctcaag    300
gtcaaaactg tatggaaacc ttgtcacctc acttaattct agctagccta ccctgcaagt    360
caagaggtct ccgtgattcc tagccaccct aaggtatgcc tctccccgga aactgtggcc    420
ttttctggca cacatgatct ccacgatttc aacatataaa tagcttttga taatggcaat    480
attaatcaaa tttattttac ttctttcttg taacatctct cttgtaatcc cttattcctt    540
ctagctattt ttcataaaaa accaagcaac tgcttatcaa cacacaaaca ctaaaacaaa    600

<210> SEQ ID NO 39
<211> LENGTH: 300
<212> TYPE: DNA
<213> ORGANISM: Artificial sequence
<220> FEATURE:
<223> OTHER INFORMATION: ENO1 terminator

<400> SEQUENCE: 39
agcttttgat taagccttct agtccaaaaa acacgttttt ttgtcattta tttcattttc     60
ttagaatagt ttagttttatt catttttatag tcacgaatgt tttatgattc tatatagggt   120
```

```
tgcaaacaag cattttttcat tttatgttaa aacaatttca ggtttacctt ttattctgct      180
tgtggtgacg cgggtatccg cccgctcttt tggtcaccca tgtatttaat tgcataaata      240
attcttaaaa gtggagctag tctatttcta tttacatacc tctcatttct catttcctcc      300
```

<210> SEQ ID NO 40
<211> LENGTH: 2240
<212> TYPE: DNA
<213> ORGANISM: Artificial sequence
<220> FEATURE:
<223> OTHER INFORMATION: ENO1p-SpMAE-ENO1t synthetic construct

<400> SEQUENCE: 40

```
ggatccggcg cgccccgcgg aaccgccaga tattcattac ttgacgcaaa agcgtttgaa       60
ataatgacga aaagaaggaa agaaaaaaaa agaaaaatac cgcttctagg cgggttatct      120
actgatccga gcttccacta ggatagcacc caaacacctg catatttgga cgacctttac      180
ttacaccacc aaaaaccact ttcgcctctc ccgcccctga taacgtccac taattgagcg      240
attacctgag cggtcctctt tgtttgcag catgagactt gcatactgca atcgtaagt        300 agcaacgtct caaggtcaaa actgtatgga aaccttgtca cctcacttaa ttctagctag      360
cctaccctgc aagtcaagag gtctccgtga ttcctagcca cctcaaggta tgcctctccc      420
cggaaactgt ggcctttct ggcacacatg atctccacga tttcaacata taaatagctt      480
ttgataatgg caatattaat caaatttatt ttacttcttt cttgtaacat ctctcttgta      540
atcccttatt ccttctagct attttttcata aaaaccaag caactgctta tcaacacaca      600
aacactaaaa caaaatgggt gaattgaagg aaatcttgaa gcaacgttac catgaattgt      660
tggactggaa cgtcaaggct ccacacgttc cattgtctca aagattgaag catttcacct      720
ggtcctggtt tgcttgtacc atggccactg gtggtgtcgg tttgatcatt ggttctttcc      780
cattcagatt ctacggtttg aacaccattg gtaagattgt ctacatctta caaatcttct      840
tattctcttt gtttggttct tgtatgttgt tcagattcat caaatacccca tctaccatca      900 aggactcctg gaaccaccac ttggaaaaat tattcattgc tacctgtttg ctatccatct      960
ccactttcat tgacatgttg gccatctacg cttacccaga cactggtgaa tggatggtct     1020
gggttatcag aatcttatac tacatctacg ttgctgtctc tttcatctac tgtgtcatgg     1080
ctttcttcac cattttcaac aaccacgttt acaccattga aactgcttct ccagcttgga     1140
tcttaccaat tttcccacca atgatctgtg tgtcattgc tggtgctgtc aactccactc     1200
aaccagctca ccaattgaag aacatggtta tcttcggtat cttattccaa ggtttgggtt     1260
tctgggttta cttgttgttg tttgctgtca acgttttgag attcttcacc gttggtttgg     1320
ccaagcctca agacagacca ggtatgttca tgtttgttgg tccaccagct ttctccggtt     1380
tggctttgat caacattgcc cgtggtgcta tgggttccag accatacatt ttcgtcggtg     1440
ccaattcttc tgaatacttg ggtttcgttt ccactttcat ggccattttc atctgggggtt     1500 tggctgcttg tgttactgt ttggccatgg tttctttctt ggctggtttc ttcaccagag     1560
ctccattgaa atttgcttgt ggttggtttg ctttcatctt cccaaacgtc ggtttcgtta     1620
actgtaccat tgaaattggt aagatgattg actccaaggc cttccaaatg ttcggtcaca     1680
tcatcggtgt catcctatgt atccaatgga tcttgttgat gtacttgatg gtcagagctt     1740
tcttggtcaa cgatttgtgt tacccaggta aggatgaaga tgctcaccca cctccaaagc     1800
caaacactgg tgttttgaac ccaacttttcc caccagaaaa ggctccagct tctttggaaa     1860
aggttgacac ccacgttact tccactggtg ggtgaatctga tcctccatct tctgaacacg     1920
```

```
aaagcgttta agagcttttg attaagcctt ctagtccaaa aaacacgttt ttttgtcatt    1980
tatttcattt tcttagaata gtttagttta ttcattttat agtcacgaat gttttatgat    2040
tctatatagg gttgcaaaca agcatttttc attttatgtt aaaacaattt caggtttacc    2100
ttttattctg cttgtggtga cgcgggtatc cgcccgctct tttggtcacc catgtattta    2160
attgcataaa taattcttaa aagtggagct agtctatttc tatttacata cctctcattt    2220
ctcatttcct ccgcggccgc                                                2240

<210> SEQ ID NO 41
<211> LENGTH: 1180
<212> TYPE: PRT
<213> ORGANISM: Saccharomyces cerevisiae

<400> SEQUENCE: 41
```

Met Ser Ser Ser Lys Lys Leu Ala Gly Leu Arg Asp Asn Phe Ser Leu
1               5                   10                  15

Leu Gly Glu Lys Asn Lys Ile Leu Val Ala Asn Arg Gly Glu Ile Pro
            20                  25                  30

Ile Arg Ile Phe Arg Ser Ala His Glu Leu Ser Met Arg Thr Ile Ala
        35                  40                  45

Ile Tyr Ser His Glu Asp Arg Leu Ser Met His Arg Leu Lys Ala Asp
    50                  55                  60

Glu Ala Tyr Val Ile Gly Glu Glu Gly Gln Tyr Thr Pro Val Gly Ala
65                  70                  75                  80

Tyr Leu Ala Met Asp Glu Ile Ile Glu Ile Ala Lys Lys His Lys Val
                85                  90                  95

Asp Phe Ile His Pro Gly Tyr Gly Phe Leu Ser Glu Asn Ser Glu Phe
            100                 105                 110

Ala Asp Lys Val Val Lys Ala Gly Ile Thr Trp Ile Gly Pro Pro Ala
        115                 120                 125

Glu Val Ile Asp Ser Val Gly Asp Lys Val Ser Ala Arg His Leu Ala
    130                 135                 140

Ala Arg Ala Asn Val Pro Thr Val Pro Gly Thr Pro Gly Pro Ile Glu
145                 150                 155                 160

Thr Val Gln Glu Ala Leu Asp Phe Val Asn Glu Tyr Gly Tyr Pro Val
                165                 170                 175

Ile Ile Lys Ala Ala Phe Gly Gly Gly Gly Arg Gly Met Arg Val Val
            180                 185                 190

Arg Glu Gly Asp Asp Val Ala Asp Ala Phe Gln Arg Ala Thr Ser Glu
        195                 200                 205

Ala Arg Thr Ala Phe Gly Asn Gly Thr Cys Phe Val Glu Arg Phe Leu
    210                 215                 220

Asp Lys Pro Lys His Ile Glu Val Gln Leu Leu Ala Asp Asn His Gly
225                 230                 235                 240

Asn Val Val His Leu Phe Glu Arg Asp Cys Ser Val Gln Arg Arg His
                245                 250                 255

Gln Lys Val Val Glu Val Ala Pro Ala Lys Thr Leu Pro Arg Glu Val
            260                 265                 270

Arg Asp Ala Ile Leu Thr Asp Ala Val Lys Leu Ala Lys Val Cys Gly
        275                 280                 285

Tyr Arg Asn Ala Gly Thr Ala Glu Phe Leu Val Asp Asn Gln Asn Arg
    290                 295                 300

His Tyr Phe Ile Glu Ile Asn Pro Arg Ile Gln Val Glu His Thr Ile

```
             305                 310                 315                 320
Thr Glu Glu Ile Thr Gly Ile Asp Ile Val Ser Ala Gln Ile Gln Ile
                 325                 330                 335
Ala Ala Gly Ala Thr Leu Thr Gln Leu Gly Leu Leu Gln Asp Lys Ile
                 340                 345                 350
Thr Thr Arg Gly Phe Ser Ile Gln Cys Arg Ile Thr Thr Glu Asp Pro
                 355                 360                 365
Ser Lys Asn Phe Gln Pro Asp Thr Gly Arg Leu Glu Val Tyr Arg Ser
                 370                 375                 380
Ala Gly Gly Asn Gly Val Arg Leu Asp Gly Gly Asn Ala Tyr Ala Gly
385                 390                 395                 400
Ala Thr Ile Ser Pro His Tyr Asp Ser Met Leu Val Lys Cys Ser Cys
                 405                 410                 415
Ser Gly Ser Thr Tyr Glu Ile Val Arg Arg Lys Met Ile Arg Ala Leu
                 420                 425                 430
Ile Glu Phe Arg Ile Arg Gly Val Lys Thr Asn Ile Pro Phe Leu Leu
                 435                 440                 445
Thr Leu Leu Thr Asn Pro Val Phe Ile Glu Gly Thr Tyr Trp Thr Thr
                 450                 455                 460
Phe Ile Asp Asp Thr Pro Gln Leu Phe Gln Met Val Ser Ser Gln Asn
465                 470                 475                 480
Arg Ala Gln Lys Leu Leu His Tyr Leu Ala Asp Leu Ala Val Asn Gly
                 485                 490                 495
Ser Ser Ile Lys Gly Gln Ile Gly Leu Pro Lys Leu Lys Ser Asn Pro
                 500                 505                 510
Ser Val Pro His Leu His Asp Ala Gln Gly Asn Val Ile Asn Val Thr
                 515                 520                 525
Lys Ser Ala Pro Pro Ser Gly Trp Arg Gln Val Leu Glu Lys Gly
                 530                 535                 540
Pro Ser Glu Phe Ala Lys Gln Val Arg Gln Phe Asn Gly Thr Leu Leu
545                 550                 555                 560
Met Asp Thr Thr Trp Arg Asp Ala His Gln Ser Leu Leu Ala Thr Arg
                 565                 570                 575
Val Arg Thr His Asp Leu Ala Thr Ile Ala Pro Thr Thr Ala His Ala
                 580                 585                 590
Leu Ala Gly Ala Phe Ala Leu Glu Cys Trp Gly Gly Ala Thr Phe Asp
                 595                 600                 605
Val Ala Met Arg Phe Leu His Glu Asp Pro Trp Glu Arg Leu Arg Lys
                 610                 615                 620
Leu Arg Ser Leu Val Pro Asn Ile Pro Phe Gln Met Leu Leu Arg Gly
625                 630                 635                 640
Ala Asn Gly Val Ala Tyr Ser Ser Leu Pro Asp Asn Ala Ile Asp His
                 645                 650                 655
Phe Val Lys Gln Ala Lys Asp Asn Gly Val Asp Ile Phe Arg Val Phe
                 660                 665                 670
Asp Ala Leu Asn Asp Leu Glu Gln Leu Lys Val Gly Val Asn Ala Val
                 675                 680                 685
Lys Lys Ala Gly Gly Val Val Glu Ala Thr Val Cys Tyr Ser Gly Asp
                 690                 695                 700
Met Leu Gln Pro Gly Lys Lys Tyr Asn Leu Asp Tyr Tyr Leu Glu Val
705                 710                 715                 720
Val Glu Lys Ile Val Gln Met Gly Thr His Ile Leu Gly Ile Lys Asp
                 725                 730                 735
```

```
Met Ala Gly Thr Met Lys Pro Ala Ala Ala Lys Leu Leu Ile Gly Ser
            740                 745                 750
Leu Arg Thr Arg Tyr Pro Asp Leu Pro Ile His Val His Ser His Asp
            755                 760                 765
Ser Ala Gly Thr Ala Val Ala Ser Met Thr Ala Cys Ala Leu Ala Gly
            770                 775                 780
Ala Asp Val Val Asp Val Ala Ile Asn Ser Met Ser Gly Leu Thr Ser
785                 790                 795                 800
Gln Pro Ser Ile Asn Ala Leu Leu Ala Ser Leu Glu Gly Asn Ile Asp
            805                 810                 815
Thr Gly Ile Asn Val Glu His Val Arg Glu Leu Asp Ala Tyr Trp Ala
            820                 825                 830
Glu Met Arg Leu Leu Tyr Ser Cys Phe Glu Ala Asp Leu Lys Gly Pro
            835                 840                 845
Asp Pro Glu Val Tyr Gln His Glu Ile Pro Gly Gly Gln Leu Thr Asn
            850                 855                 860
Leu Leu Phe Gln Ala Gln Gln Leu Gly Leu Gly Gln Trp Ala Glu
865                 870                 875                 880
Thr Lys Arg Ala Tyr Arg Glu Ala Asn Tyr Leu Leu Gly Asp Ile Val
            885                 890                 895
Lys Val Thr Pro Thr Ser Lys Val Val Gly Asp Leu Ala Gln Phe Met
            900                 905                 910
Val Ser Asn Lys Leu Thr Ser Asp Asp Ile Arg Arg Leu Ala Asn Ser
            915                 920                 925
Leu Asp Phe Pro Asp Ser Val Met Asp Phe Phe Glu Gly Leu Ile Gly
            930                 935                 940
Gln Pro Tyr Gly Gly Phe Pro Glu Pro Leu Arg Ser Asp Val Leu Arg
945                 950                 955                 960
Asn Lys Arg Arg Lys Leu Thr Cys Arg Pro Gly Leu Glu Leu Glu Pro
            965                 970                 975
Phe Asp Leu Glu Lys Ile Arg Glu Asp Leu Gln Asn Arg Phe Gly Asp
            980                 985                 990
Ile Asp Glu Cys Asp Val Ala Ser Tyr Asn Met Tyr Pro Arg Val Tyr
            995                 1000                1005
Glu Asp Phe Gln Lys Ile Arg Glu Thr Tyr Gly Asp Leu Ser Val
            1010                1015                1020
Leu Pro Thr Lys Asn Phe Leu Ala Pro Ala Glu Pro Asp Glu Glu
            1025                1030                1035
Ile Glu Val Thr Ile Glu Gln Gly Lys Thr Leu Ile Ile Lys Leu
            1040                1045                1050
Gln Ala Val Gly Asp Leu Asn Lys Lys Thr Gly Gln Arg Glu Val
            1055                1060                1065
Tyr Phe Glu Leu Asn Gly Glu Leu Arg Lys Ile Arg Val Ala Asp
            1070                1075                1080
Lys Ser Gln Asn Ile Gln Ser Val Ala Lys Pro Lys Ala Asp Val
            1085                1090                1095
His Asp Thr His Gln Ile Gly Ala Pro Met Ala Gly Val Ile Ile
            1100                1105                1110
Glu Val Lys Val His Lys Gly Ser Leu Val Lys Lys Gly Glu Ser
            1115                1120                1125
Ile Ala Val Leu Ser Ala Met Lys Met Glu Met Val Val Ser Ser
            1130                1135                1140
```

```
Pro Ala Asp Gly Gln Val Lys Asp Val Phe Ile Lys Asp Gly Glu
    1145                1150                1155

Ser Val Asp Ala Ser Asp Leu Leu Val Val Leu Glu Glu Glu Thr
    1160                1165                1170

Leu Pro Pro Ser Gln Lys Lys
    1175            1180

<210> SEQ ID NO 42
<211> LENGTH: 3543
<212> TYPE: DNA
<213> ORGANISM: Saccharomyces cerevisiae

<400> SEQUENCE: 42
```

| | | | | | |
|---|---|---|---|---|---|
| atgagcagta | gcaagaaatt | ggccggtctt | agggacaatt | tcagtttgct | cggcgaaaag | 60 |
| aataagatct | tggtcgccaa | tagaggtgaa | attccgatta | gaattttttag | atctgctcat | 120 |
| gagctgtcta | tgagaaccat | cgccatatac | tcccatgagg | accgtctttc | aatgcacagg | 180 |
| ttgaaggcgg | acgaagcgta | tgttatcggg | gaggagggcc | agtatacacc | tgtgggtgct | 240 |
| tacttggcaa | tggacgagat | catcgaaatt | gcaagaagc | ataaggtgga | tttcatccat | 300 |
| ccaggttatg | ggttcttgtc | tgaaaattcg | gaatttgccg | acaaagtagt | gaaggccggt | 360 |
| atcacttgga | tcggccctcc | agctgaagtt | attgactctg | tgggtgacaa | agtctctgcc | 420 |
| agacacttgg | cagcaagagc | taacgttcct | accgttcccg | gtactccagg | acctatcgaa | 480 |
| actgtgcaag | aggcacttga | cttcgttaat | gaatacggct | acccggtgat | cattaaggcc | 540 |
| gcctttggtg | gtggtggtag | aggtatgaga | gtcgttagag | aaggtgacga | cgtggcagat | 600 |
| gcctttcaac | gtgctacctc | cgaagcccgt | actgccttcg | gtaatggtac | ctgctttgtg | 660 |
| gaaagattct | tggacaagcc | aaagcatatt | gaagttcaat | tgttggctga | taaccacgga | 720 |
| aacgtggttc | atcttttcga | aagagactgt | tctgtgcaaa | gaagacacca | aaaagttgtc | 780 |
| gaagtcgctc | cagcaaagac | tttgccccgt | gaagttcgtg | acgctatttt | gacagatgct | 840 |
| gttaaattag | ctaaggtatg | tggttacaga | aacgcaggta | ccgccgaatt | cttggttgac | 900 |
| aaccaaaaca | gacactattt | cattgaaatt | aatccaagaa | ttcaagtgga | gcataccatc | 960 |
| actgaagaaa | tcaccggtat | tgacattgtt | tctgcccaaa | tccagattgc | cgcaggtgcc | 1020 |
| actttgactc | aactaggtct | attacaggat | aaaatcacca | cccgtgggtt | ttccatccaa | 1080 |
| tgtcgtatta | ccactgaaga | tcctctaag | aatttccaac | cggataccgg | tcgcctggag | 1140 |
| gtctatcgtt | ctgccggtgg | taatggtgtg | agattggacg | tggtaacgc | ttatgcaggt | 1200 |
| gctactatct | cgcctcacta | cgactcaatg | ctggtcaaat | gttcatgctc | tggttctact | 1260 |
| tatgaaatcg | tccgtaggaa | gatgattcgt | gccctgatcg | aattcagaat | cagaggtgtt | 1320 |
| aagaccaaca | ttcccttcct | attgactctt | ttgaccaatc | cagtttttat | tgagggtaca | 1380 |
| tactggacga | cttttattga | cgacaccccca | caactgttcc | aaatggtatc | gtcacaaaac | 1440 |
| agagcgcaaa | aactgttaca | ctatttggca | gacttggcag | ttaacggttc | ttctattaag | 1500 |
| ggtcaaattg | gcttgccaaa | actaaaatca | aatccaagtg | tcccccattt | gcacgatgct | 1560 |
| cagggcaatg | tcatcaacgt | tacaaagtct | gcaccaccat | ccggatggag | acaagtgcta | 1620 |
| ctggaaaagg | gaccatctga | atttgccaag | caagtcagac | agttcaatgg | tactctactg | 1680 |
| atggacacca | cctggagaga | cgctcatcaa | tctctacttg | caacaagagt | cagaacccac | 1740 |
| gatttggcta | caatcgctcc | aacaaccgca | catgcccttg | caggtgcttt | cgctttagaa | 1800 |
| tgttggggtg | gtgctacatt | cgacgttgca | atgagattct | tgcatgagga | tccatgggaa | 1860 |

| | |
|---|---|
| cgtctgagaa aattaagatc tctggtgcct aatattccat tccaaatgtt attacgtggt | 1920 |
| gccaacggtg tggcttactc ttcattacct gacaatgcta ttgaccattt tgtcaagcaa | 1980 |
| gccaaggata atggtgttga tatatttaga gttttgatg ccttgaatga tttagaacaa | 2040 |
| ttaaaagttg gtgtgaatgc tgtcaagaag gccggtggtg ttgtcgaagc tactgtttgt | 2100 |
| tactctggtg acatgcttca gccaggtaag aaatacaact tagactacta cctagaagtt | 2160 |
| gttgaaaaaa tagttcaaat gggtacacat atcttgggta ttaaggatat ggcaggtact | 2220 |
| atgaaaccgg ccgctgccaa attattaatt ggctccctaa gaaccagata tccggattta | 2280 |
| ccaattcatg ttcacagtca tgactccgca ggtactgctg ttgcgtctat gactgcatgt | 2340 |
| gccctagcag gtgctgatgt tgtcgatgta gctatcaatt caatgtcggg cttaacttcc | 2400 |
| caaccatcaa ttaatgcact gttggcttca ttagaaggta acattgatac tgggattaac | 2460 |
| gttgagcatg ttcgtgaatt agatgcatac tgggccgaaa tgagactgtt gtattcttgt | 2520 |
| ttcgaggccg acttgaaggg accagatcca gaagtttacc aacatgaaat cccaggtggt | 2580 |
| caattgacta acttgttatt ccaagctcaa caactgggtc ttggtgaaca atgggctgaa | 2640 |
| actaaaagag cttacagaga agccaattac ctactgggag atattgttaa agttaccccca | 2700 |
| acttctaagg ttgtcggtga tttagctcaa ttcatggttt ctaacaaaact gacttccgac | 2760 |
| gatattagac gtttagctaa ttctttggac tttcctgact ctgttatgga cttttttgaa | 2820 |
| ggtttaattg gtcaaccata cggtgggttc ccagaaccat taagatctga tgtattgaga | 2880 |
| aacaagagaa gaaagttgac gtgccgtcca ggtttagaat tagaaccatt tgatctcgaa | 2940 |
| aaaattagag aagacttgca gaacagattc ggtgatattg atgaatgcga tgttgcttct | 3000 |
| tacaatatgt atccaagggt ctatgaagat ttccaaaaga tcagagaaac atacggtgat | 3060 |
| ttatcagttc taccaaccaa aaatttccta gcaccagcag aacctgatga agaaatcgaa | 3120 |
| gtcaccatcg aacaaggtaa gactttgatt atcaaattgc aagctgttgg tgacttaaat | 3180 |
| aagaaaactg ggcaaagaga agtgtatttt gaattgaacg gtgaattaag aaagatcaga | 3240 |
| gttgcagaca gtcacaaaaa catacaatct gttgctaaac caaaggctga tgtccacgat | 3300 |
| actcaccaaa tcggtgcacc aatggctggt gttatcatag aagttaaagt acataaaggg | 3360 |
| tctttggtga aaaagggcga atcgattgct gttttgagtg ccatgaaaat ggaaatggtt | 3420 |
| gtctcttcac cagcagatgg tcaagttaaa gacgtttca ttaaggatgg tgaaagtgtt | 3480 |
| gacgcatcag atttgttggt tgtcctagaa gaagaaaccc tacccccatc ccaaaaaaag | 3540 |
| taa | 3543 |

<210> SEQ ID NO 43
<211> LENGTH: 30
<212> TYPE: DNA
<213> ORGANISM: Artificial sequence
<220> FEATURE:
<223> OTHER INFORMATION: P1 primer

<400> SEQUENCE: 43
ggactagtat gagcagtagc aagaaattgg                                    30

<210> SEQ ID NO 44
<211> LENGTH: 31
<212> TYPE: DNA
<213> ORGANISM: Artificial sequence
<220> FEATURE:
<223> OTHER INFORMATION: P2 primer

```
<400> SEQUENCE: 44
ccgctcgagt tactttttt gggatggggg t                                      31
```

SUCCINIC ACID PRODUCTION IN A EUKARYOTIC CELL

CROSS REFERENCE TO RELATED APPLICATIONS

This application is a Continuation of U.S. application Ser. No. 12/743,106, filed May 14, 2010, which is a §371 National Stage Application of International Application No. PCT/EP2008/065583, filed Nov. 14, 2008, which claims priority to European Application No. 07121117.1, filed Nov. 20, 2007, European Application No. 07121120.5, filed Nov. 20, 2007, European Application No. 07121113.0, filed Nov. 20, 2007, European Application No. 08156961.8, filed May 27, 2008, European Application No. 08156960.0, filed May 27, 2008, and European Application No. 08156959.2, filed May 27, 2008, the content of all of which are hereby incorporated herein by reference in their entireties.

BACKGROUND

Field of the Invention

The present invention relates to a recombinant eukaryotic cell comprising a nucleotide sequence encoding a fumarate reductase and a process for the production of succinic acid wherein the recombinant eukaryotic cell is used.

Description of Related Art

Succinic acid is a potential precursor for numerous chemicals. For example, succinic acid can be converted into 1,4-butanediol (BDO), tetrahydrofuran, and gamma-butyrolactone. Another product derived from succinic acid is a polyester polymer which is made by linking succinic acid and BDO.

Succinic acid is predominantly produced through petrochemical processes by hydrogenation of butane. These processes are considered harmful for the environment and costly. The fermentative production of succinic acid may be an attractive alternative process for the production of succinic acid, wherein renewable feedstock as a carbon source may be used.

A number of different bacteria such as *Escherichia coli*, and the rumen bacteria *Actinobacillus, Anaerobiospirillum, Bacteroides, Mannheimia,* or *Succinimonas,* sp. are known to produce succinic acid. Metabolic engineering of these bacterial strains have improved the succinic acid yield and/or productivity, or reduced the by-product formation. WO2007/061590 discloses a pyruvate decarboxylase negative yeast for the production of malic acid and/or succinic acid which is transformed with a pyruvate carboxylase enzyme or a phosphoenolpyruvate carboxylase, a malate dehydrogenase enzyme, and a malic acid transporter protein (MAE). Despite the improvements that have been made in the fermentative production of succinic acid, there remains a need for improved microorganisms for the fermentative production of succinic acid.

SUMMARY

The aim of the present invention is an alternative microorganism for the production of succinic acid.

The aim is achieved according to the invention with a recombinant eukaryotic cell selected from the group consisting of a yeast and a filamentous fungus comprising a nucleotide sequence encoding NAD(H)-dependent fumarate reductase that catalyses the conversion of fumaric acid to succinic acid.

Surprisingly it was found that the recombinant eukaryotic cell according to the present invention produces an increased amount of succinic acid compared to the amount of succinic acid produced by a wild-type eukaryotic cell. Preferably, a eukaryotic cell according to the present invention produces at least 1.2, preferably at least 1.5, preferably at least 2 times more succinic acid than a wild-type eukaryotic cell which does not comprise the nucleotide sequence encoding NAD (H)-dependent fumarate reductase.

DETAILED DESCRIPTION OF THE DRAWINGS

FIGS. 1-23 represent embodiments as described herein.

DETAILED DESCRIPTION OF A PREFERRED EMBODIMENT

As used herein, a recombinant eukaryotic cell according to the present invention is defined as a cell which contains, or is transformed or genetically modified with a nucleotide sequence or polypeptide that does not naturally occur in the eukaryotic cell, or it contains additional copy or copies of an endogenous nucleic acid sequence. A wild-type eukaryotic cell is herein defined as the parental cell of the recombinant cell.

The nucleotide sequence encoding a NAD(H)-dependent fumarate reductase that catalyses the conversion of fumaric acid to succinic acid may be a heterologous or homologous nucleotide sequence, or encodes a heterologous or homologous NAD(H)-dependent fumarate reductase, which may have been further genetically modified by mutation, disruption or deletion. Recombinant DNA techniques are well known in the art such as in Sambrook and Russel (2001) "Molecular Cloning: A Laboratory Manual ($3^{rd}$ edition), Cold Spring Harbor Laboratory Press.

The term "homologous" when used to indicate the relation between a given (recombinant) nucleic acid or polypeptide molecule and a given host organism or host cell, is understood to mean that in nature the nucleic acid or polypeptide molecule is produced by a host cell or organisms of the same species, preferably of the same variety or strain.

The term "heterologous" when used with respect to a nucleic acid (DNA or RNA) or protein refers to a nucleic acid or protein that does not occur naturally as part of the organism, cell, genome or DNA or RNA sequence in which it is present, or that is found in a cell or location or locations in the genome or DNA or RNA sequence that differ from that in which it is found in nature. Heterologous nucleic acids or proteins are not endogenous to the cell into which it is introduced, but have been obtained from another cell or synthetically or recombinantly produced.

A NAD(H)-dependent fumarate reductase according to the present invention uses NAD(H) as a cofactor, whereas most eukaryotic cells comprise a $FADH_2$-dependent fumarate reductase, wherein $FADH_2$ is the cofactor. It was found advantageous that the eukaryotic cell comprises a nucleotide sequence encoding a NAD(H)-dependent fumarate reductase, since the NAD(H)-dependent fumarate reductase provides the cell with further options to oxidise NAD(H) to NAD and influence the redox balance in the cell.

Preferably, the cell expresses a nucleotide sequence encoding an enzyme that catalyses the formation of succinic acid, wherein the nucleotide sequence preferably encodes a NAD(H)-dependent fumarate reductase, comprising an amino acid sequence that has at least 40%, preferably at least 45, 50, 55, 60, 65, 70, 75, 80, 85, 90, 95, 97, 98, 99% sequence identity with the amino acid sequence of SEQ ID NO: 1, and/or SEQ ID NO: 3, and/or SEQ ID NO: 4, and/or SEQ ID NO: 6. Preferably, the nucleotide sequence encodes a NAD(H)-dependent fumarate reductase comprising the amino acid sequence of SEQ ID NO: 1, and/or SEQ ID NO: 3, and/or SEQ ID NO: 4, and/or SEQ ID NO: 6.

Sequence identity is herein defined as a relationship between two or more amino acid (polypeptide or protein) sequences or two or more nucleic acid (polynucleotide) sequences, as determined by comparing the sequences. Usually, sequence identities or similarities are compared over the whole length of the sequences compared. In the art, "identity" also means the degree of sequence relatedness between amino acid or nucleic acid sequences, as the case may be, as determined by the match between strings of such sequences.

Preferred methods to determine identity are designed to give the largest match between the sequences tested. Methods to determine identity and similarity are codified in publicly available computer programs. Preferred computer program methods to determine identity and similarity between two sequences include BLASTP and BLASTN, publicly available from NCBI and other sources (BLAST Manual, Altschul, S., et al., NCBI NLM NIH Bethesda, Md. 20894). Preferred parameters for amino acid sequences comparison using BLASTP are gap open 11.0, gap extend 1, Blosum 62 matrix. Nucleotide sequences encoding the enzymes expressed in the cell of the invention may also be defined by their capability to hybridise with the nucleotide sequences encoding a NAD(H) dependent fumarate reductase of SEQ ID NO: 1, SEQ ID NO: 3, SEQ ID NO: 4, and/or SEQ ID NO: 6, under moderate, or preferably under stringent hybridisation conditions. Stringent hybridisation conditions are herein defined as conditions that allow a nucleic acid sequence of at least about 25, preferably about 50 nucleotides, 75 or 100 and most preferably of about 200 or more nucleotides, to hybridise at a temperature of about 65° C. in a solution comprising about 1 M salt, preferably 6×SSC (sodium chloride, sodium citrate) or any other solution having a comparable ionic strength, and washing at 65° C. in a solution comprising about 0.1 M salt, or less, preferably 0.2×SSC or any other solution having a comparable ionic strength. Preferably, the hybridisation is performed overnight, i.e. at least for 10 hours and preferably washing is performed for at least one hour with at least two changes of the washing solution. These conditions will usually allow the specific hybridisation of sequences having about 90% or more sequence identity.

Moderate conditions are herein defined as conditions that allow a nucleic acid sequences of at least 50 nucleotides, preferably of about 200 or more nucleotides, to hybridise at a temperature of about 45° C. in a solution comprising about 1 M salt, preferably 6×SSC or any other solution having a comparable ionic strength, and washing at room temperature in a solution comprising about 1 M salt, preferably 6×SSC or any other solution having a comparable ionic strength. Preferably, the hybridisation is performed overnight, i.e. at least for 10 hours, and preferably washing is performed for at least one hour with at least two changes of the washing solution. These conditions will usually allow the specific hybridisation of sequences having up to 50% sequence identity. The person skilled in the art will be able to modify these hybridisation conditions in order to specifically identify sequences varying in identity between 50% and 90%.

To increase the likelihood that an introduced enzyme(s) is/are expressed in active form in a eukaryotic cell of the invention, the corresponding encoding nucleotide sequence may be adapted to optimise its codon usage to that of the chosen eukaryote host cell. Several methods for codon optimisation are known in the art. A preferred method to optimise codon usage of the nucleotide sequences to that of the eukaryotic cell is a codon pair optimization technology as disclosed in WO2008/000632. Codon-pair optimization is a method for producing a polypeptide in a host cell, wherein the nucleotide sequences encoding the polypeptide have been modified with respect to their codon-usage, in particular the codon-pairs that are used, to obtain improved expression of the nucleotide sequence encoding the polypeptide and/or improved production of the polypeptide. Codon pairs are defined as a set of two subsequent triplets (codons) in a coding sequence.

The term "gene", as used herein, refers to a nucleic acid sequence containing a template for a nucleic acid polymerase, in eukaryotes, RNA polymerase II. Genes are transcribed into mRNAs that are then translated into protein.

The term "nucleic acid" as used herein, includes reference to a deoxyribonucleotide or ribonucleotide polymer, i.e. a polynucleotide, in either single- or double-stranded form, and unless otherwise limited, encompasses known analogues having the essential nature of natural nucleotides in that they hybridize to single-stranded nucleic acids in a manner similar to naturally occurring nucleotides (e.g., peptide nucleic acids). A polynucleotide can be full-length or a subsequence of a native or heterologous structural or regulatory gene. Unless otherwise indicated, the term includes reference to the specified sequence as well as the complementary sequence thereof.

The terms "polypeptide", "peptide" and "protein" are used interchangeably herein to refer to a polymer of amino acid residues. The terms apply to amino acid polymers in which one or more amino acid residue is an artificial chemical analogue of a corresponding naturally occurring amino acid, as well as to naturally occurring amino acid polymers. The essential nature of such analogues of naturally occurring amino acids is that, when incorporated into a protein, that protein is specifically reactive to antibodies elicited to the same protein but consisting entirely of naturally occurring amino acids. The terms "polypeptide", "peptide" and "protein" are also inclusive of modifications including, but not limited to, glycosylation, lipid attachment, sulfation, gamma-carboxylation of glutamic acid residues, hydroxylation and ADP-ribosylation.

The term "enzyme" as used herein is defined as a protein which catalyses a (bio)chemical reaction in a cell.

Usually, the nucleotide sequence encoding an enzyme is operably linked to a promoter that causes sufficient expression of the corresponding nucleotide sequence in the eukaryotic cell according to the present invention to confer to the cell the ability to produce succinic acid.

As used herein, the term "operably linked" refers to a linkage of polynucleotide elements (or coding sequences or nucleic acid sequence) in a functional relationship. A nucleic acid sequence is "operably linked" when it is placed into a functional relationship with another nucleic acid sequence. For instance, a promoter or enhancer is operably linked to a coding sequence if it affects the transcription of the coding sequence.

As used herein, the term "promoter" refers to a nucleic acid fragment that functions to control the transcription of one or more genes, located upstream with respect to the direction of transcription of the transcription initiation site of the gene, and is structurally identified by the presence of a binding site for DNA-dependent RNA polymerase, transcription initiation sites and any other DNA sequences known to one of skilled in the art. A "constitutive" promoter is a promoter that is active under most environmental and developmental conditions. An "inducible" promoter is a promoter that is active under environmental or developmental regulation.

A promoter that could be used to achieve the expression of a nucleotide sequence coding for an enzyme such as NAD(H)-dependent fumarate reductase or any other enzyme introduced in the eukaryotic cell of the invention, may be not native to a nucleotide sequence coding for the enzyme to be expressed, i.e. a promoter that is heterologous to the nucleotide sequence (coding sequence) to which it is operably linked. Preferably, the promoter is homologous, i.e. endogenous to the host cell.

Suitable promoters in this context include both constitutive and inducible natural promoters as well as engineered promoters, which are well known to the person skilled in the art. Suitable promoters in eukaryotic host cells may be GAL7, GAL10, or GAL 1, CYC1, HIS3, ADH1, PGL, PH05, GAPDH, ADC1, TRP1, URA3, LEU2, ENO, TPI, and AOX1. Other suitable promoters include PDC, GPD1, PGK1, TEF1, and TDH.

Usually a nucleotide sequence encoding an enzyme comprises a terminator. Any terminator, which is functional in the eukaryotic cell, may be used in the present invention. Preferred terminators are obtained from natural genes of the host cell. Suitable terminator sequences are well known in the art. Preferably, such terminators are combined with mutations that prevent nonsense mediated mRNA decay in the host cell of the invention (see for example: Shirley et al., 2002, Genetics 161:1465-1482).

In a preferred embodiment, a nucleotide sequence encoding a NAD(H)-dependent fumarate reductase may be overexpressed to achieve a sufficient production of succinic acid by the cell.

There are various means available in the art for overexpression of nucleotide sequences encoding enzymes in a eukaryotic cell of the invention. In particular, a nucleotide sequence encoding an enzyme may be overexpressed by increasing the copy number of the gene coding for the enzyme in the cell, e.g. by integrating additional copies of the gene in the cell's genome, by expressing the gene from a centromeric vector, from an episomal multicopy expression vector or by introducing an (episomal) expression vector that comprises multiple copies of the gene. Preferably, overexpression of the enzyme according to the invention is achieved with a (strong) constitutive promoter.

The invention also relates to a nucleotide construct comprising one or more nucleotide sequence(s) selected from the group consisting of SEQ ID NO: 7, SEQ ID NO: 8, SEQ ID NO: 9 or SEQ ID NO: 10.

The nucleic acid construct may be a plasmid, for instance a low copy plasmid or a high copy plasmid. The eukaryotic cell according to the present invention may comprise a single, but preferably comprises multiple copies of the nucleotide sequence encoding a NAD(H) dependent fumarate reductase, for instance by multiple copies of a nucleotide construct.

The nucleic acid construct may be maintained episomally and thus comprise a sequence for autonomous replication, such as an autosomal replication sequence. If the eukaryotic cell is of fungal origin, a suitable episomal nucleic acid construct may e.g. be based on the yeast 2μ or pKD1 plasmids (Gleer et al., 1991, Biotechnology 9: 968-975), or the AMA plasmids (Fierro et al., 1995, Curr Genet. 29:482-489). Alternatively, each nucleic acid construct may be integrated in one or more copies into the genome of the eukaryotic cell. Integration into the cell's genome may occur at random by non-homologous recombination but preferably, the nucleic acid construct may be integrated into the cell's genome by homologous recombination as is well known in the art.

The nucleotide sequence encoding a NAD(H)-dependent fumarate reductase, may be a heterologous or a homologous nucleotide sequence. Preferably, the NADH-dependent fumarate reductase is a heterologous enzyme, which may be derived from any suitable origin, for instance bacteria, fungi, protozoa or plants. Preferably, the cell according to the invention comprises hetereologous a NAD(H)-dependent fumarate reductase, preferably derived from a *Trypanosoma* sp, for instance a *Trypanosomal brucei*.

In a preferred embodiment the nucleotide sequence encoding a NAD(H)-dependent fumarate reductase is expressed in the cytosol. Surprisingly, cytosolic activity of the enzyme resulted in an increased productivity of succinic acid by the eukaryotic cell.

In the event that the nucleotide sequence encoding a NAD(H)-dependent fumarate reductase comprises a peroxisomal or mitochondrial targeting signal, it may be essential to modify or delete a number of amino acids (and corresponding nucleotide sequences in the encoding nucleotide sequence) in order to prevent peroxisomal or mitochondrial targeting of the enzyme. The presence of a peroxisomal targeting signal may for instance be determined by the method disclosed by Schlüter et al, Nucleic acid Research 2007, 35, D815-D822.

Preferably, the NAD(H)-dependent fumarate reductase lacks a peroxisomal or mitochondrial targeting signal for cytosolic activity of the enzyme upon expression of the encoding nucleotide sequence.

Preferably, the cell expresses a nucleotide sequence encoding an enzyme that catalyses the formation of succinic acid, wherein the nucleotide sequence preferably encodes a NAD(H)-dependent fumarate reductase, preferably a fumarate reductase comprising an amino acid sequence that has at least 40%, preferably at least 45, 50, 55, 60, 65 70, 75, 80, 85, 90, 95, 97, 98, 99% sequence identity with the amino acid sequence of SEQ ID NO: 3, and/or SEQ ID NO: 6. Preferably the nucleotide sequence encodes a NAD(H)-dependent fumarate reductase comprising the amino acid sequence of SEQ ID NO: 3, and/or SEQ ID NO: 6.

The eukaryotic cell selected from the group consisting of a yeast and a filamentous fungus, preferably belongs to one of the genera *Saccharomyces, Aspergillus, Penicillium, Pichia, Kluyveromyces, Yarrowia, Candida, Hansenula, Humicola, Rhizopus, Torulaspora, Trichosporon, Brettanomyces, Zygosaccharomyces, Pachysolen* or *Yamadazyma*. More preferably, the eukaryotic cell is a *Saccharomyces cervisiae, Saccharomyces uvarum, Saccharomyces bayanus, Aspergillus niger, Penicillium chrysogenum, Pichia stipidis, Kluyveromyces marxianus, K. lactis, K. thermotolerans, Yarrowia lipolytica, Candida sonorensis, C. glabrata, Hansenula polymorpha, Torulaspora delbrueckii, Brettanomyces bruxellensis, Rhizopus orizae* or *Zygosaccharomyces bailii*.

In addition to a nucleotide sequence encoding a NAD(H)-dependent fumarate reductase that catalyses the conversion of fumaric acid to succinic acid, recombinant eukaryotic cell according to the present invention may comprise further genetic modifications, for instance mutations, deletions or disruptions, in homologous nucleotide sequences and/or transformation with nucleotide sequences that encode homologous or heterologous enzymes that catalyse a reaction in the cell resulting in an increased flux towards succinic acid. It may for example be favourable to introduce, genetically modify and/or overexpress heterologous and/or homologous nucleotide sequences encoding i) an enzyme that catalyses the conversion of phosphoenolpyruvate or pyruvate to oxaloacetate; ii) a malate dehydrogenase which catalyses the conversion from OAA to malic acid; or iii) a fumarase, which catalyses the conversion of malic acid to fumaric acid.

A eukaryotic cell may be transformed or genetically modified with any suitable nucleotide sequence catalyzing the reaction from a C3 to C4 carbon molecule, such as phosphoenolpyruvate (PEP, C3) to oxaloacetate (OAA, C4) and pyruvate (C3) to OAA or malic acid (C3). Suitable enzymes are PEP carboxykinase (EC 4.1.1.49, EC 4.1.1.38) and PEP carboxylase (EC 4.1.1.31) which catalyse the conversion of PEP to OAA; pyruvate carboxylase (EC 6.4.1.1.), that catalyses the reaction from pyruvate to OAA; or malic enzyme (EC 1.1.1.38), that catalyses the reaction from pyruvate to malic acid.

Preferably a eukaryotic cell according to the present invention overexpresses a nucleotide sequence encoding a pyruvate carboxylase (PYC), preferably a pyruvate carboxylase that is active in the cytosol upon expression of the nucleotide sequence encoding a PYC, for instance a PYC comprising an amino acid sequence according to SEQ ID NO: 41. Preferably, an endogenous or homologous pyruvate carboxylase is overexpressed. Surprisingly, it was found that overexpressing an endogenous pyruvate carboxylase resulted in increased succinic acid production levels by the eukaryotic cell according to the present invention.

In another preferred embodiment, a eukaryotic cell according to the present invention further comprises a nucleotide sequence encoding a heterologous PEP carboxykinase (EC 4.1.1.49) catalysing the reaction from phosphoenolpyruvate to oxaloacetate. Surprisingly it was found that a eukaryotic cell according to the present invention which further comprises a heterologous PEP carboxykinase produced an increased amount of succinic acid as compared to a eukaryotic cell that does not comprise the heterologous PEP carboxykinase. Preferably, a PEP carboxykinase that is derived from bacteria, more preferably the enzyme having PEP carboxykinase activity is derived from *Escherichia coli, Mannheimia* sp., *Actinobacillus* sp., or *Anaerobiospirillum* sp., more preferably *Mannheimia succiniciproducens, Actinobacillus succinogenes*, or *Anaerobiospirillum succiniciproducens*. Preferably, the PEP carboxykinase is active in the cytosol upon expression of the nucleotide sequence encoding PEP carboxykinase since it was found that this resulted in an increase succinic acid production. In one embodiment the PEP carboxykinase of *Actinobacillus succinogenes* (PCKa) has been modified to replace EGY at position 120-122 with a DAF amino acid sequence. Preferably, a eukaryotic cell according to the present invention comprises a PEP carboxykinase which has at least 80, 85, 90, 95 or 99% sequence identity with SEQ ID NO: 14 or SEQ ID NO: 17, preferably a PEP carboxykinase comprising SEQ ID NO: 14 or SEQ ID NO: 17. Surprisingly it was found that the concomitant (over)expression of a PYC and a PEP carboxykinase as described herein resulted in at least 1.5 increase in succinic acid production.

In another preferred embodiment a cell according to the present invention further comprises a nucleotide sequence encoding a malate dehydrogenase (MDH) which is active in the cytosol upon expression of the nucleotide sequence. A cytosolic MDH may be any suitable homologous or heterologous malate dehydrogenase. The MDH may be a *S. cerevisiae* MDH3 or *S. cerevisiae* MDH1. Preferably, the MDH lacks a peroxisomal or mitochondrial targeting signal in order to localize the enzyme in the cytosol. Alternatively, the MDH is *S. cerevisiae* MDH2 which has been modified such that it is not inactivated in the presence of glucose and is active in the cytosol. It is known that the transcription of MDH2 is repressed and Mdh2p is degraded upon addition of glucose to glucose-starved cells. Mdh2p deleted for the first 12 amino-terminal amino acids is less-susceptible for glucose-induced degradation (Minard and McAlister-Henn, J. Biol Chem. 1992 Aug. 25; 267(24):17458-64). Preferably, a eukaryotic cell according to the present invention comprises a nucleotide sequence encoding a malate dehydrogenase that has at least 70%, preferably at least 75, 80, 85, 90, 92, 94, 95, 96, 97, 98, 99% sequence identity with the amino acid sequence of SEQ ID NO: 19 or SEQ ID NO: 21. Preferably the malate dehydrogenase comprises SEQ ID NO: 19 or SEQ ID NO: 21. Preferably, the activity of malate dehydrogenase is increased by overexpressing the encoding nucleotide sequence by known methods in the art.

Preferably, a eukaryotic cell according to the present invention further comprises a nucleotide sequence encoding an enzyme that catalyses the conversion of malic acid to fumaric acid, which may be a heterologous or homologous enzyme, for instance a fumarase (FUM). A nucleotide sequence encoding an heterologous enzyme that catalyses the conversion of malic acid to fumaric acid, may be derived from any suitable origin, preferably from microbial origin, preferably from a yeast, for instance *Saccharomyces cerevisiae* or a filamentous fungus, for instance *Rhizopus oryzae*. Preferably, a eukaryotic cell according to the present invention comprises a nucleotide sequence encoding a fumarase that has at least 70%, preferably at least 75, 80, 85, 90, 92, 94, 95, 96, 97, 98, or 99% sequence identity with the amino acid sequence of SEQ ID NO: 23. Preferably, the fumarase comprises SEQ ID NO: 23. Preferably the enzyme having fumarase activity is active in the cytosol upon expression of the nucleotide sequence encoding the enzyme having fumarase activity. Surprisingly, it was found that a eukaryotic cell further comprising an enzyme having fumarase activity as described herein produced an increased amount of succinic acid.

In another embodiment, a eukaryotic cell according to the present invention comprises a nucleotide sequence encoding a dicarboxylic acid transporter protein, preferably a malic acid transporter protein (MAE). A dicarboxylic acid transporter protein may be a homologous or heterologous protein. Preferably the dicarboxylic acid transporter protein is a heterologous protein. A dicarboxylic acid transporter protein may be derived from any suitable organism, preferably from *Schizosaccharomyces pombe*. Preferably, a dicarboxylic acid transporter protein is a malic acid transporter protein (MAE) which has at least 80, 85, 90, 95 or 99% sequence identity with SEQ ID NO: 36. Preferably the MAE comprises SEQ ID NO: 36. Surprisingly, it was found that a eukaryotic cell according to the present invention further comprising a dicarboxylic acid transporter, such as a malic acid transporter as described herein produced an increased amount of succinic acid as compared to a eukaryote cell not comprising a dicarboxylic acid transporter protein.

The present invention also relates to the use of a dicarboxylic acid transporter, preferably a malic acid transporter protein, in a eukaryotic cell to increase succinic acid production. Preferably, the malic acid transporter is derived from *Schizosaccharomyces pombe*.

In a preferred embodiment a eukaryotic cell according to the present invention is a yeast comprising nucleotide sequences encoding a NAD(H)-dependent fumarate reductase, a malate dehydrogenase, a heterologous fumarase, a heterologous PEP carboxykinase and a heterologous dicarboxylic acid transporter and overexpresses a pyruvate carboxylase (PYC), as described, including the preferred embodiments, herein above. Surprisingly, it found that a yeast of the invention comprising the nucleotide sequences encoding the enzymes as described herein produced an increased amount of succinic acid as compared to a yeast comprising either of the nucleotide sequences alone.

In another preferred embodiment a eukaryotic cell according to the present invention comprises reduced activity of enzymes that convert NAD(H) to NAD+ compared to the activity of these enzymes in a wild-type cell.

Preferably, the cell according to the present invention is a cell wherein at least one gene encoding alcohol dehydrogenase is not functional. An alcohol dehydrogenase gene that is not functional is used herein to describe a eukaryotic cell which comprises a reduced alcohol dehydrogenase activity compared to a cell wherein all genes encoding an alcohol dehydrogenase are functional. A gene may become not functional by known methods in the art, for instance by mutation, disruption, or deletion, for instance by the method disclosed by Gueldener et. al. 2002, Nucleic Acids Research, Vol. 30, No. 6, e23. Preferably, a eukaryotic cell is a yeast cell such as *Saccharomyces cerevisiae*, wherein one or more genes adh1 and/or adh2, encoding alcohol dehydrogenase are inactivated.

Preferably, the cell according to the present invention further comprises at least one gene encoding glycerol-3-phosphate dehydrogenase which is not functional. A glycerol-3-phosphate dehydrogenase gene that is not functional is used herein to describe a eukaryotic cell, which comprises a reduced glycerol-3-phosphate dehydrogenase activity, for instance by mutation, disruption, or deletion of the gene encoding glycerol-3-phosphate dehydrogenase, resulting in a decreased formation of glycerol as compared to the wild-type cell. Surprisingly, it was found that the eukaryotic cell comprising reduced alcohol dehydrogenase activity and/or glycerol-3-phosphate dehydrogenase activity and a NAD(H)-dependent fumarase resulted in an increased production of succinic acid as compared to a cell wherein one or more gene(s) encoding alcohol dehydrogenase and/or glycerol-3-phosphate dehydrogenase are not inactivated.

The present invention also relates to a process for the production of succinic acid comprising fermenting a eukaryotic cell comprising at least one gene encoding alcohol dehydrogenase is not functional and/or at least one gene encoding glycerol-3-phosphate dehydrogenase which is not functional.

In another preferred embodiment the recombinant eukaryotic cell according to the present invention comprises at least one gene encoding succinate dehydrogenase that is not functional. A succinate dehydrogenase that is not functional is used herein to describe a eukaryotic cell, which comprises a reduced succinate dehydrogenase activity by mutation, disruption, or deletion, of at least one gene encoding succinate dehydrogenase resulting in a increased formation of succinic acid as compared to the wild-type cell. A eukaryotic cell comprising a gene encoding succinate dehydrogenase that is not functional may for instance be *Aspergillus niger*, preferably an *Aspergillus niger*, wherein one or more genes encoding succinate dehydrogenase, such as sdhA and sdhB is/are not functional, for instance by deletion of these genes.

Preferably, a eukaryotic cell according to the invention is a yeast, preferably *Saccharomyces cerevisiae*, preferably a *Saccharomyces cerevisiae* comprising one or more of the nucleotide sequences selected from SEQ ID NO: 9 and SEQ ID NO: 10. A eukaryotic cell according to the present invention may also be a filamentous fungus, preferably *A. niger*, preferably *A. niger* comprising one or more nucleotide sequences selected from SEQ ID NO: 7 and SEQ ID NO: 8.

Preferably, a eukaryotic cell according to the present invention comprising any one of the genetic modifications described herein is capable of producing at least 0.3, 0.5, 0.7, g/L succinic acid, preferably at least 1 g/L succinic acid, preferably at least 1.5 preferably at least 2, or 2.5, 4.5 preferably at least 8, 10, 15, or 20 g/L succinic acid but usually below 200 or below 150 g/L.

A preferred eukaryotic cell according to the present invention may be able to grow on any suitable carbon source known in the art and convert it to succinic acid. The eukaryotic cell may be able to convert directly plant biomass, celluloses, hemicelluloses, pectines, rhamnose, galactose, fucose, maltose, maltodextrines, ribose, ribulose, or starch, starch derivatives, sucrose, lactose and glycerol. Hence, a preferred host organism expresses enzymes such as cellulases (endocellulases and exocellulases) and hemicellulases (e.g. endo- and exo-xylanases, arabinases) necessary for the conversion of cellulose into glucose monomers and hemicellulose into xylose and arabinose monomers, pectinases able to convert pectines into glucuronic acid and galacturonic acid or amylases to convert starch into glucose monomers. Preferably, the cell is able to convert a carbon source selected from the group consisting of glucose, fructose, galactose, xylose, arabinose, sucrose, raffinose, lactose and glycerol.

In another aspect, the present invention relates to a process for the preparation of succinic acid, comprising fermenting the eukaryotic cell according to the present invention, wherein succinic acid is prepared.

It was found advantageous to use a eukaryotic cell according to the invention in the process for the production of succinic acid, because most eukaryotic cells do not require sterile conditions for propagation and are insensitive to bacteriophage infections.

Preferably, the succinic acid that is prepared in the process according to the present invention is further converted into a desirable product. A desirable product may for instance be a polymer, such as polybutylene succinic acid (PBS), a deicing agent, or a surfactant.

The process according to the present invention may be run under aerobic and anaerobic conditions. Preferably, the process is carried out under anaerobic conditions or under micro-aerophilic or oxygen limited conditions. An anaerobic fermentation process is herein defined as a fermentation process run in the absence of oxygen or in which substantially no oxygen is consumed, preferably less than 5, 2.5 or 1 mmol/L/h, and wherein organic molecules serve as both electron donor and electron acceptors.

An oxygen-limited fermentation process is a process in which the oxygen consumption is limited by the oxygen transfer from the gas to the liquid. The degree of oxygen limitation is determined by the amount and composition of the ingoing gasflow as well as the actual mixing/mass transfer properties of the fermentation equipment used. Preferably, in a process under oxygen-limited conditions, the rate of oxygen consumption is at least 5.5, more preferably at least 6 and even more preferably at least 7 mmol/L/h.

The process for the production of succinic acid according to the present invention may be carried out at any suitable pH between 1 and 9. Preferably, the pH in the fermentation broth is between 2 and 7, preferably between 3 and 5. It was found advantageous to be able to carry out the process according to the present invention at a low pH, since this prevents bacterial contamination. In addition, since the pH drops during succinic acid production, a lower amount of titrant may be needed to keep the pH at a desired level.

A suitable temperature at which the process according to the present invention may be carried out is between 5 and 60° C., preferably between 10 and 50° C., more preferably between 15 and 35° C., more preferably between 18° C. and 30° C. The skilled man in the art knows which optimal temperatures are suitable for fermenting a specific eukaryotic cell.

Preferably, succinic acid is recovered from the fermentation broth by a suitable method known in the art, for instance by crystallisation and ammonium precipitation.

Preferably, the succinic acid that is prepared in the process according to the present invention is further converted into a pharmaceutical, cosmetic, food, feed, or chemical product. Succinic acid may be further converted into a polymer, such as polybutylene succinate (PBS) or other suitable polymers derived therefrom.

The present invention also relates to a fermentation broth comprising a succinic acid obtainable by a process according to the present invention.

The invention relates to a process for the production of succinic acid by a yeast or a filamentous fungus as succinic acid producer, whereby fumarate reductase from *Trypanosoma brucei* is used to increase succinic acid production, wherein preferably the fumarate reductase is active in the cytosol.

Genetic Modifications

Standard genetic techniques, such as overexpression of enzymes in the host cells, genetic modification of host cells, or hybridisation techniques, are known methods in the art, such as described in Sambrook and Russel (2001) "Molecular Cloning: A Laboratory Manual ($3^{rd}$ edition), Cold Spring Harbor Laboratory, Cold Spring Harbor Laboratory Press, or F. Ausubel et al, eds., "Current protocols in molecular biology", Green Publishing and Wiley Interscience, New York (1987). Methods for transformation, genetic modification etc of fungal host cells are known from e.g. EP-A-0 635 574, WO 98/46772, WO 99/60102 and WO 00/37671, WO90/14423, EP-A-0481008, EP-A-0635 574 and U.S. Pat. No. 6,265,186.

The following examples are for illustrative purposes only and are not to be construed as limiting the invention.

EXAMPLES

Example 1

Cloning of Fumarate Reductases from Trypanosoma Brucei in Aspergillus Niger 1.1. Expression Constructs Mitochondrial fumarate reductase m1 (FRDm1) [E.C. 1.3.1.6], GenBank accession number 60460035, from Trypanosoma brucei was analysed for the presence of signal sequences using SignalP 3.0 (www.cbs.dtu.dk/services/SignalP/) Bendtsen, J. et al. (2004) Mol. Biol., 340:783-795 and TargetP 1.1 (www.cbs.dtu.dk/services/TargetP/) Emanuelsson, O. et al. (2007) Nature Protocols 2, 953-971. A putative mitochondrial targeting sequence in the N-terminal half of the protein was identified, including a possible cleavage site between pos. 25 and 26 (D-S).

Figure 1:
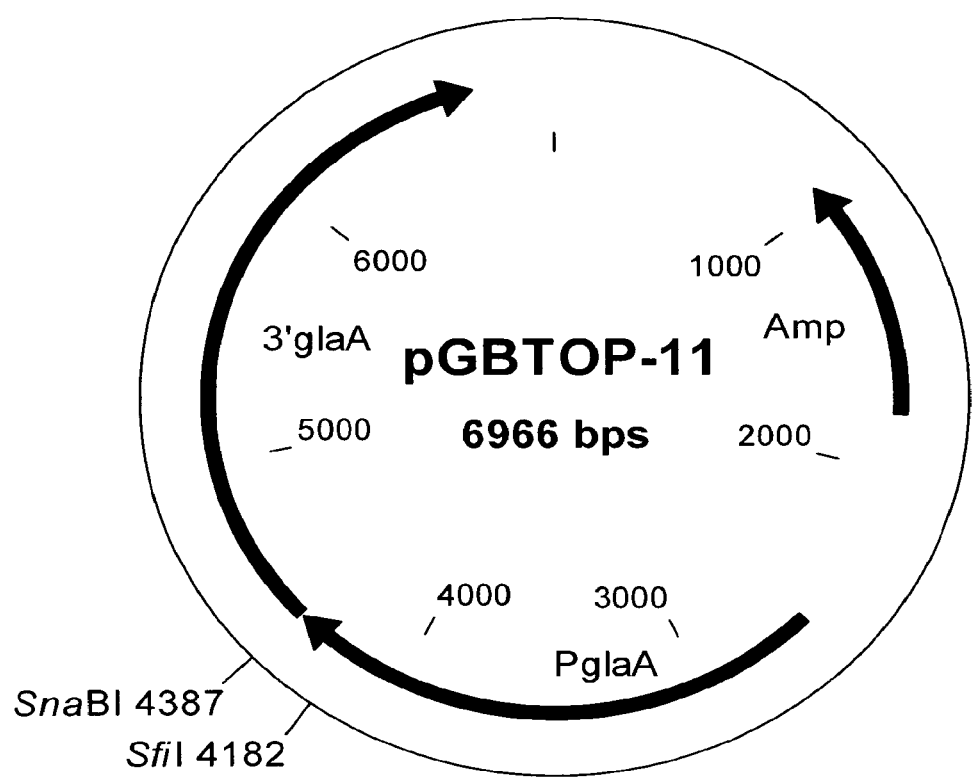
FIG. 1. Map of the pGBTOP-11 vector used for expression of fumarate reductase in *A. niger*
Figure 5:
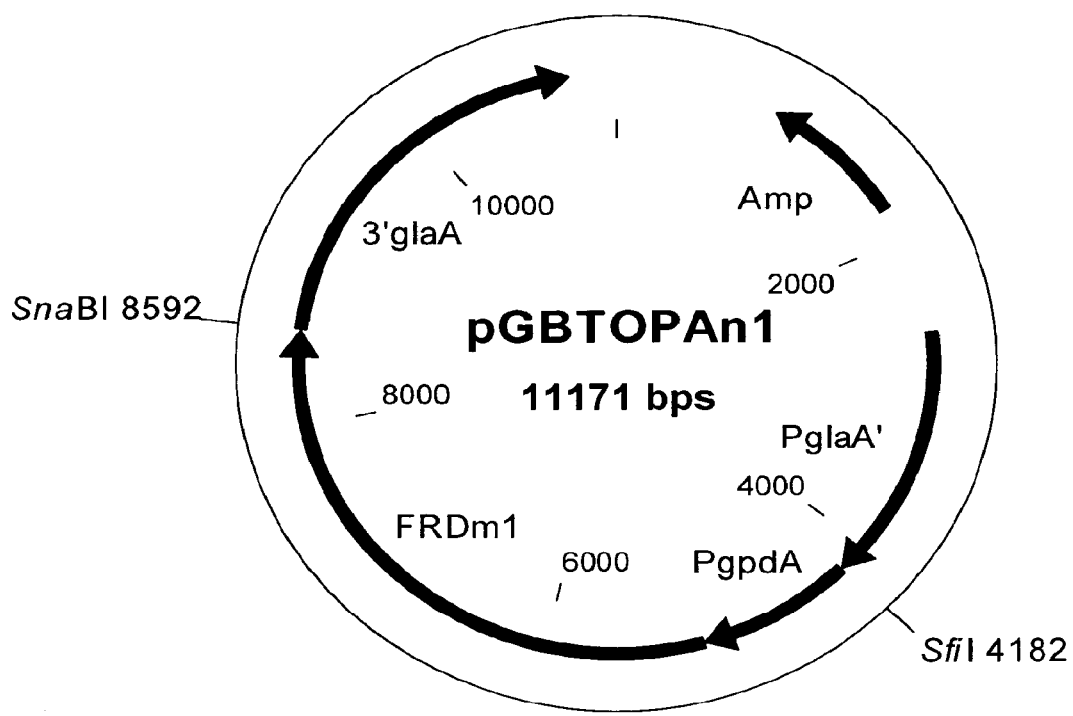
FIG. 5: Map of plasmid pGBTPAn1, for overexpression FRDm1 in *A. niger*.

It was shown that FRDm1 recombinant protein lacking the 68 N-terminal residues, relocalized to the cytosol of the procyclic trypanosomes (Coustou et al., J Biol Chem. 2005 Apr. 29; 280(17):16559-70). These results indicate that the predicted N-terminal signal motif of FRDm1 is required for targeting to the mitochondrion. The first 68 amino acids were removed from SEQ ID NO: 1 (corresponding to nucleotide sequence SEQ ID NO: 2) and a new methionine amino acid was reintroduced, which resulted in SEQ ID NO: 3. SEQ ID NO: 3 was subjected to the codon-pair method as disclosed in WO2008/000632 for A. niger. The resulting sequence SEQ ID NO: 7 was put behind the constitutive GPDA promoter sequence SEQ ID NO: 11, wherein the last 10 nucleotide sequences were replaced with optimal Kozak sequence CACCGTAAA. Convenient restriction sites were added. The stop codon TAA in SEQ: ID NO: 7 was modified to TAAA. The resulting sequence was synthesised at Sloning (Puchheim, Germany). The fragment was SnaBI, SfiI cloned in the A. niger expression vector pGBTOP11 (FIG. 1) using appropriate restriction sites. The resulting plasmid comprising FRDm1 was named pGBTOPAn1 (FIG. 5).

Likewise, glycosomal fumarate reductase (FRDg) [E.C. 1.3.1.6], GenBank accession number 23928422, from Trypanosoma brucei was analysed for peroxisomal targeting in filamentous fungi using the PTS1 predictor mendel.imp.ac.at/mendeljsp/sat/pts1/PTS1predictor.jsp with the fungi-specific prediction function. The C-terminal amino acids at position 1140-1142 (SKI) were removed from the protein SEQ ID NO: 4 (corresponding to nucleotide sequence SEQ ID NO: 5), resulting in SEQ ID NO: 6. SEQ ID NO: 6, was subjected to the codon-pair method as disclosed in PCT/EP2007/05594 for A. niger. The stop codon TAA in SEQ ID NO: 8 was modified to TAAA. The resulting sequence SEQ ID NO: 8 was put behind the constitutive GPDA promoter sequence SEQ ID NO: 11, and convenient restriction sites were added. The resulting sequence was synthesised at Sloning (Puchheim, Germany). The fragment was SnaBI, SfiI cloned in the A. niger expression vector pGBTOP11 (FIG. 1) using appropriate restriction sites.

1.2. Transformation of A. Niger

A. niger WT-1: This A. niger strain is CBS513.88 comprising deletions of the genes encoding glucoamylase (glaA), fungal amylase and acid amylase. A. niger WT 1 was constructed by using the "MARKER-GENE FREE" approach as described in EP 0 635 574 B1.

The expression constructs are co-transformed to strain A. niger WT-1 according to the method described by Tilburn, J. et al. (1983) Gene 26, 205-221 and Kelly, J. & Hynes, M. (1985) EMBO J., 4, 475-479 with the following modifications:

Spores are germinated and cultivated for 16 hours at 30 degrees Celsius in a shake flask placed in a rotary shaker at 300 rpm in Aspergillus minimal medium (100 ml). Aspergillus minimal medium contains per liter: 6 g $NaNO_3$, 0.52 g KCl, 1.52 g $KH_2PO_4$, 1.12 ml 4 M KOH, 0.52 g $MgSO_4.7H_2O$, 10 g glucose, 1 g casaminoacids, 22 mg $ZnSO_4.7H_2O$, 11 mg $H_3BO_3$, 5 mg $FeSO_4.7H_2O$, 1.7 mg $CoCl_2.6H_2O$, 1.6 mg $CuSO_4.5H_2O$, 5 mg $MnCl_2.2H_2O$, 1.5 mg $Na_2MoO_4.2H_2O$, 50 mg EDTA, 2 mg riboflavin, 2 mg thiamine-HCl, 2 mg nicotinamide, 1 mg pyridoxine-HCL, 0.2 mg panthotenic acid, 4 g biotin, 10 ml Penicillin (5000 UI/ml) Streptomycin (5000 UG/ml) solution (Gibco).

Novozym 234™ (Novo Industries) instead of helicase is used for the preparation of protoplasts;

After protoplast formation (60-90 minutes), KC buffer (0.8 M KCl, 9.5 mM citric acid, pH 6.2) is added to a final volume of 45 ml, the protoplast suspension is centrifuged for 10 minutes at 3000 rpm at 4 degrees Celsius in a swinging-bucket rotor. The protoplasts are resuspended in 20 ml KC buffer and subsequently 25 ml of STC buffer (1.2 M sorbitol, 10 mM Tris-HCl pH 7.5, 50 mM $CaCl_2$) is added. The protoplast suspension is centrifuged for 10 minutes at 3000 rpm at 4 degrees Celsius in a swinging-bucket rotor, washed in STC-buffer and resuspended in STC-buffer at a concentration of 10E8 protoplasts/ml;

To 200 microliter of the protoplast suspension, the DNA fragment, dissolved in 10 microliter TE buffer (10 mM Tris-HCl pH 7.5, 0.1 mM EDTA) and 100 microliter of PEG solution (20% PEG 4000 (Merck), 0.8 M sorbitol, 10 mM Tris-HCl pH 7.5, 50 mM $CaCl_2$) is added;

After incubation of the DNA-protoplast suspension for 10 minutes at room temperature, 1.5 ml PEG solution (60% PEG 4000 (Merck), 10 mM Tris-HCl pH 7.5, 50 mM $CaCl_2$) is added slowly, with repeated mixing of the tubes. After incubation for 20 minutes at room temperature, suspensions are diluted with 5 ml 1.2 M sorbitol, mixed by inversion and centrifuged for 10 minutes at 4000 rpm at room temperature. The protoplasts are resuspended gently in 1 ml 1.2 M sorbitol and plated onto solid selective regeneration medium consisting of either *Aspergillus* minimal medium without riboflavin, thiamine.HCL, nicotinamide, pyridoxine, panthotenic acid, biotin, casaminoacids and glucose. In case of acetamide selection the medium contains 10 mM acetamide as the sole nitrogen source and 1 M sucrose as osmoticum and C-source. Alternatively, protoplasts are plated onto PDA (Potato Dextrose Agar, Oxoid) supplemented with 1-50 microgram/ml phleomycin and 1M sucrose as osmosticum. Regeneration plates are solidified using 2% agar (agar No. 1, Oxoid L11). After incubation for 6-10 days at 30 degrees Celsius, conidiospores of transformants are transferred to plates consisting of *Aspergillus* selective medium (minimal medium containing acetamide as sole nitrogen source in the case of acetamide selection or PDA supplemented with 1-50 microgram/ml phleomycin in the case of phleomycin selection) with 2% glucose and 1.5% agarose (Invitrogen) and incubated for 5-10 days at 30 degrees Celsius. Single transformants are isolated and this selective purification step is repeated once upon which purified transformants are stored.

1.3. Shake Flask Growth of *A. Niger*

In total 10 transformants are selected for each construct and the presence of the construct is confirmed by PCR using primers specific for the constructs. Subsequently spores are inoculated in 100 ml *Aspergillus* minimal enriched medium comprising 100 g/l glucose. Strains are grown in an incubator at 250 rotations per minute for four days at 34 degrees Celsius. The supernatant of the culture medium is analysed for oxalic acid, malic acid, fumaric acid and succinic acid formation by HPLC and compared to a non transformed strain.

1.4 HPLC Analysis

HPLC is performed for the determination of organic acids and sugars in different kinds of samples. The principle of the separation on a Phenomenex Rezex-RHM-Monosaccharide column is based on size exclusion, ion-exclusion and ion-exchange using reversed phase mechanisms. Detection takes place by differential refractive index and ultra violet detectors.

Example 2A

Cloning of Fumarate Reductases from *Trypanosoma Brucei* in *Saccharomyces Cerevisiae*

2A.1. Expression Constructs

Figure 2:
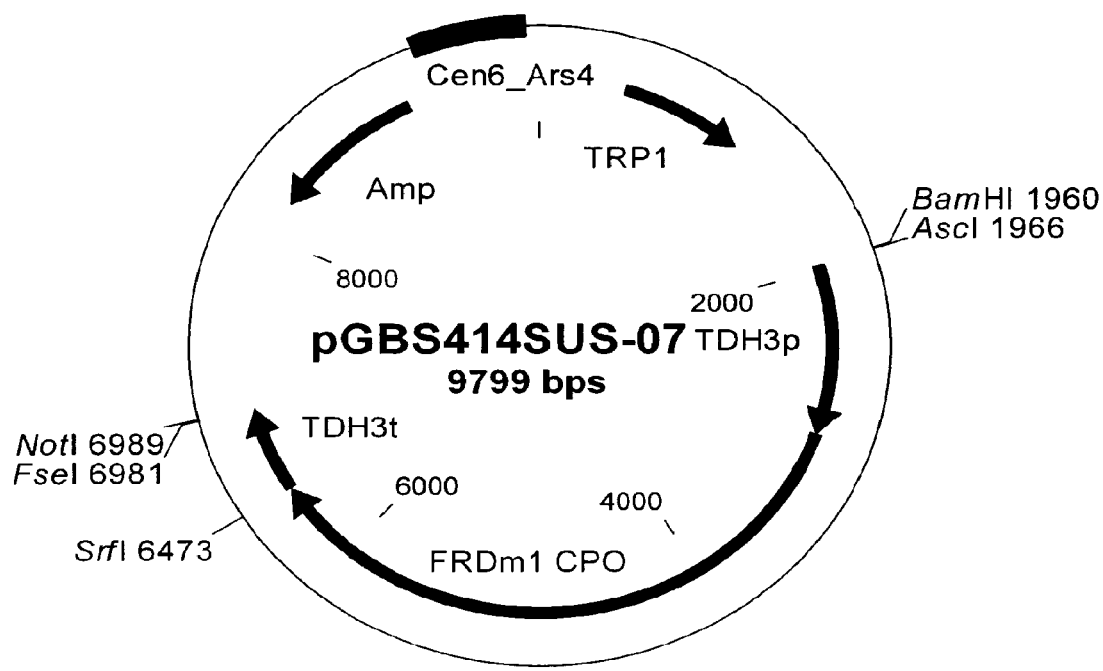
FIG. 2: Plasmid map of pGBS414SUS-07, encoding mitochondrial fumarate reductase m1 (FRDm1) from *Trypanosoma brucei* for expression in *Saccharomyces cerevisiae*. CPO denotes codon pair optimized.

Mitochondrial fumarate reductase m1 (FRDm1) [E.C. 1.3.1.6], GenBank accession number 60460035, from *Trypanosoma brucei* was analysed for the presence of signal sequences and codon optimized as described in section 1.1 for expression in *S. cerevisiae*. The resulting sequence SEQ ID NO: 9 was put behind the constitutive TDH3 promoter sequence SEQ ID NO: 12 and before the TDH3 terminator sequence SEQ ID NO: 13, and convenient restriction sites were added. The stop codon TGA in SEQ ID NO: 9 was modified to TAAG. The resulting sequence was synthesised at Sloning (Puchheim, Germany). The expression construct pGBS414SUS-07 was created after a BamHI/NotI restriction of the *S. cerevisiae* expression vector pRS414 (Sirkoski R. S. and Hieter P, Genetics, 1989, 122(1):19-27) and subsequently ligating in this vector a BamHI/NotI restriction fragment consisting of the fumarate reductase synthetic gene construct (FIG. 2). The ligation mix is used for transformation of *E. coli* DH10B (Invitrogen) resulting in the yeast expression construct pGBS414SUS-07 (FIG. 2).

Figure 3:
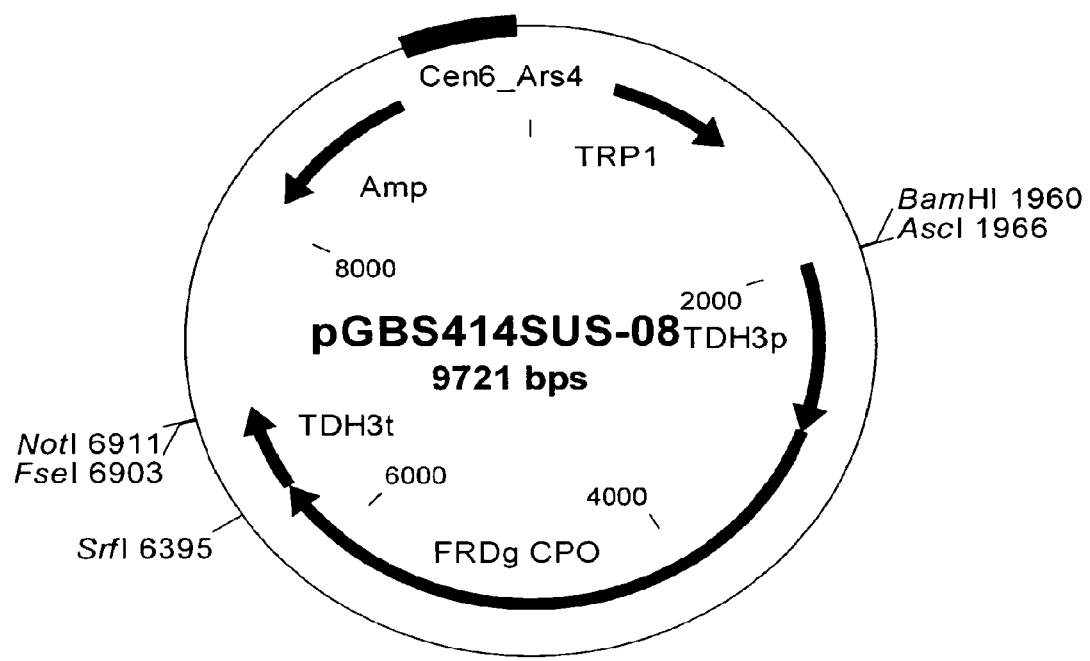
FIG. 3: Plasmid map of pGBS414SUS-08, encoding glycosomal fumarate reductase (FRDg) from *Trypanosoma brucei* for expression in *Saccharomyces cerevisiae*. CPO denotes codon pair optimized.

Likewise, glycosomal fumarate reductase (FRDg) [E.C. 1.3.1.6], GenBank accession number 23928422, from *Trypanosoma brucei* was analysed for peroxisomal targeting and codon optimisation was applied as described in section 1.1 for expression in *S. cerevisiae*. The resulting sequence SEQ ID NO: 10 was put behind the constitutive TDH3 promoter sequence SEQ ID NO: 12 and before the TDH3 terminator sequence SEQ ID NO: 13, and convenient restriction sites were added. The stop codon TGA in SEQ ID NO: 10 was modified to TAAG. The resulting sequence was synthesised at Sloning (Puchheim, Germany). The expression construct pGBS414SUS-08 was created after a BamHI/NotI restriction of the *S. cerevisiae* expression vector pRS414 (Sirkoski R. S. and Hieter P, Genetics, 1989, 122(1):19-27) and subsequently ligating in this vector a BamHI/NotI restriction fragment consisting of the fumarate reductase synthetic gene construct (FIG. 3). The ligation mix is used for transformation of *E. coli* DH10B (Invitrogen) resulting in the yeast expression construct pGBS414SUS-08 (FIG. 3).

The constructs pGBS414SUS-07 and pGBS414SUS-08 are independently transformed into *S. cerevisiae* strains CEN.PK113-6B (MATA ura3-52 leu2-112 trp1-289), RWB066 (MATA ura3-52 leu2-112 trp1-289 adh1::lox adh2::Kanlox) and RWB064 (MATA ura3-52 leu2-112 trp1-289 adh1::lox adh2::lox gpd1::Kanlox). Transformation mixtures are plated on Yeast Nitrogen Base (YNB) w/o AA (Difco)+2% glucose supplemented with appropriate amino acids. Transformants are inoculated in Verduyn medium comprising glucose supplemented with appropriate amino acids (Verduyn et al., 1992, Yeast. July; 8(7):501-17) and grown under aerobic, anaerobic and oxygen-limited conditions in shake flasks. The medium for anaerobic cultivation is supplemented with 0.01 g/l ergosterol and 0.42 g/l Tween 80 dissolved in ethanol (Andreasen and Stier, 1953, J. cell. Physiol, 41, 23-36; Andreasen and Stier, 1954, J. Cell. Physiol, 43: 271-281). All yeast cultures are grown at 30° C. in a shaking incubator at 250-280 rpm. At different incubation times, aliquots of the cultures are removed, centrifuged and the medium is analysed by HPLC for formation of oxalic acid, malic acid, fumaric acid and succinic acid as described in section 1.4.

Example 2B

Cloning of Fumarate Reductases from *Trypanosoma Brucei* in *Saccharomyces Cerevisiae*

2B.1. Expression Constructs

Figure 7:
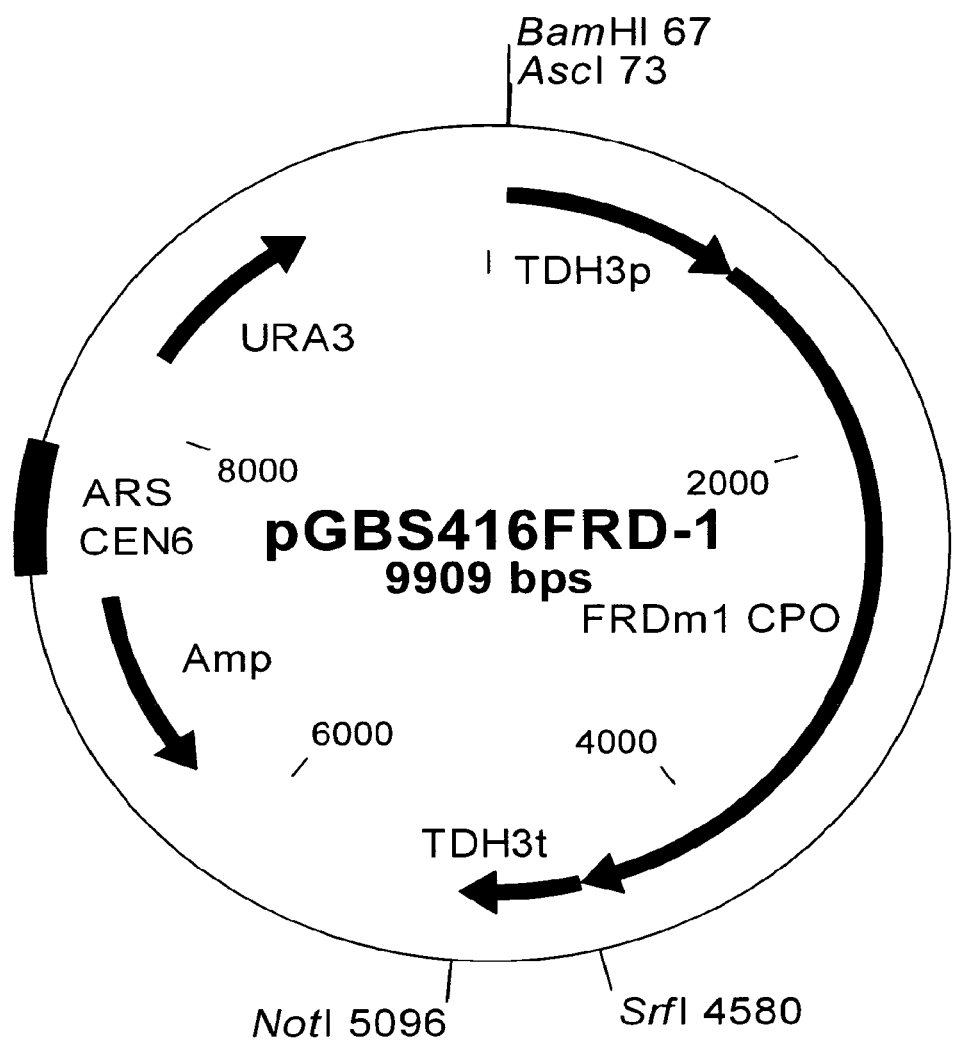
FIG. 7: Plasmid map of pGBS416FRD-1, encoding mitochondrial fumarate reductase m1 (FRDm1) from *Trypanosoma brucei* for expression in *Saccharomyces cerevisiae*. CPO denotes codon pair optimized.

In a similar way as disclosed in Example 2A.1. mitochondrial fumarate reductase from *Trypanosoma brucei* (FRDm, SEQ ID NO: 9) was ligated in a *S. cerevisiae* expression vector pRS416 (Sirkoski R. S. and Hieter P, Genetics, 1989, 122(1):19-27). The ligation mix was used for transformation of *E. coli* TOP10 cells (Invitrogen) resulting in the yeast expression constructs and pGBS416FRD-1 (FIG. 7).

Figure 8:
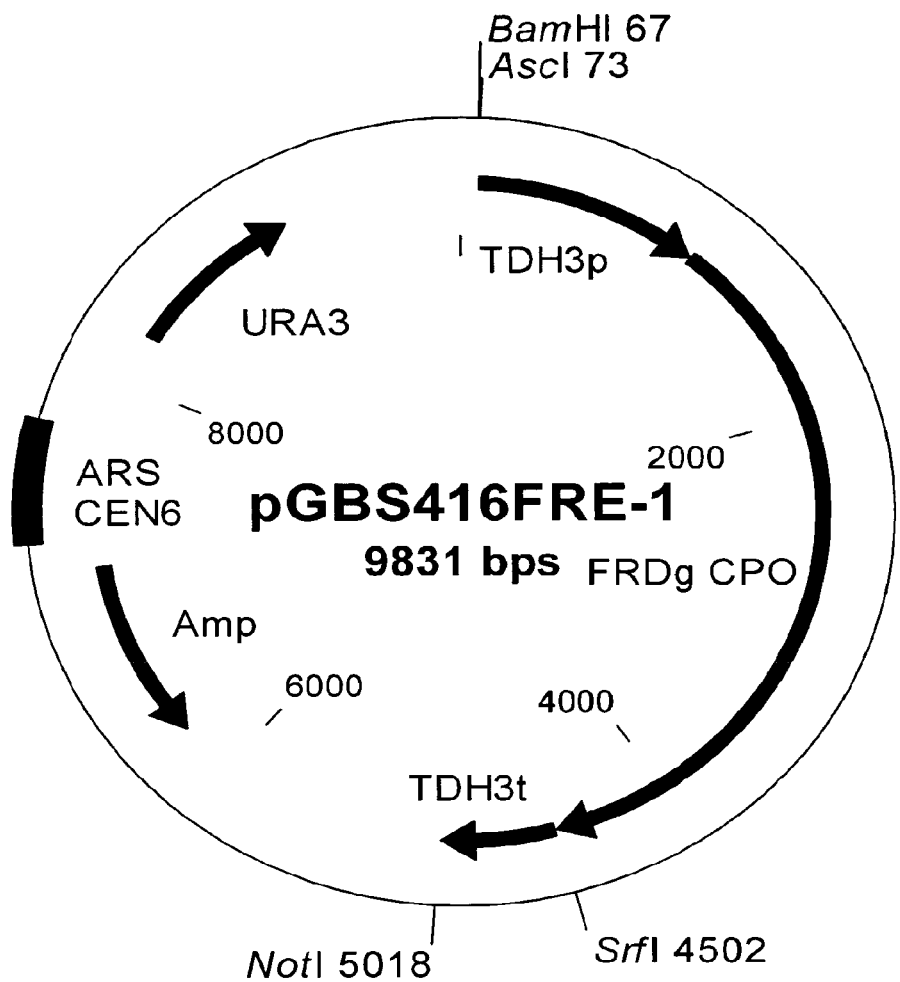
FIG. 8: Plasmid map of pGBS416FRE-1, encoding glycosomal fumarate reductase (FRDg) from *Trypanosoma brucei* for expression in *Saccharomyces cerevisiae*. CPO denotes codon pair optimized.

Likewise, glycosomal fumarate reductase (FRDg, SEQ ID NO: 10) from *Trypanosoma brucei* was ligated in an *S. cerevisiae* expression vector pRS416. The ligation mix was used for transformation of *E. coli* TOP10 cells (Invitrogen) resulting in the yeast expression construct pGBS416FRE-1 (FIG. 8).

2B.2. Transformation and Microtiterplates (MTP's) Growth Experiments

The constructs pGBS416FRD-1 and pGBS416FRE-1 were independently transformed into *S. cerevisiae* strain CEN.PK113-5D (MATA ura3-52). As negative control, empty vector pRS416 was transformed into strain CEN.PK 113-5D. Transformation mixtures were plated on Yeast Nitrogen Base (YNB) w/o AA (Difco)+2% glucose. The following numbers of individual transformants were inoculated in duplo in 250 microliters Verduyn medium comprising 2% glucose in 96 deep-well MTP's and pre-cultured at 30 degrees Celsius, 550 rpm, and a humidity of 80% in an Infors Microplate shaking incubator: 12 pGBS416FRD-1 (FRDm1), 12 pGBS416FRE-1 (FRDg) and 24 pRS416 empty vector control transformants. After 3 days, 25 microliters of the pre-culture present in the wells of the MTP plates was transferred to new 96 deep-well MTP's containing Verduyn medium containing glucose and CaCO$_3$ (end-concentrations: glucose 10%, CaCO3 1% w/v in a total volume of 250 microliters). After 3 and 7 days of growth at 30° C., 550 rpm, and a humidity of 80% in an Infors Microplate shaking incubator, the MTP's were centrifuged for 2 minutes at 2000 rpm, and 200 microliters of supernatant was harvested using the Multimek 96 (Beckman). The supernatant was analyzed by HPLC as described in Example 1.4 for the presence succinic acid. The results are shown in Table 1.

TABLE 1

Effect of introduction of mitochondrial (FRDm1) and glycosomal fumarate reductase (FRDg) from *T. brucei* in *S. cerevisiae* on the succinic acid production levels after 3 and 7 days of incubation

| S. cerevisiae comprising plasmid: | Succinic acid (mg/l) after 3 days | Succinic acid (mg/l) after 7 days |
|---|---|---|
| Empty vector pRS416 | 138 ± 18 (n = 48) | 203 ± 48 (n = 48) |
| pGBS4 16FRD-1 (FRDm1) | 340 ± 65 (n = 24) | 399 ± 72 (n = 24) |
| pGBS4 16FRE-1 (FRDg) | 489 ± 30 (n = 24) | 516 ± 57 (n = 24) |

The results in Table 1 show that introduction and overexpression of mitochondrial fumarate reductase (FRDm1) from *T. brucei* resulted in increased succinic acid production levels (2.47 fold, p=6.96E-14, Student's t-test, after 3 days incubation and 1.97 fold, p=8.63E-14, Student's t-test after 7 days incubation).

Likewise, introduction and overexpression of glycosomal fumarate reductase (FRDg) from *T. brucei* resulted in increased succinic acid production levels (3.55 fold, p=5.08E-32, Student's t-test, after 3 days incubation and a 2.55 fold increase, p=8.63E-25, Student's t-test after 7 days incubation).

Example 2C

Expression of PEP Carboxykinase from *Actinobacillus succinogenes* or *Mannheimia succiniciproducens* and Malate Dehydrogenase from *Saccharomyces cerevisiae* and Fumarase from *Rhizopus oryzae* and Fumarate Reductase from *Trypanosoma brucei* in *Saccharomyces cerevisiae*

2C.1 Gene Sequences
Phosphoenolpyruvate Carboxykinase:

Phosphoenolpyruvate carboxykinase [E.C. 4.1.1.49], Gen Bank accession number 152977907, from *Actinobacillus succinogenes* was analysed for the presence of signal sequences using SignalP 3.0 (www.cbs.dtu.dk/services/SignalP/) Bendtsen, J. et al. (2004) Mol. Biol., 340:783-795 and TargetP 1.1 (www.cbs.dtu.dk/services/TargetP/) Emanuelsson, O. et al. (2007) Nature Protocols 2, 953-971. Analysis as described by Schluter et al., (2007) NAR, 35, D815-D822 revealed a putative PTS2 signal sequence at position 115-123. The *A. succinogenes* sequence was modified to resemble the *Mannheimia succiniciproducens* protein sequence by replacing the amino acids EGY at position 120-122 with DAF resulting in amino acid sequence SEQ ID NO: 14 (nucleotide sequence SEQ ID NO: 15). SEQ ID NO: 14 was subjected to the codon-pair method as disclosed in WO2008/000632 for *S. cerevisiae*. The stop codon TAA in the resulting nucleotide sequence SEQ ID NO: 16 was modified to TAAG. This SEQ ID NO: 16 containing stop codon TAAG was put behind the constitutive TDH1 promoter sequence SEQ ID NO: 25 and before the TDH1 terminator sequence SEQ ID NO: 26, and convenient restriction sites were added. The resulting sequence SEQ ID NO: 29 was synthesised at Sloning (Puchheim, Germany).

Likewise phosphoenolpyruvate carboxykinase [E.C. 4.1.1.49], GenBank accession number 52426348, from *Mannheimia succiniciproducens* was analysed for the presence of signal sequences as described in Schlüter et al., (2007) NAR, 35, D815-D822. The sequence as shown in SEQ ID NO: 17 required no modifications. SEQ ID NO: 17 was subjected to the codon-pair method as disclosed in WO2008/000632 for *S. cerevisiae*. The stop codon TAA in the resulting sequence SEQ ID NO: 18 was modified to TAAG. SEQ ID NO: 18 containing stop codon TAAG was put behind the constitutive TDH1 promoter sequence SEQ ID NO: 25 and before the TDH1 terminator sequence SEQ ID NO: 26. Convenient restriction sites were added. The resulting synthetic construct (SEQ ID NO: 30) was synthesised at Sloning (Puchheim, Germany).

Malate Dehydrogenase

Cytoplasmic malate dehydrogenase (Mdh2p) [E.C. 1.1.1.37], GenBank accession number 171915, is regulated by carbon catabolite repression: transcription of MDH2 is repressed and Mdh2p is degraded upon addition of glucose to glucose-starved cells. Mdh2p deleted for the 12 amino-terminal amino acids is less-susceptible for glucose-induced degradation (Minard and McAlister-Henn, J Biol Chem. 1992 Aug. 25; 267(24):17458-64). To avoid glucose-induced degradation of Mdh2, the nucleotides encoding the first 12 amino acids were removed, and a new methionine amino acid was introduced (SEQ ID NO: 19) for overexpression of Mdh2 in S. cerevisiae. SEQ ID NO: 19 was subjected to the codon-pair method as disclosed in WO2008/000632 for S. cerevisiae. The stop codon TAA in the resulting in SEQ ID NO: 20, was modified to TAAG. SEQ ID NO: 20 containing a modified stop codon TAAG, encoding delta12NMDH2, was put behind the constitutive TDH3 promoter sequence SEQ ID NO: 12 and before the TDH3 terminator sequence SEQ ID NO: 13, and convenient restriction sites were added. The resulting synthetic construct (SEQ ID NO: 31) was synthesised at Sloning (Puchheim, Germany).

Peroxisomal malate dehydrogenase (Mdh3p) [E.C. 1.1.1.37], GenBank accession number 1431095, was analysed for peroxisomal targeting in filamentous fungi using the PTS1 predictor
(mendel.imp.ac.at/mendeljsp/sat/pts1/PTS1predictor.jsp with the fungi-specific prediction function. The C-terminal amino acids at position 341-343 (SKL) were removed from protein MDH3 resulting in SEQ ID NO: 21. SEQ ID NO: 21 was subjected to the codon-pair method as disclosed in WO2008/000632 for S. cerevisiae. The stop codon TGA in the resulting sequence SEQ ID NO: 22 was modified to TAAG. SEQ ID NO: 22 containing TAAG as stop codon was synthesized behind the constitutive TDH3 promoter sequence SEQ ID NO: 27 (600 by upstream of start codon) and before the TDH3 terminator sequence SEQ ID NO: 28 (300 by downstream of stop codon), and convenient restriction sites were added. The resulting sequence SEQ ID NO: 32 was synthesised at Sloning (Puchheim, Germany).

Fumarase:

Fumarase [E.C. 4.2.1.2], GenBank accession number 469103, from *Rhizopus oryzae* (FumR) was analysed for the presence of signal sequences using SignalP 3.0 (www.cbs.dtu.dk/services/SignalP/) Bendtsen, J. et al. (2004) Mol. Biol., 340:783-795 and TargetP 1.1 (www.cbs.dtu.dk/services/TargetP/) Emanuelsson, O. et al. (2007) Nature Protocols 2, 953-971. A putative mitochondrial targeting sequence in the first 23 amino acid of the protein was identified. To avoid potential targeting to mitochondria in S. cerevisiae, the first 23 amino acids were removed from FumR and a methionine amino acid was reintroduced resulting in SEQ ID NO: 23. SEQ ID NO: 23 was subjected to the codon-pair method as disclosed in WO2008/000632 for S. cerevisiae resulting in SEQ ID NO: 24. The stop codon TAA in SEQ ID NO: 24 was modified to TAAG. SEQ ID NO: 24 containing TAAG as stop codon was synthesized behind the constitutive TDH1 promoter sequence SEQ ID NO: 25 and before the TDH1 terminator sequence SEQ ID NO: 26 and convenient restriction sites were added. The resulting synthetic construct SEQ ID NO: 33 was synthesised at Sloning (Puchheim, Germany).

Fumarate Reductase:

Gene sequences of mitochondrial fumarate reductase (FRDm1) and glycosomal fumarate reductase (FRDg) from *T. brucei* were designed and synthesized as described under 2A.1.

2C.2. Construction of Expression Constructs

Figure 9:
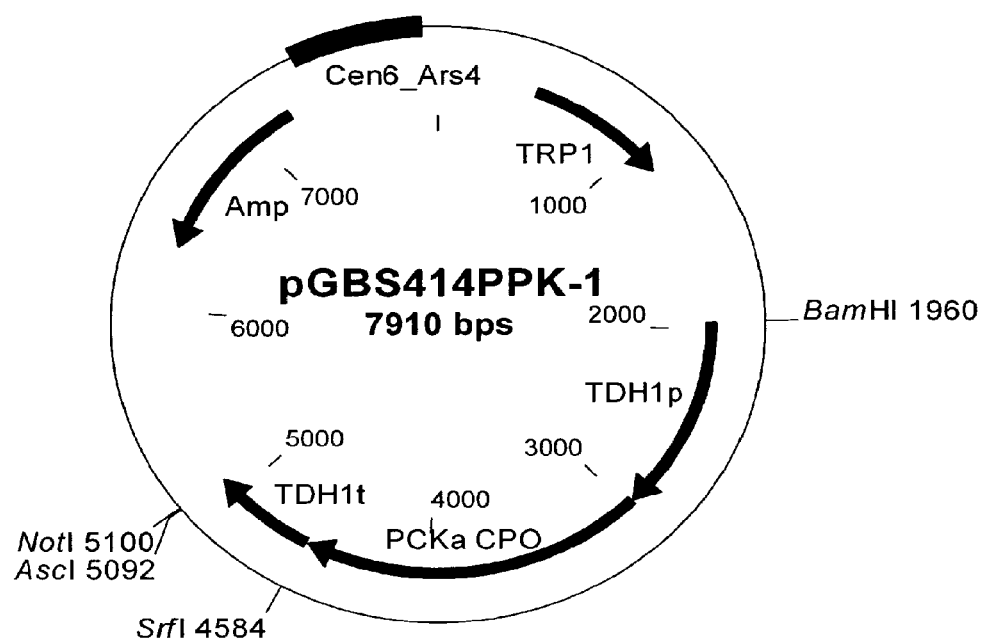
FIG. 9: Plasmid map of pGBS414PPK-1, containing PEP carboxykinase from *Actinobacillus succinogenes* (PCKa) for expression in *Saccharomyces cerevisiae*. The synthetic gene construct TDH1 promoter-PCKa-TDH1 terminator was cloned into expression vector pRS414. CPO denotes codon pair optimized.
Figure 10:
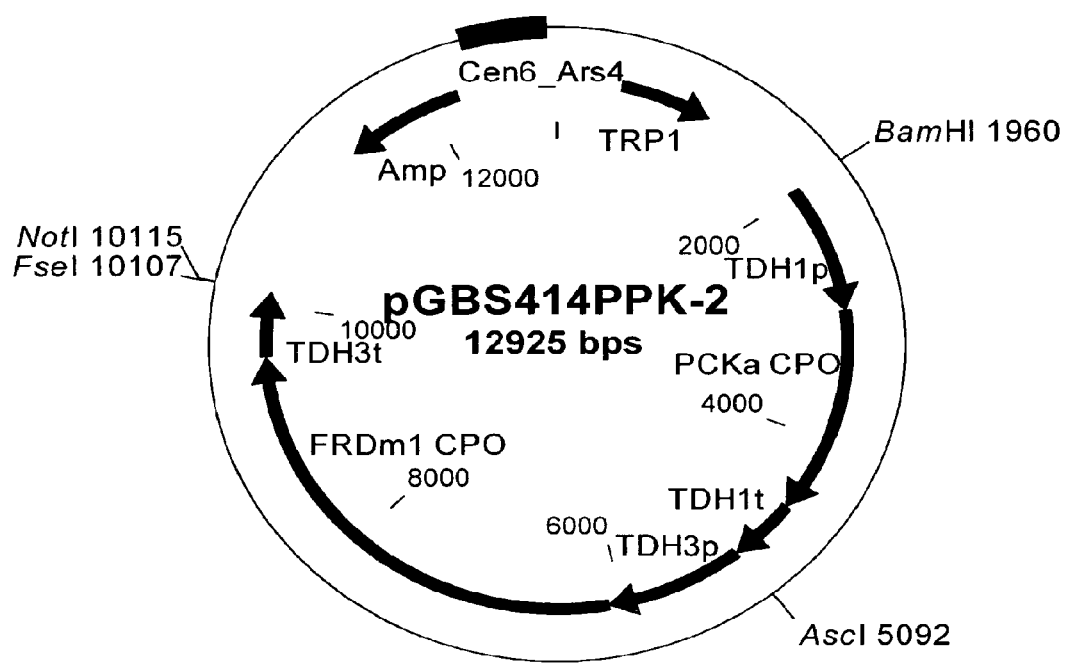
FIG. 10: Plasmid map of pGBS414PPK-2, containing PEP carboxykinase from *Actinobacillus succinogenes* (PCKa) and mitochondrial fumarate reductase m1 from *Trypanosoma brucei* (FRDm1) for expression in *Saccharomyces cerevisiae*. The synthetic gene constructs TDH1 promoter-PCKa-TDH1 terminator and TDH3 promoter-FRDm1-TDH3 terminator were cloned into expression vector pRS414. CPO denotes codon pair optimized.
Figure 11:
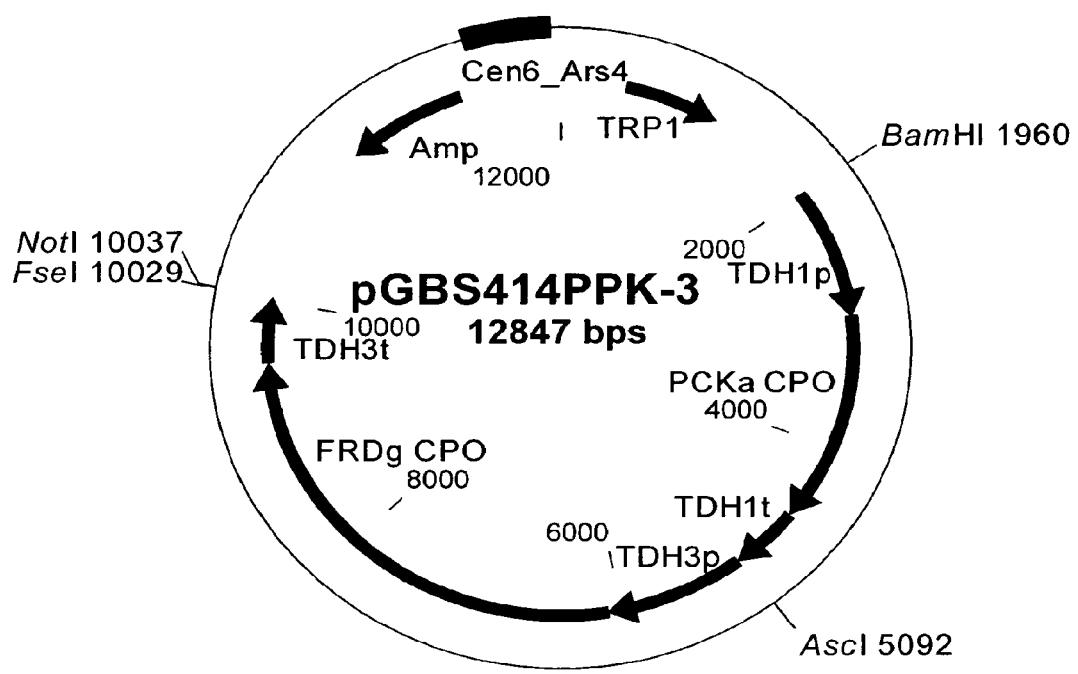
FIG. 11: Plasmid map of pGBS414PPK-3, containing PEP carboxykinase from *Actinobacillus succinogenes* (PCKa) and glycosomal fumarate reductase from *Trypanosoma brucei* (FRDg) for expression in *Saccharomyces cerevisiae*. The synthetic gene constructs TDH1 promoter-PCKa-TDH1 terminator and TDH3 promoter-FRDg-TDH3 terminator were cloned into expression vector pRS414. CPO denotes codon pair optimized.

The expression constructs pGBS414PPK-1 (FIG. 9), pGBS414PPK-2 (FIG. 10) and pGBS414PPK-3 (FIG. 11) were created after a BamHI/NotI restriction of the S. cerevisiae expression vector pRS414 (Sirkoski R. S. and Hieter P, Genetics, 1989, 122(1):19-27) and subsequently ligating in this vector a BamHI/NotI restriction fragment consisting of the phosphoenolpyruvate carboxykinase (origin *Actinobacillus succinogenes*) synthetic gene construct (SEQ ID NO: 29). The ligation mix was used for transformation of *E. coli* TOP10 (Invitrogen) resulting in the yeast expression construct pGBS414PPK-1. Subsequently, pGBK414PPK-1 was restricted with AscI and NotI. To create pGBS414PPK-2, an AscI/NotI restriction fragment consisting of mitochondrial fumarate reductase from *T. brucei* (FRDm1) synthetic gene construct (SEQ ID NO: 34) was ligated into the restricted pGBS414PPK-1 vector. The ligation mix was used for transformation of *E. coli* TOP10 (Invitrogen) resulting in the yeast expression construct pGBS414PPK-2 (FIG. 10). To create pGBS414PPK-3, an AscI/NotI restriction fragment consisting of glycosomal fumarate reductase from *T. brucei* (FRDg) synthetic gene construct (SEQ ID NO: 35) was ligated into the restricted pGBS414PPK-1 vector. The ligation mix was used for transformation of *E. coli* TOP10 (Invitrogen) resulting in the yeast expression construct pGBS414PPK-3 (FIG. 11).

Figure 12:
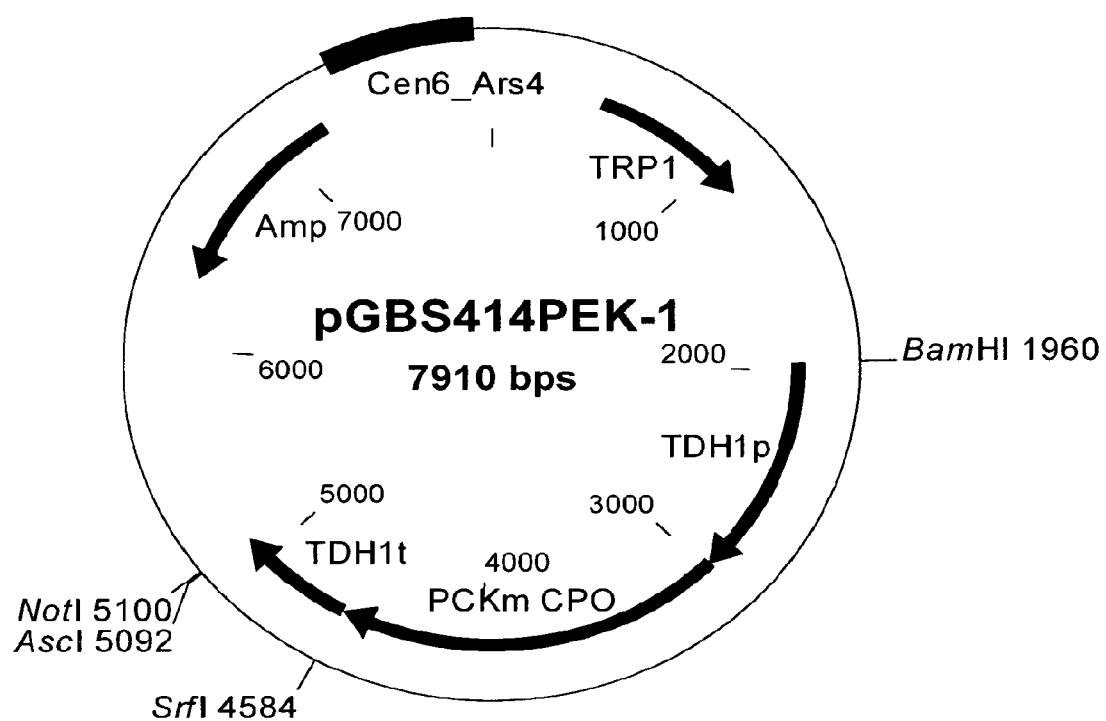
FIG. 12: Plasmid map of pGBS414PEK-1, containing PEP carboxykinase from *Mannheimia succiniciproducens* (PCKm) for expression in *Saccharomyces cerevisiae*. The synthetic gene construct TDH1 promoter-PCKm-TDH1 terminator was cloned into expression vector pRS414. CPO denotes codon pair optimized.
Figure 13:
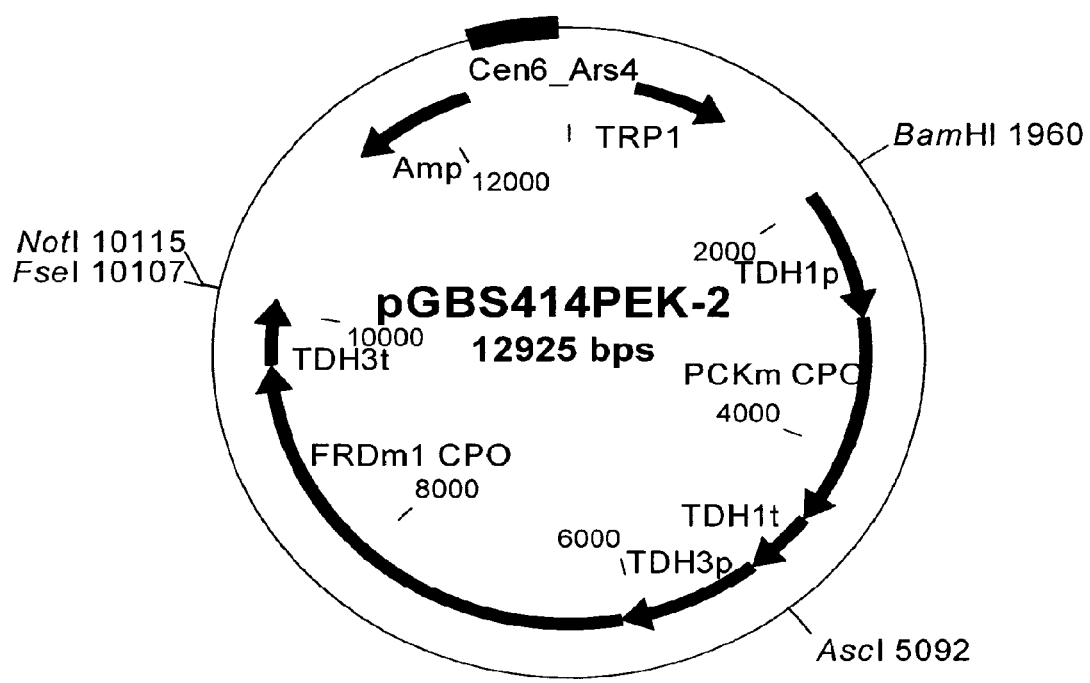
FIG. 13: Plasmid map of pGBS414PEK-2, containing PEP carboxykinase from *Mannheimia succiniciproducens* (PCKm) and mitochondrial fumarate reductase m1 from *Trypanosoma brucei* (FRDm1) for expression in *Saccharomyces cerevisiae*. The synthetic gene constructs TDH1 promoter-PCKm-TDH1 terminator and TDH3 promoter-FRDm1-TDH3 terminator were cloned into expression vector pRS414. CPO denotes codon pair optimized.
Figure 14:
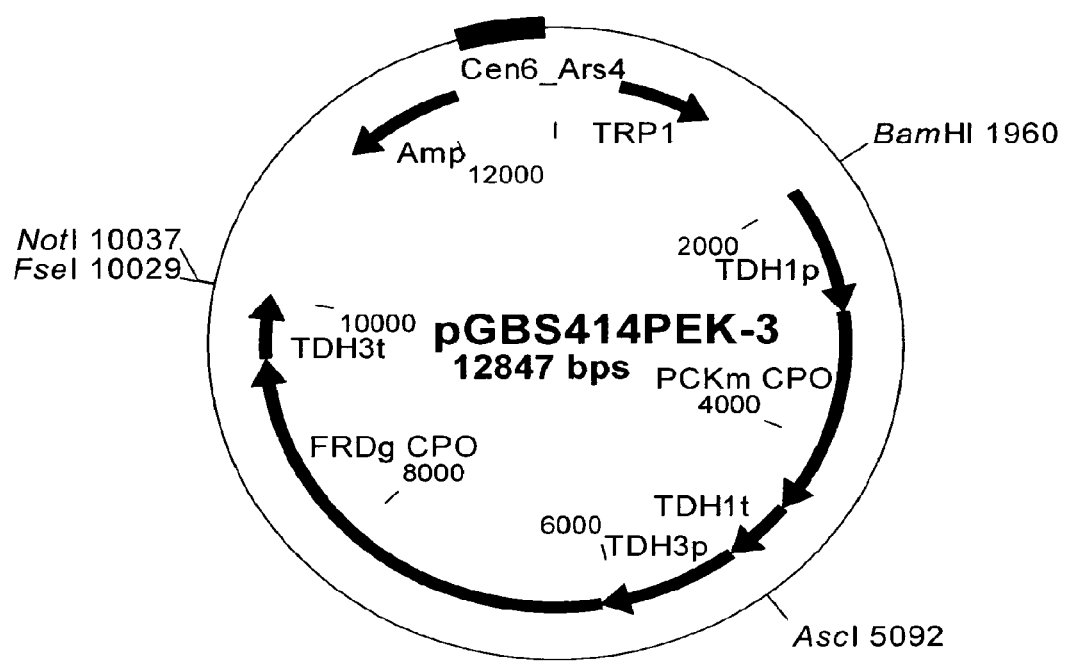
FIG. 14: Plasmid map of pGBS414PEK-3, containing PEP carboxykinase from *Mannheimia succiniciproducens* (PCKm) and glycosomal fumarate reductase from *Trypanosoma brucei* (FRDg) for expression in *Saccharomyces cerevisiae*. The synthetic gene constructs TDH1 promoter-PCKm-TDH1 terminator and TDH3 promoter-FRDg-TDH3 terminator were cloned into expression vector pRS414. CPO denotes codon pair optimized.

The expression constructs pGBS414PEK-1 (FIG. 12), pGBS414PEK-2 (FIG. 13) and pGBS414PEK-3 (FIG. 14) were created after a BamHI/NotI restriction of the S. cerevisiae expression vector pRS414 (Sirkoski R. S. and Hieter P, Genetics, 1989, 122(1):19-27) and subsequently ligating in this vector a BamHI/NotI restriction fragment consisting of the phosphoenolpyruvate carboxykinase (origin *Mannheimia succiniciproducens*) synthetic gene construct (SEQ ID NO: 30). The ligation mix was used for transformation of *E. coli* TOP10 (Invitrogen) resulting in the yeast expression construct pGBS414PEK-1. Subsequently, pGBK414PEK-1 was restricted with AscI and NotI. To create pGBS414PEK-2, an AscI/NotI restriction fragment consisting of mitochondrial fumarate reductase from *T. brucei* (FRDm1) synthetic gene construct (SEQ ID NO: 34) was ligated into the restricted pGBS414PEK-1 vector. The ligation mix was used for transformation of *E. coli* TOP10 (Invitrogen) resulting in the yeast expression construct pGBS414PEK-2 (FIG. 13). To create pGBS414PEK-3, an AscI/NotI restriction fragment consisting of glycosomal fumarate reductase from *T. brucei* (FRDg) synthetic gene construct (SEQ ID NO: 35) was ligated into the restricted pGBS414PEK-1 vector. The ligation mix was used for transformation of *E. coli* TOP10 (Invitrogen) resulting in the yeast expression construct pGBS414PEK-3 (FIG. 14).

Figure 15:
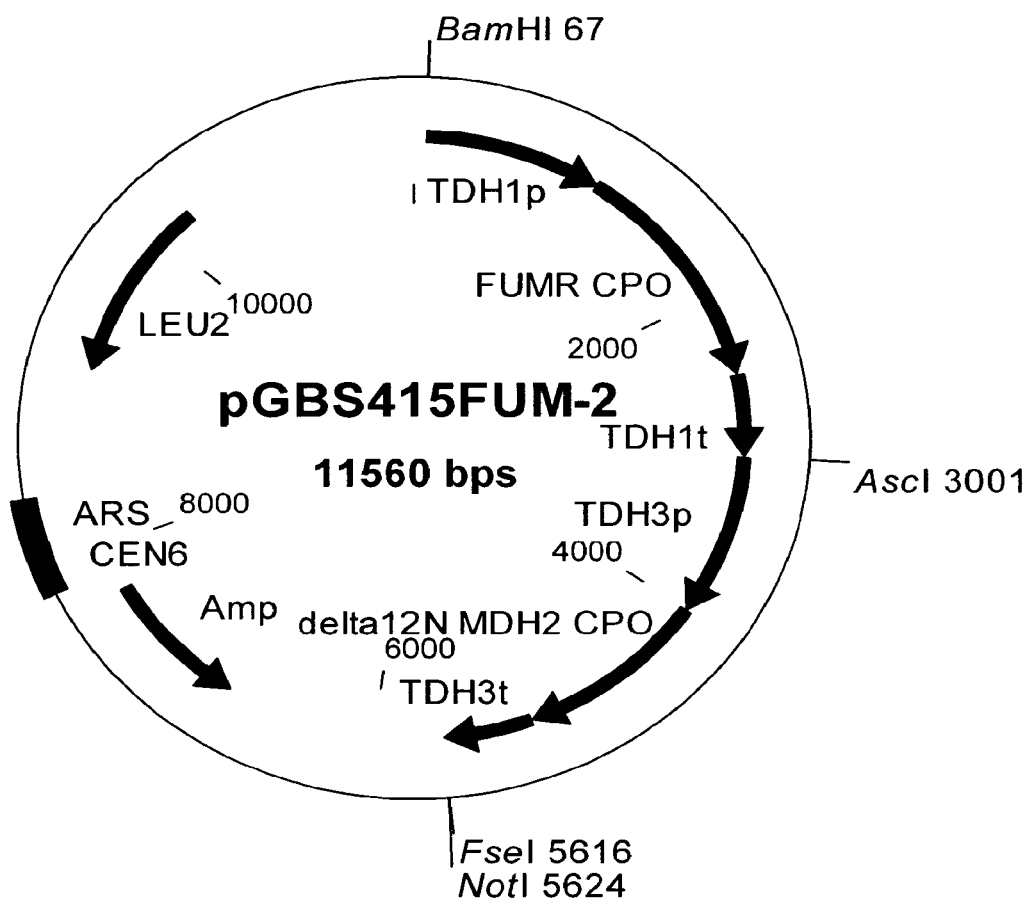
FIG. 15: Plasmid map of pGBS415FUM-2, containing fumarase from *Rhizopus oryzae* (FUMR) and cytoplasmic malate dehydrogenase from *Saccharomyces cerevisiae* truncated for the first 12 amino acids (delta12N MDH2) for expression in *Saccharomyces cerevisiae*. The synthetic gene constructs TDH1 promoter-FUMR-TDH1 terminator and DH3 promoter-MDH3-TDH3 terminator were cloned into expression vector pRS415. CPO denotes codon pair optimized.
Figure 16:
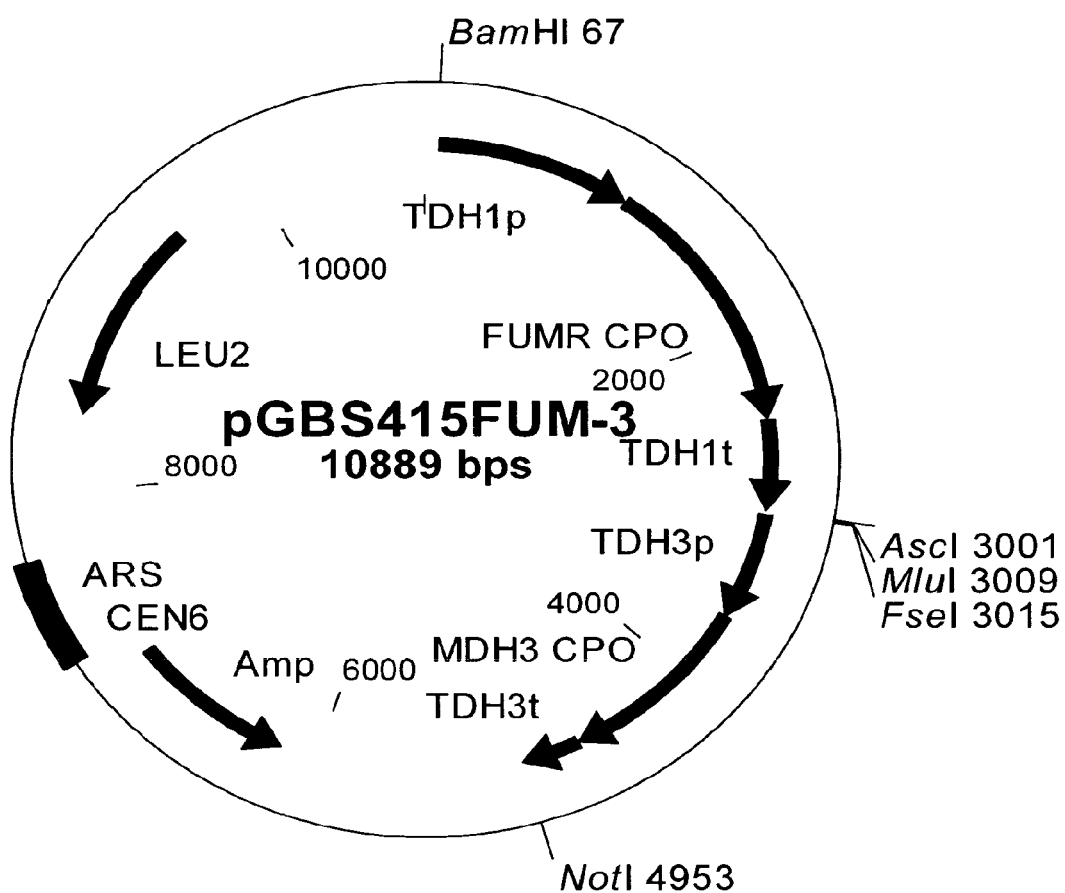
FIG. 16: Plasmid map of pGBS415FUM-3, containing fumarase from *Rhizopus oryzae* (FUMR) and peroxisomal malate dehydrogenase from *Saccharomyces cerevisiae* (MDH3) for expression in *Saccharomyces cerevisiae*. The synthetic gene constructs TDH1 promoter-FUMR-TDH1 terminator and TDH3 promoter-MDH3-TDH3 terminator were cloned into expression vector pRS415. CPO denotes codon pair optimized.

The expression constructs pGBS415FUM-2 (FIG. 15) and pGBS415FUM-3 (FIG. 16) were created after a BamHI/NotI restriction of the S. cerevisiae expression vector pRS415 (Sirkoski R. S. and Hieter P, Genetics, 1989, 122(1):19-27) and subsequently ligating in this vector a BamHI/NotI restriction fragment consisting of the fumarase (origin *Rhizopus oryzae*) synthetic gene construct (SEQ ID NO: 33). The ligation mix was used for transformation of *E. coli* TOP10 (Invitrogen) resulting in the yeast expression construct pGBS415FUM-1. Subsequently, pGBK415FUM-1 was restricted with AscI and NotI. To create pGBS415FUM-2, an AscI/NotI restriction fragment consisting of cytoplasmic malate dehydrogenase from *S. cerevisiae* (delta12N MDH2) synthetic gene construct (SEQ ID NO: 31) was ligated into the restricted pGBS415FUM-1 vector. The ligation mix was used for transformation of *E. coli* TOP10 (Invitrogen) resulting in the yeast expression construct pGBS415FUM-2 (FIG. 15). To create pGBS415FUM-3, an AscI/NotI restriction fragment consisting of peroxisomal malate dehydrogenase from *S. cerevisiae* (MDH3) synthetic gene construct (SEQ ID NO: 32) was ligated into the restricted pGBS415FUM-1 vector. The ligation mix was used for transformation of *E. coli* TOP10 (Invitrogen) resulting in the yeast expression construct pGBS415FUM-3 (FIG. 16).

2C.3. *S. cerevisiae* Strains

Figure 17:
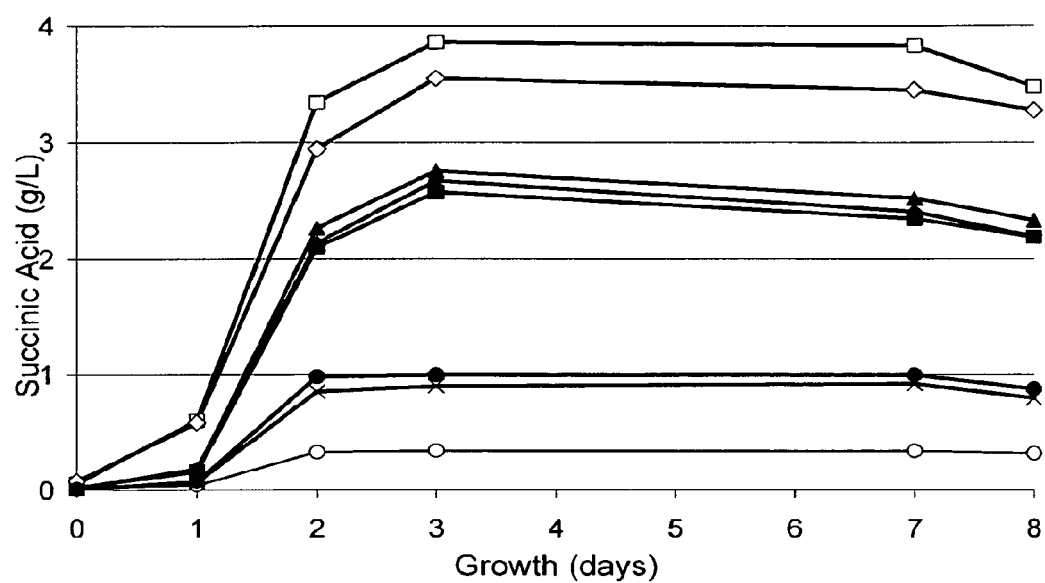
FIG. 17: Succinic acid levels in strains SUC-101 (○, empty vectors control), SUC-148 (■, overexpression of PCKa, MDH3, FUMR, FRDm1), SUC-149 (□, PCKa, MDH3, FUMR, FRDg), SUC-150 (♦, PCKm, MDH3, FUMR, FRDm1), SUC-151 (◇, PCKm, MDH3, FUMR, FRDg), SUC-152 (●, PCKa, MDH3, FUMR), SUC-154 (X, PCKm, MDH3, FUMR) and SUC-169 (▲, PCKm, delta12NMDH2, FUMR, FRDm1). All overexpressed genes were codon pair optimized for expression in S. cerevisiae. All data represent averages of 3 independent growth experiments of SUC-148, 149, 150, 151, 152, 154 and SUC-169 and averages of 6 independent growth experiments of SUC-101.

Different combinations of plasmids pGBS414PPK-1, pGBS414 PPK-2, pGBS414PPK-3, pGBS414PEK-1, pGBS414PEK-2, pGBS414PEK-3, pGBS415FUM-2, pGBS415-FUM-3 were transformed into *S. cerevisiae* strain CEN.PK113-6B (MATA ura3-52 leu2-112 trp1-289), resulting in the yeast strains depicted in Table 2. In addition to the mentioned plasmids, pRS416 (empty vector) was transformed to create prototrophic yeast strains. The expression vectors were transformed into yeast by electroporation. The transformation mixtures were plated on Yeast Nitrogen Base (YNB) w/o AA (Difco)+2% glucose.

flasks in a shaking incubator at 30° C. at 250 rpm. After 72 hours, the culture was centrifuged for 5 minutes at 4750 rpm. 1 ml supernatant was used to measure succinic acid levels by HPLC as described in section 1.4. The remaining supernatant was decanted and the pellet (cells) was resuspended in 1 ml production medium. The production medium consisted of Verduyn medium with 10% galactose (w/v) and 1% CaCO3 (w/v). The resuspended cells were inoculated in 50 ml production medium in 100 ml shake flasks and grown in a shaking incubator at 30° C. at 100 rpm. At various time points, 1 ml sample was taken from the culture succinic acid levels were measured by HPLC as described in section 1.4 (FIG. 17).

Strains transformed with empty vectors (control strain) produced up to 0.3 g/L succinic acid. Overexpression of PEP carboxykinase from *M. succiniciproducens* PCKm), peroxisomal malate dehydrogenase (MDH3) from *S. cerevisiae* and fumarase from *R. oryzae* (FUMR) resulted in production of 0.9 g/L succinic acid production. Overexpression of PEP carboxykinase from *A. succinogenes* (PCKa), MDH3 and FUMR resulted in a slight increase in succinic acid production to 1.0 g/L.

These results show that in *S. cerevisiae* as described increased succinic acid production about 3 times.

Additional overexpression of mitochondrial fumarate reductase (FRDm1) from *T. brucei* further increased succinic acid production levels; overexpression of PCKa, MDH3, FUMR, FRDm1 resulted in production of 2.6 g/L succinic acid, and overexpression of PCKm, MDH3, FUMR and FRDm1 resulted in production of 2.7 g/L succinic acid. Overexpression of delta12NMDH2 in combination with PCKm, FUMR and FRDm1 resulted in production of 2.7

TABLE 2

Yeast strains constructed for Example 2C.

| Name | Background | Plasmids | Genes |
| --- | --- | --- | --- |
| SUC-148 | CEN.PK113-6B | pGBS414PPK-2<br>pGBS415FUM-3<br>pRS416 (empty vector) | PCKa, FRDm1<br>FUMR, MDH3 |
| SUC-149 | CEN.PK113-6B | pGBS414PPK-3<br>pGBS415FUM-3<br>pRS416 (empty vector) | PCKa, FRDg<br>FUMR, MDH3 |
| SUC-150 | CEN.PK113-6B | pGBS414PEK-2<br>pGBS415FUM-3<br>pRS416 (empty vector) | PCKm, FRDm1<br>FUMR, MDH3 |
| SUC-151 | CEN.PK113-6B | pGBS414PEK-3<br>pGBS415FUM-3<br>pRS416 (empty vector) | PCKm, FRDg<br>FUMR, MDH3 |
| SUC-152 | CEN.PK113-6B | PGBS414PPK-1<br>pGBS415FUM-3<br>pRS416 (empty vector) | PCKa<br>FUMR, MDH3 |
| SUC-154 | CEN.PK113-6B | PGBS414PEK-1<br>pGBS415FUM-3<br>pRS416 (empty vector) | PCKm<br>FUMR, MDH3 |
| SUC-169 | CEN.PK113-6B | pGBS414PEK-2<br>pGBS415FUM-2<br>pRS416 (empty vector) | PCKm, FRDm1<br>FUMR, Δ12NMDH2 |
| SUC-101 | CEN.PK113-6B | pRS414 (empty vector)<br>pRS415 (empty vector)<br>pRS415 (empty vector) | |

2C.4. Growth Experiments and Succinic Acid Production

Transformants were inoculated in 20 ml pre-culture medium consisting of Verduyn medium (Verduyn et al., 1992, Yeast. July; 8(7):501-17) comprising 2% galactose (w/v) and grown under aerobic conditions in 100 ml shake g/L succinic acid, indicating that similar levels of succinic acid were produced using either truncated MDH2 or MDH3. Additional overexpression of glycosomal fumarate reductase (FRDg) from *T. brucei* resulted in an even higher increase in succinic acid production levels; overexpression of PCKa, MDH3, FUMR and FRDg resulted in production of 3.9 g/L succinic acid, whereas overexpression of PCKm, MDH3, FUMR and FRDg resulted in slightly lower production of 3.6 g/L succinic acid.

The results show addition of NAD(H) dependent fumarate reductase as disclosed herein in a *S. cerevisiae* comprising a genetic modification of PCKa/m, MDH3 and FUMR significantly increased succinic acid production levels.

Overexpression of FRDg had a more positive effect on succinic acid production levels in *S. cerevisiae* compared to overexpression of FRDm1 in *S. cerevisiae*.

Example 2D

Effect of Overexpression of a Dicarboxylic Acid Transporter on Succinic Acid Production in Succinic Acid Producing *S. cerevisiae* Cells 2D.1. Gene Sequences Malate permease, GenBank accession number 119368831, from *Schizosaccharomyces pombe* (SEQ ID NO: 36) was subjected to the codon-pair method as disclosed in WO2008/000632 for *S. cerevisiae* resulting in SEQ ID NO: 37. The stop codon TAA in SEQ ID NO: 37 was modified to TAAG. SEQ ID NO: 37 containing TAAG as stop codon was put behind the constitutive ENO1 promoter sequence SEQ ID NO: 38 and before the ENO1 terminator sequence SEQ ID NO: 39, and convenient restriction sites were added. In the ENO1 promotor, T at position 596 (−5) was changed to A in order to obtain a better Kozak sequence. The resulting sequence SEQ ID NO: 40 was synthesised at Sloning (Puchheim, Germany).

2D.2. Construction of Expression Constructs

Figure 18:
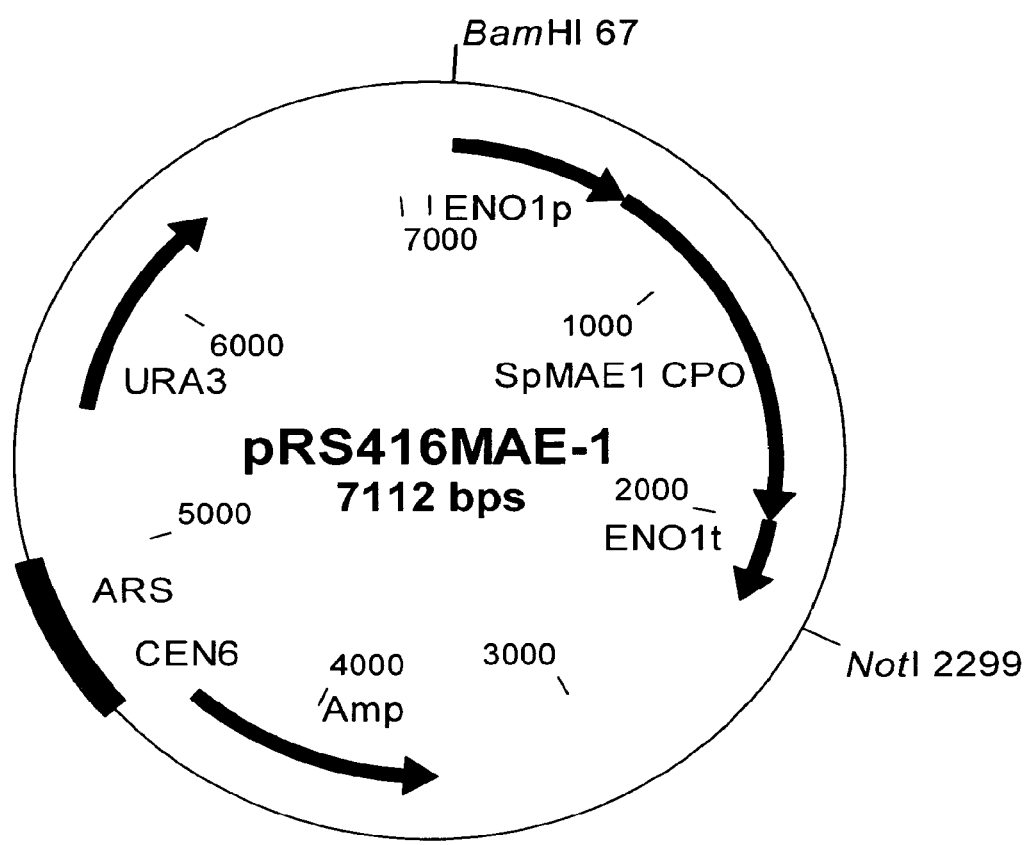
FIG. 18: Plasmid map of pGBS416MAE-1, containing malate permease from Schizosaccharomyces pombe (Sp-MAE1) for expression in Saccharomyces cerevisiae. The synthetic gene construct Eno1 promoter-MAE1-Eno1 terminator was cloned into expression vector pRS416. CPO denotes codon pair optimized.
Figure 19:
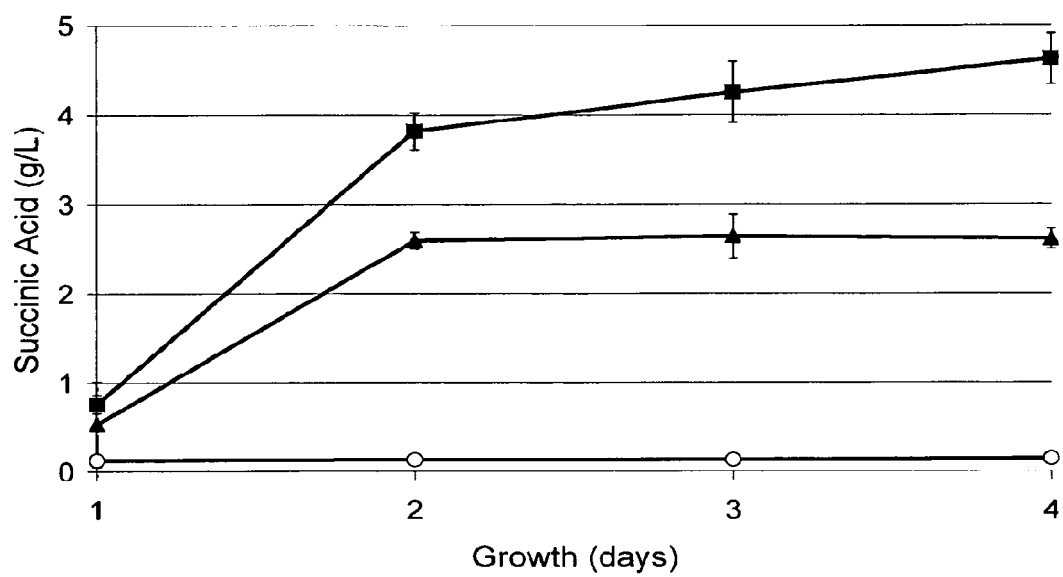
FIG. 19: Succinic acid levels in strains SUC-101 (○, empty vectors control), SUC-169 (▲, PCKm, delta12NMDH2, FUMR, FRDm1) and SUC-194 (■, PCKm, delta12NMDH2, FUMR, FRDm1, SpMAE1). All overexpressed genes were codon pair optimized for expression in S. cerevisiae. All data represent averages of 3 independent growth experiments of SUC-169 and SUC-194 and averages of 6 independent growth experiments of SUC-101.

The expression constructs pGBS416MAE-1 (FIG. 18) was created after a BamHI/NotI restriction of the *S. cerevisiae* expression vector pRS416 (Sirkoski R. S. and Hieter P, Genetics, 1989, 122(1):19-27) and subsequently ligating in this vector a BamHI/NotI restriction fragment consisting of the *Schizosaccharomyces pombe* malate transporter synthetic gene construct (SEQ ID NO: 40). The ligation mix was used for transformation of *E. coli* TOP10 (Invitrogen) resulting in the yeast expression construct pGBS416MAE-1.

2D.3. *S. cerevisiae* Strains

Plasmids pGBS414PEK-2, pGBS415FUM-2 and pGBS416MAE-1 (described under 2C.2.) were transformed into *S. cerevisiae* strain CEN.PK113-6B (MATA ura3-52 leu2-112 trp1-289) to create strain SUC-194, overexpressing PCKm, delta12NMDH2, FUMR, FRDm1 and SpMAE1. All genes were codon pair optimized for expression in *S. cerevisiae*.

The expression vectors were transformed into yeast by electroporation. The transformation mixtures were plated on Yeast Nitrogen Base (YNB) w/o AA (Difco)+2% glucose. Strains SUC-101 is described in Table 2.

2D.4. Growth Experiments and Succinic Acid Production in Wildtype CEN.PK Strains Growth parameters and sample analysis were performed as described under example 2C.4 with the following modifications: pre-culturing was performed using 2% glucose (w/v) as carbon source. In the production medium 10% glucose (w/v) was used as carbon source.

Strains transformed with empty vectors (control strain) produced up to 0.3 g/L succinic acid. Additional overexpression of SpMAE1 in strain SUC-194, overexpressing PCKm, delta12NMDH2, FUMR and FRDm1 resulted in increased succinic acid production levels to 4.6 g/L, whereas strain SUC-132, overexpressing PCKm, delta12NMDH2, FUMR and FRDm1 resulted in production of 2.7 g/L succinic acid.

The results show that insertion of a malate transporter in a *S. cerevisiae* comprising the genetic modifications as described herein further increased succinic acid production at least 1.5 times.

Example 2E

Effect of a Dicarboxylic Acid Transporter in *S. cerevisiae* Comprising a Deletion of the Genes Alcohol Dehydrogenase 1 and 2 (Adh1, Adh2) and the Gene Glycerol-3-Phosphate Dehydrogenase 1 (Gpd1) on Succinic Acid Production Levels 2E.1. Gene Sequences Described under 2D.1.

2E.2. Construction of Expression Constructs

Described under 2D.2.

2E.3. *S. cerevisiae* Strains

Plasmids pGBS414PPK-3, pGBS415FUM-3 and pGBS416MAE-1 (described under 2C.2.) were transformed into *S. cerevisiae* strain RWB064 (MA TA ura3-52 leu2-112 trp1-289 adh1::lox adh2::lox gpd1::Kanlox) to create strain SUC-201, overexpressing PCKa, MDH3, FUMR, FRDg and SpMAE1. All genes were codon pair optimized for expression in *S. cerevisiae*.

TABLE 3

Yeast strains constructed for Example 2D.

| Name | Background | Plasmids | Genes |
|---|---|---|---|
| SUC-132 | CEN.PK113-6B | pGBS414PEK-2<br>pGBS415FUM-2<br>pRS416 (empty vector) | PCKm, FRDm1<br>FUMR, Δ12NMDH2 |
| SUC-194 | CEN.PK113-6B | pGBS414PEK-2<br>pGBS415FUM-2<br>pRS416MAE-1 | PCKm, FRDm1<br>FUMR, Δ12NMDH2<br>SpMAE1 |

TABLE 4

Yeast strains constructed for Example 2E.

| Name | Background | Plasmids | Genes |
| --- | --- | --- | --- |
| SUC-200 | CEN.PK113-6B adh1::lox adh2::lox gpd1::Kanlox | PGBS414PPK-3 pGBS415FUM-3 pGBS416MAE-1 | PCKa, FRDg FUMR, MDH3 SpMAE1 |
| SUC-201 | CEN.PK113-6B adh1::lox adh2::lox gpd1::Kanlox | PGBS414PPK-3 pGBS415FUM-3 pRS416 (empty vector) | PCKa, FRDg FUMR, MDH3 |
| SUC-103 | CEN.PK113-6B adh1::lox adh2::lox gpd1::Kanlox | pRS414 (empty vector) pRS415 (empty vector) pRS415 (empty vector) | |

2E.4. Growth Experiments and Succinic Acid Production in CEN.PK Strains Deleted for the Genes Alcohol Dehydrogenase 1 and 2 (Adh1, Adh2) and the Gene Glycerol-3-Phosphate Dehydrogenase 1 (Gpd1)

Growth parameters and sample analysis were performed as described under example 2C.4 with the following modifications: pre-culturing was performed using 2% galactose (w/v) as carbon source. 5% galactose (w/v) was added to the production medium at t=0, 3 and 7 days.

Figure 20:
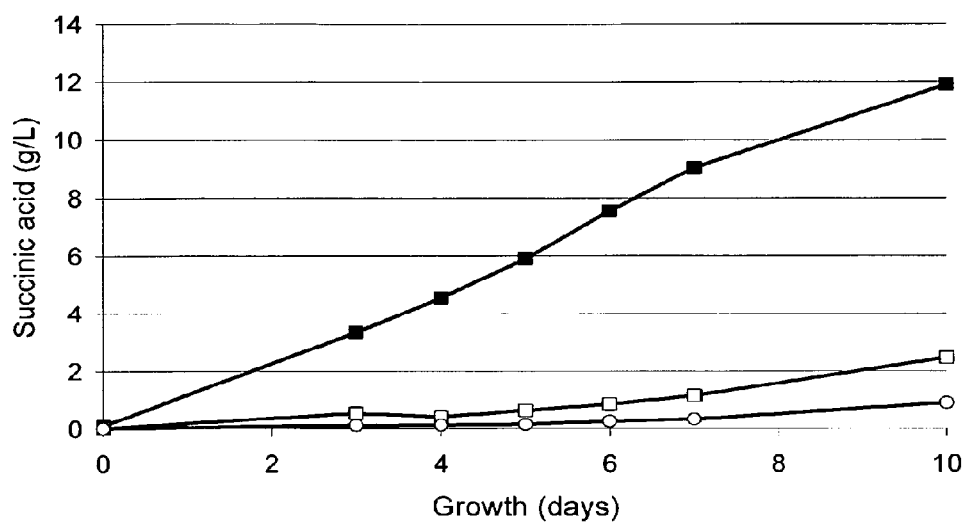
FIG. 20: Succinic acid levels in strains SUC-103 (○, adh1/2 and gpd1 deletion mutant; empty vectors control), SUC-201 (□, adh1/2 and gpd1 deletion mutant; PCKa, MDH3, FUMR, FRDg) and SUC-200 (■, adh1/2 and gpd1 deletion mutant; PCKa, MDH3, FUMR, FRDg, SpMAE1). All overexpressed genes were codon pair optimized for expression in S. cerevisiae.

Strain SUC-103 transformed with empty vectors (control strain) produced 0.9 g/L succinic acid after growth for 10 days in production medium (FIG. 20). Overexpression of PCKa, MDH3, FUMR and FRDg in strain RWB064 resulted in increased succinic acid production levels to 2.5 g/L (strain SUC-201, FIG. 20). Additional overexpression of SpMAE1 besides PCKa, MDH3, FUMR and FRDg in strain RWB064 resulted in a further increase of succinic acid production levels to 11.9 g/L (strain SUC-200, FIG. 20).

The results show that overexpression of a malate transporter in s S. cerevisiea comprising a deletion of alcohol dehydrogenase and glycerol-3-phosphate dehydrogenase genes resulted in a significant increase in succinic acid production levels. In addition it was shown that deletion of the gene adh1, adh2 and gpd1 (SUC 103) resulted in increased succinic acid production levels as compare to a wild type strain (SUC 101, Table 2).

Example 2F

Cloning of Phosphoenolpyruvate Carboxykinase from Actinobacillus succinogenes, Pyruvate Carboxylase from Saccharomyces cerevisiae, Malate Dehydrogenase from Saccharomyces cerevisiae, Fumarase from Rhizopus oryzae in Saccharomyces cerevisiae and Fumarate Reductase from Trypanosoma Brucei 2F.1. Gene Sequences Gene sequences of PEP carboxykinase from A. succinogenes, malate dehydrogenase from S. cerevisiae, fumarase from R. oryzae and fumarate reductase from T. brucei are described under 2F.1. Cytoplasmic pyruvate carboxylase from Saccharomyces cerevisiae (Pyc2p) [E.C. 6.4.1.1.], GenBank accession number 1041734, SEQ ID NO: 41, is encoded by the nucleotide sequence SEQ ID NO: 42. Genomic DNA from S. cerevisiae strain CEN.PK113-5D (MA TA ura3-52) was used as template to amplify the PYC2 coding sequence (SEQ ID NO: 42), using primers P1 (SEQ ID NO: 43) and P2 (SEQ ID NO: 44), and the Phusion DNA polymerase (Finnzymes, Finland) according to manufacturer's instructions. Convenient restriction sites were included in the primers for further cloning purposes.

2F.2. Construction of Expression Constructs

Figure 21:
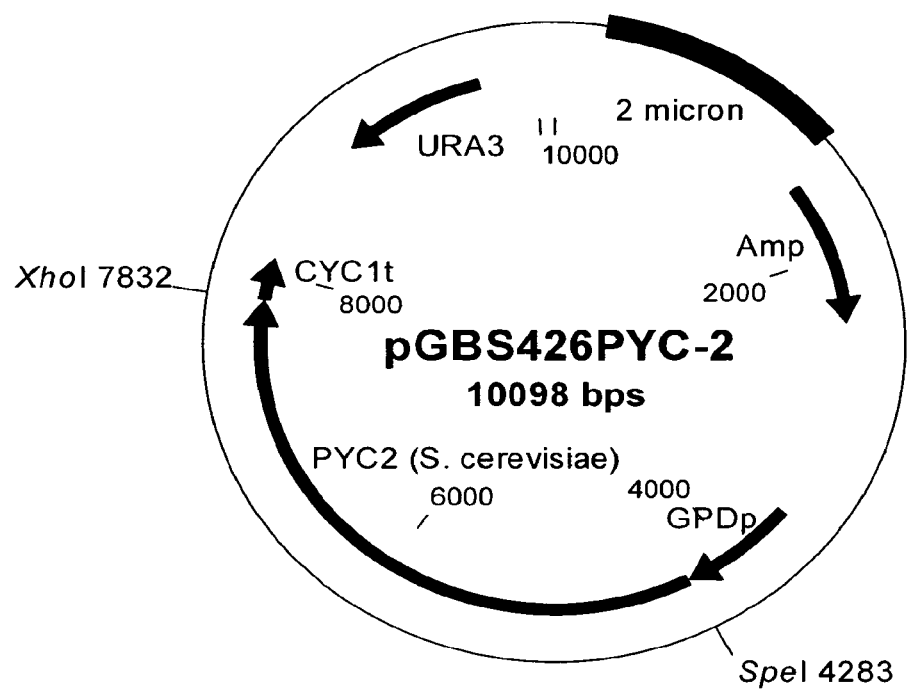
FIG. 21: Plasmid map of pGBS426PYC-2, containing pyruvate carboxylase from Saccharomyces cerevisiae for expression in Saccharomyces cerevisiae. The PYC2 coding nucleotide sequence was obtained by PCR using genomic DNA from strain CEN.PK113-5D as template and the PCR product was cloned into expression vector p426GPD.
Figure 22:
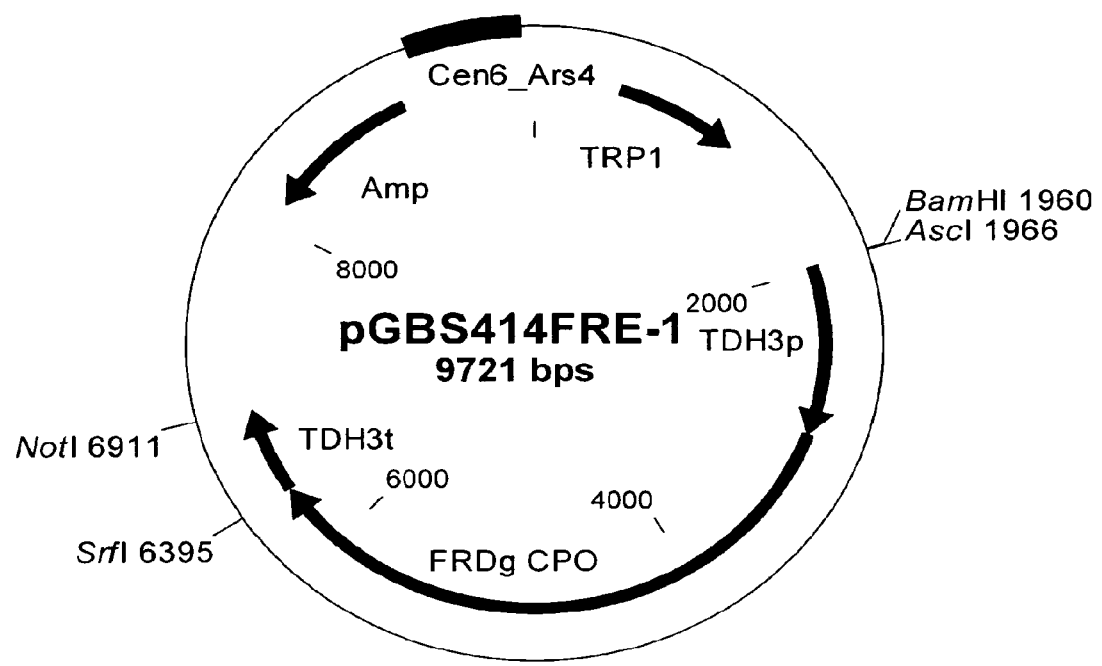
FIG. 22: Plasmid map of pGBS414FRE-1, encoding glycosomal fumarate reductase (FRDg) from Trypanosoma brucei for expression in Saccharomyces cerevisiae. The synthetic gene construct TDH3 promoter-FRDg-TDH3 terminator was cloned into expression vector pRS414.

The expression construct pGBS426PYC-2 (FIG. 21) was created after a SpeI/XhoI restriction of the S. cerevisiae expression vector p426GPD (Mumberg et al., Gene. 1995 Apr. 14; 156(1):119-22) and subsequently ligating in this vector a SpeI/XhoI restriction fragment consisting of the amplified PYC2 nucleotide sequence (SEQ ID NO: 42). The ligation mix was used for transformation of E. coli TOP10 (Invitrogen) resulting in the yeast expression construct pGBS426PYC-2 (FIG. 21). Construction of expression vectors pGBS414PPK-3 and pGBS415FUM-3 is described under 2C.2. Expression construct pGBS414FRE-1 was created after a BamHI/NotI restriction of the S. cerevisiae expression vector pRS414 (Sirkoski R. S. and Hieter P, Genetics, 1989, 122(1):19-27) and subsequently ligating in this vector a BamHI/NotI restriction fragment consisting of the glycosomal fumarate reductase (origin Trypanosoma brucei) synthetic gene construct (SEQ ID NO: 35). The ligation mix was used for transformation of E. coli TOP10 (Invitrogen) resulting in the yeast expression construct pGBS414FRE-1 (FIG. 22).

2F.3. S. cerevisiae Strains

Strains SUC-226, SUC-227, SUC-228 and SUC-230 were obtained by transformation of different combinations of the plasmids pGBS414FRE-1, pGBS414PPK-3, pGBS415FUM-1, pGBS426PYC-2 and p426GPD into strain CEN.PK113-6B (MATA ura3-52 leu2-112 trp1-289), as depicted in Table 5.

TABLE 5

Yeast strains constructed for Example 2F.

| Name | Background | Plasmids | Genes |
| --- | --- | --- | --- |
| SUC-226 | CEN.PK113-6B | PGBS414PPK-3 pGBS415FUM-3 p426GPD (empty vector) | PCKa, FRDg FUMR, MDH3 |
| SUC-227 | CEN.PK113-6B | PGBS414PPK-3 pGBS415FUM-3 pGBS426PYC-2 | PCKa, FRDg FUMR, MDH3 PYC2 |
| SUC-228 | CEN.PK113-6B | pGBS414FRE-1 pGBS415FUM-3 pGBS426PYC-2 | FRDg FUMR, MDH3 PYC2 |
| SUC-230 | CEN.PK113-6B | pGBS414FRE-1 pGBS415FUM-3 p426GPD (empty vector) | FRDg FUMR, MDH3 |

2F.4. Growth Experiments and Succinic Acid Production

Growth parameters and sample analysis were performed as described under example 2C.4 with the following modifications: pre-culturing was performed using 2% glucose (w/v) as carbon source. In the production medium 10% glucose (w/v) was used as carbon source.

Figure 23:
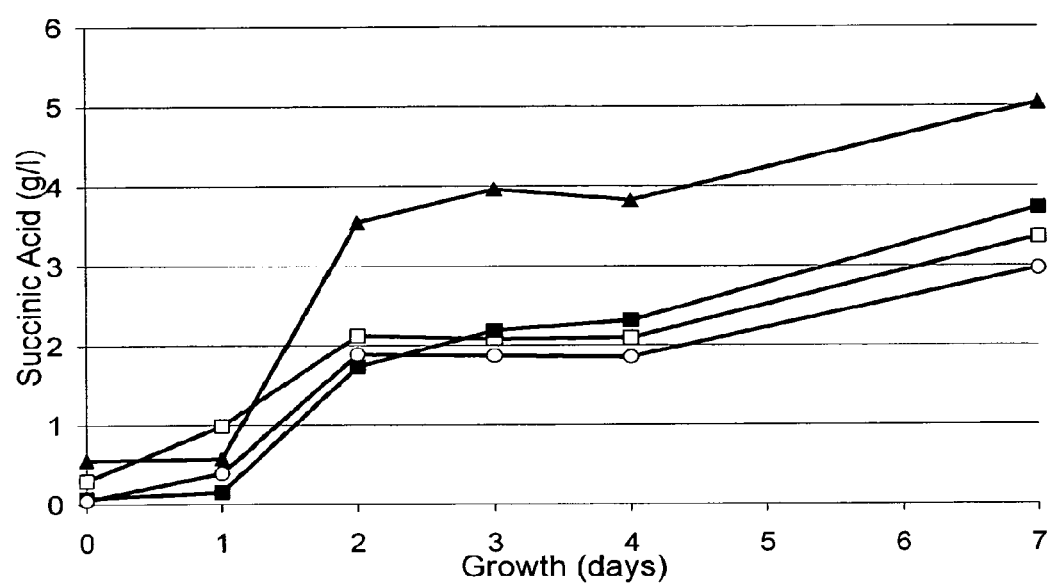
FIG. 23: Succinic acid levels in strains SUC-226 (□, PCKa, MDH3, FUMR, FRDg), -227 (▲, PYC2, PCKa, MDH3, FUMR, FRDg), SUC-228 (■, PYC2, MDH3, FUMR, FRDg) and SUC-230 (○, MDH3, FUMR, FRDg). Data represents the average of 3 independent growth experiments.

As depicted in FIG. 23 strain SUC-230, overexpressing MDH3, FUMR and FRDg, produced up to 3.0 g/L succinic acid. Additional overexpression of PCKa increased succinic acid production up to 3.4 g/L (strain SUC-226), and additional overexpression of PYC2 increased succinic acid production up to 3.7 g/L (strain SUC-228). Surprisingly, overexpression of both PCKa and PYC2 (SUC-227) resulted in 1.5 increase of succinic acid production levels up to 5.0 g/L, as compared to the effect of PCK and PYC alone. These results show a synergistic effect of combined overexpression of both PEP carboxykinase from *A. succinogenes* (PCKa) and pyruvate carboxylase from *S. cerevisiae* (PYC2) on succinic acid production levels in *S. cerevisiae*.

Example 3

Inactivation of Succinate Dehydrogenase Encoding Genes in *Aspergillus Niger*

3.1. Identification

Genomic DNA of *Aspergillus niger* strain CBS513.88 was sequenced and analyzed. Two genes with translated proteins annotated as homologues to succinate dehydrogenase proteins were identified and named sdhA and sdhB respectively. Sequences of the sdhA (An16g07150) and sdhB (An02g12770) loci are available on genbank with accession numbers 145253004 and 145234071 respectively. Gene replacement vectors for sdhA and sdhB were designed according to known principles and constructed according to routine cloning procedures (see FIG. 6). The vectors comprise approximately 1000 by flanking regions of the sdh ORFs for homologous recombination at the predestined genomic loci. In addition, they contain the *A. nidulans* bi-directional amdS selection marker driven by the gpdA promoter, in-between direct repeats. The general design of these deletion vectors were previously described in EP635574B and WO 98/46772.

3.2. Inactivation of the sdhA Gene in *Aspergillus niger*.

Figure 4:
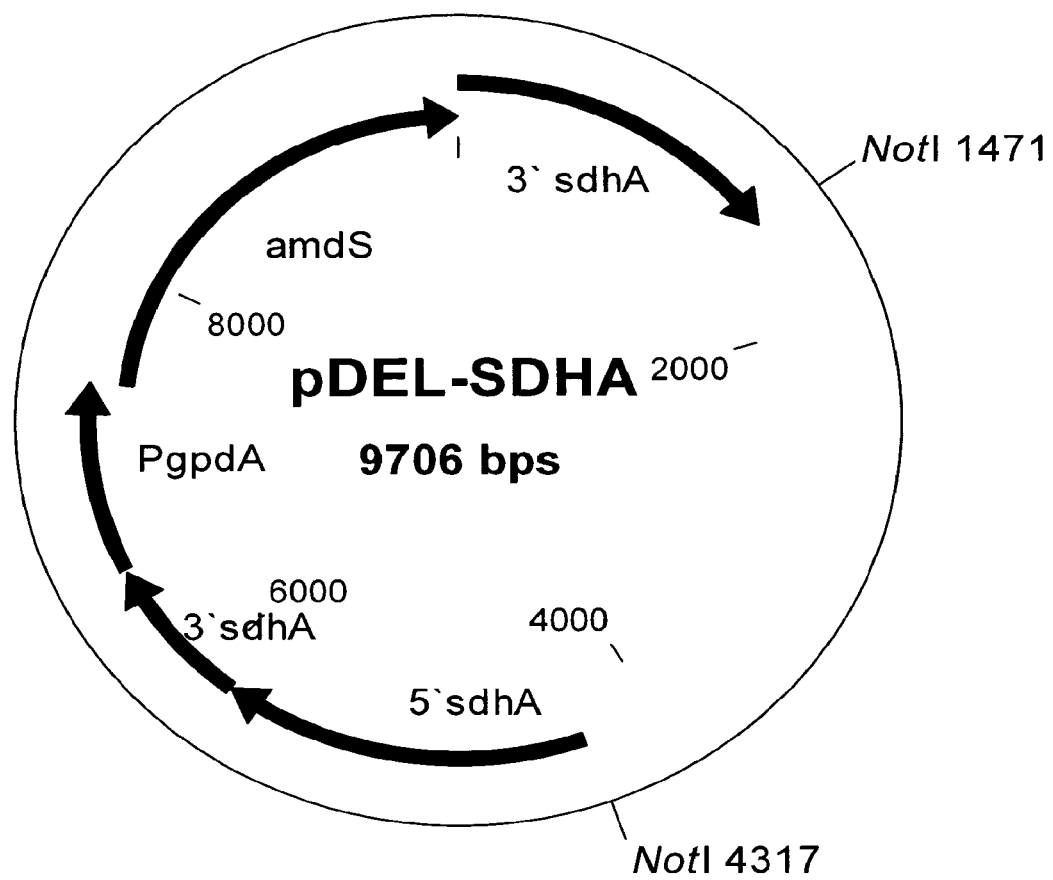
FIG. 4: Plasmid map of pDEL-SDHA
Figure 6:
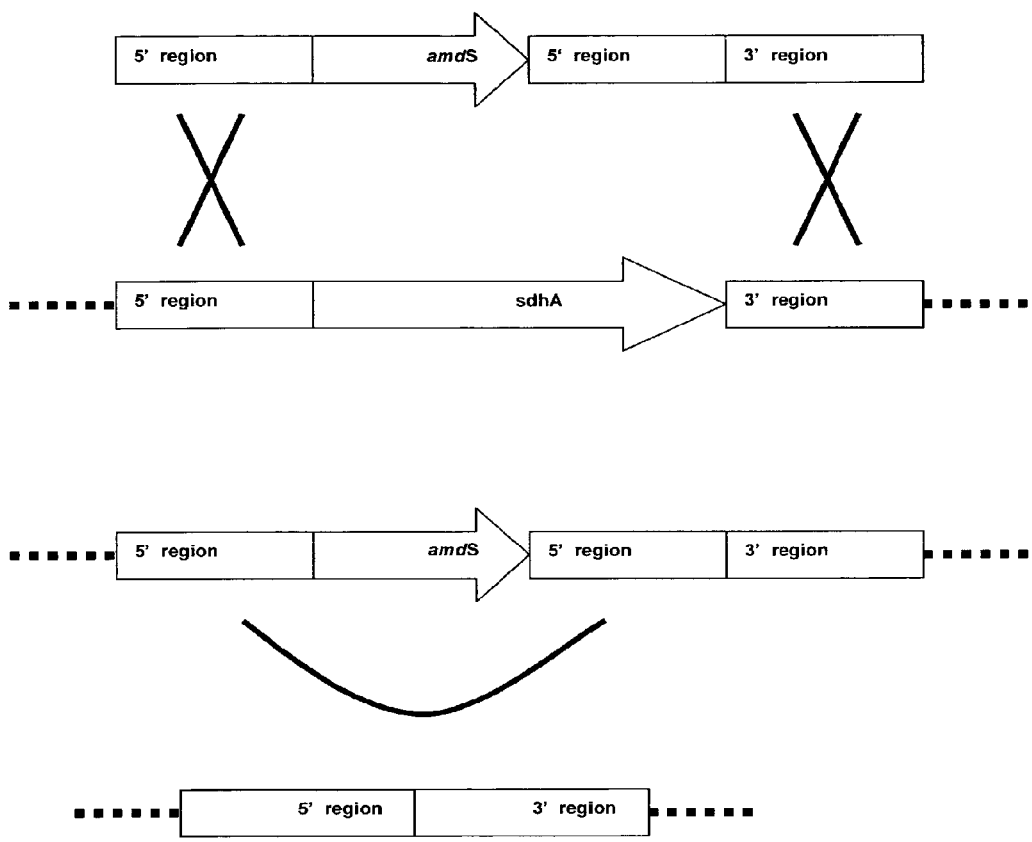
FIG. 6: Replacement scheme of sdhA

Linear DNA of deletion vector pDEL-SDHA (FIG. 4) was isolated and used to transform *Aspergillus niger* CBS513.88 as described in: Biotechnology of Filamentous fungi: Technology and Products. (1992) Reed Publishing (USA); Chapter 6: Transformation p. 113 to 156. This linear DNA can integrate into the genome at the sdhA locus, thus substituting the sdhA gene by the amdS gene as depicted in FIG. 6. Transformants were selected on acetamide media and colony purified according to standard procedures as described in EP635574B. Spores were plated on fluoroacetamide media to select strains, which lost the amdS marker. Growing colonies were diagnosed by PCR for integration at the sdhA locus and candidate strains tested by Southern analyses for deletion of the sdhA gene. Deletion of the sdhA gene was detectable by the ~2,2 kb size reduction of DNA fragments (4.6 kb wild-type fragment versus 2.4 kb for a successful deletion of SDHA) covering the entire locus and hybridized to appropriate probes. Approximately 9 strains showed a removal of the genomic sdhA gene from a pool of approximately 96 initial transformants.

Strain dSDHA was selected as a representative strain with the sdhA gene inactivated. The succinic acid production of dSDHA was determined in microtiterplates as described in Example 4.

Example 4

Cloning of FRDm from *Trypanosoma brucei* in *Aspergillus niger* dSDHA

*A. niger* strain dSDHA of example 3.2. was transformed with the expression construct pGBTOPAn1 (FIG. 5) comprising truncated mitochondrial fumarate reductase m1 (FRDm1, SEQ ID NO:7) as described in Example 1.1. *E. coli* DNA was removed by NotI digestion. *A. niger* transformants were picked using Qpix and transferred onto MTP's containing *Aspergillus* selective media. After 7 days incubation at 30 degrees Celsius the biomass was transferred to microtiter plates (MTP's) containing PDA by hand or colony picker. After 7 days incubation at 30 degrees Celsius, the biomass was sporulated. These spores were resuspended using the Multimek 96 (Beckman) in 100 microliters minimal enriched *Aspergillus* medium containing 10% glucose. Subsequently 2 MTP with 170 micoliters minimal enriched *Aspergillus* medium containing 10% glucose and 1% CaCO3 were inoculated with 30 microliters of the spore suspension. Likewise, *A. niger* strains dSDHA and CBS513.88 were inoculated in the MTP's. These MTP's were incubated for 5 days at 34 degrees Celsius 80% humidity. After 5 days 160 microliters were harvested using the Multimek 96 (Beckman) and succinic acid was determined by HPLC as described in Example 1.4. The results are shown in Table 6.

TABLE 6

Effect of deletion of succinate dehydrogenase (SDHA) and insertion of mitochondrial fumarate reductase (FRDm1) from *T. brucei* in *A. niger* on succinic acid production levels.

| *A. niger* strain | Succinic acid mg/l |
|---|---|
| CBS513.88 | 38 |
| dSDHA | 50 |
| dSDHA, + gGBTOPAn1 (FRDm1) | 583 |

Table 6 clearly shows an increased production of succinic acid by *A. niger* that comprises mitochondrial fumarate reductase from *T. brucei*

The invention claimed is:

1. A recombinant eukaryotic cell selected from the group consisting of a yeast and a filamentous fungus comprising and expressing a heterologous nucleotide sequence encoding a NAD(H)-dependent fumarate reductase that catalyses the conversion of fumaric acid to succinic acid wherein the NAD(H)-dependent fumarate reductase is active in the cytosol upon expression of the nucleotide sequence encoding the NAD(H)-dependent fumarate reductase, and wherein the heterologous nucleotide sequence encoding the NAD(H)-dependent fumarate reductase comprises an amino acid sequence that has at least 90% sequence identity with the amino acid sequence of SEQ ID NO: 3 and/or SEQ ID NO: 6.

2. The cell according to claim 1, wherein the heterologous nucleotide sequence encodes a NAD(H)-dependent fumarate reductase, comprising an amino acid sequence that has at least 95% sequence identity with the amino acid sequence of SEQ ID NO: 3 and/or SEQ ID NO: 6.

3. The cell according to claim 1, wherein the NAD(H)-dependent fumarate reductase is derived from a *Trypanosoma* sp.

4. The cell according to claim 1, wherein the cell further overexpresses a nucleotide sequence encoding a pyruvate carboxylase.

5. The cell according to claim 1, further comprising a nucleotide sequence encoding a heterologous phosphoenolpyruvate carboxykinase.

6. The cell according to claim 1, further comprising a nucleotide sequence encoding a malate dehydrogenase active in the cytosol upon expression of the nucleotide sequence encoding malate dehydrogenase.

7. The cell according to claim 1, further comprising a nucleotide sequence encoding an enzyme that catalyses the conversion of malic acid to fumaric acid in the cytosol, upon expression of the nucleotide sequence encoding enzyme that catalyses the conversion of malic acid to fumaric acid.

8. The cell according to claim 1, further comprising a nucleotide sequence encoding a dicarboxylic acid transporter.

9. The cell according to claim 1, wherein at least one gene of said cell encoding alcohol dehydrogenase is not functional.

10. The cell according to claim 1, wherein at least one gene of said cell encoding glycerol-3-phosphate dehydrogenase is not functional.

11. The cell according to claim 1, wherein at least one gene of said cell encoding succinate dehydrogenase is not functional.

12. The cell according to claim 1, which is an *Aspergillus*, optionally an *Aspergillus niger*.

13. The cell according to claim 1, which is a *Saccharomyces*, optionally a *Saccharomyces cerevisiae*.

14. A process for preparing succinic acid, comprising fermenting a eukaryotic cell according to claim 1, in a suitable fermentation medium, wherein succinic acid is prepared.

15. The process according to claim 14, wherein the succinic acid prepared is used for the production of a pharmaceutical, cosmetic, food, feed or chemical product.

16. The cell according to claim 1, wherein the heterologous nucleotide sequence encodes a NAD(H)-dependent fumarate reductase, comprising an amino acid sequence that has at least 97% sequence identity with the amino acid sequence of SEQ ID NO:3 and/or SEQ ID NO:6.

17. The cell according to claim 1, further comprising a nucleotide sequence encoding a phosphoenolpyruvate carboxylase.

* * * * *